(12) United States Patent
Vacanti et al.

(10) Patent No.: US 12,351,827 B2
(45) Date of Patent: Jul. 8, 2025

(54) SYSTEMS AND METHODS FABRICATING A MICROCHANNEL VASCULAR NETWORK DEVICE AND SEEDING A MICROCHANNEL

(71) Applicant: 3D BioLabs, LLC, Chadds Ford, PA (US)

(72) Inventors: Joseph Vacanti, Winchester, MA (US); Batzaya Byambaa, Cambridge, MA (US); Carly Comer, Boston, MA (US); Matthew Hancock, Newton, MA (US); Tyler Lieberthal, Brookline, MA (US); Tatevik Sahakyants, Lexington, MA (US); Andrew Spann, Newton, MA (US); Craig Neville, Melrose, MA (US)

(73) Assignee: 3D BioLabs, Inc., Chadds Ford, PA (US)

( * ) Notice: Subject to any disclaimer, the term of this patent is extended or adjusted under 35 U.S.C. 154(b) by 808 days.

(21) Appl. No.: 16/905,898

(22) Filed: Jun. 18, 2020

(65) Prior Publication Data
US 2021/0071145 A1    Mar. 11, 2021

Related U.S. Application Data

(60) Provisional application No. 62/863,169, filed on Jun. 18, 2019, provisional application No. 62/863,165, filed on Jun. 18, 2019.

(51) Int. Cl.
*B29C 64/393* (2017.01)
*B33Y 50/02* (2015.01)
(Continued)

(52) U.S. Cl.
CPC .......... *C12N 5/0671* (2013.01); *B29C 64/393* (2017.08); *B33Y 50/02* (2014.12);
(Continued)

(58) Field of Classification Search
CPC ..... B29C 64/393; B33Y 50/02; C12N 5/0671; C12N 2513/00; C12N 2533/30–40; C12M 23/16; C12M 41/48
See application file for complete search history.

(56) References Cited

U.S. PATENT DOCUMENTS 6,139,574 A * 10/2000 Vacanti ................. B29C 64/165
623/901
2002/0059049 A1    5/2002 Bradbury et al.
(Continued)

FOREIGN PATENT DOCUMENTS

JP    H 11-507256 A    6/1999
JP    2018-501083 A    1/2018
(Continued)

OTHER PUBLICATIONS

Alzanbaki et al., 2021, "Engineered microgels—Their manufacturing and biomedical applications," Micromachines, 12(1), p. 1-19.
(Continued)

*Primary Examiner* — John J DeRusso
(74) *Attorney, Agent, or Firm* — MORGAN, LEWIS & BOCKIUS LLP

(57) ABSTRACT

A method of fabricating a microchannel device is provided. The method includes determining, based on a plurality of design criteria, a microchannel vascular network design. The microchannel vascular network design includes a first channel network, a second microchannel network based on the first channel network, and a structure for providing fluidic communication through between the first channel network and the second channel network. The method includes receiving, in electronic form, the microchannel vascular network design at a fabrication system. The fabrication system comprises a pre-polymer solution. The method includes forming, based on the microchannel vascular network design, a microchannel vascular network device of a
(Continued)

500

*(502)* Determine, based on a plurality of design criteria, a microchannel vascular network design. The microchannel vascular network design includes a first channel network, a second microchannel network based on the first channel network, and a structure for providing fluidic communication through between the first channel network and the second channel network.

*(504)* Receiving, in electronic form, the microchannel vascular network design at a fabrication system. The fabrication system includes a pre-polymer solution.

*(506)* Form, based on the microchannel vascular network design, a microchannel vascular network device of a polymer material at the fabrication system using the pre-polymer solution, thereby fabricating the microchannel vascular network device.

polymer material at the fabrication system using the pre-polymer solution, thereby fabricating the microchannel vascular network device.

20 Claims, 43 Drawing Sheets

(51) Int. Cl.
    *C12M 3/06*     (2006.01)
    *C12N 5/071*     (2010.01)
    *C12N 13/00*     (2006.01)

(52) U.S. Cl.
    CPC ............. *C12M 23/16* (2013.01); *C12N 13/00* (2013.01); *C12N 2513/00* (2013.01); *C12N 2529/10* (2013.01); *C12N 2533/30* (2013.01); *C12N 2533/54* (2013.01)

(56) References Cited

U.S. PATENT DOCUMENTS

| | | | |
|---|---|---|---|
| 2010/0234678 A1* | 9/2010 | Pryor | ............... A61F 2/062 435/395 |
| 2011/0033887 A1 | 2/2011 | Fang et al. | |
| 2014/0147880 A1 | 5/2014 | Ingber et al. | |
| 2014/0234953 A1* | 8/2014 | Vacanti | ............... C12M 21/08 435/297.1 |
| 2017/0009194 A1 | 1/2017 | Golway et al. | |
| 2018/0002658 A1 | 1/2018 | Miller et al. | |
| 2018/0172666 A1 | 6/2018 | Chung et al. | |
| 2018/0312792 A1 | 11/2018 | Trinkle et al. | |
| 2019/0076840 A1 | 3/2019 | Gottardi et al. | |

FOREIGN PATENT DOCUMENTS

| | | |
|---|---|---|
| WO | WO 2003/082145 A2 | 10/2003 |
| WO | WO 2009/042671 A1 | 4/2009 |
| WO | WO 2016/154070 A1 | 9/2016 |

OTHER PUBLICATIONS

Chaenyung et al., 2014, "Microfluidics-assisted fabrication of gelatin-silica core-shell microgels for injectable tissue constructs," Biomacromolecules 15(1), p. 283-290.
Chen et al., 2016, "Fabrication of Gelatin Methacrylate/nanohydroxyapatite microgel arrays for periodontal tissue regeneration," International Journal of Nanomedicine, 11, p. 4707-4718.
Correia, M., 2016, "Multifunctional and Liquified Capsules for Tissue Regeneration," University of Minho, p. 1-348.
Nichol, J.W. et al., 2010, "Cell-laden microengineered gelatin methacrylate hydrogels," Biomaterials 31(21), p. 5536-5544.
Tasoglu et al., 2014, "Guided and magnetic self-assembly of tunable magnetoceptive gels," Nature communications 5(1), p. 1-11.
Xu, X. et al., 2024, "A Universal Strategy to Construct High-Performance Homo-and Heterogeneous Microgel Assembly Bioinks," Small Methods, p. 2400223 (1-14).
Yue, K. et al., "Synthesis, properties, and biomedical applications of gelatin methacryloyl (GelMA) hydrogels," Biomaterials, Aug. 28, 2015, vol. 73, pp. 254-271.

* cited by examiner

500

(502) Determine, based on a plurality of design criteria, a microchannel vascular network design. The microchannel vascular network design includes a first channel network, a second microchannel network based on the first channel network, and a structure for providing fluidic communication through between the first channel network and the second channel network.

(504) Receiving, in electronic form, the microchannel vascular network design at a fabrication system. The fabrication system includes a pre-polymer solution.

(506) Form, based on the microchannel vascular network design, a microchannel vascular network device of a polymer material at the fabrication system using the pre-polymer solution, thereby fabricating the microchannel vascular network device.

*(602)* Prepare, based on a candidate subject, a microchannel vascular network device, thereby forming a prepared microchannel vascular network device. The prepared microchannel vascular channel device includes a first channel network and a second channel network.

*(604)* Seed, based on the candidate subject, the plurality of cells for culturing in the prepared microchannel vascular device, thereby forming a plurality of seed cells.

*(606)* Flow, using a bioreactor system coupled to the prepared microchannel vascular network device, a culture medium comprising the plurality of seed cells through the prepared microchannel vascular network device, thereby culturing the plurality of cells in the microchannel vascular network device.

Fig 6

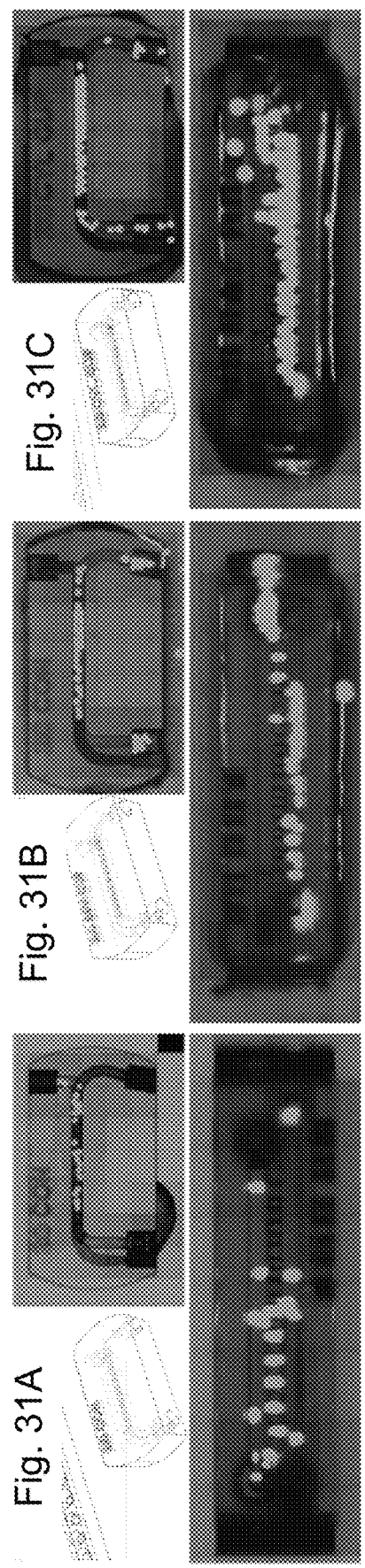

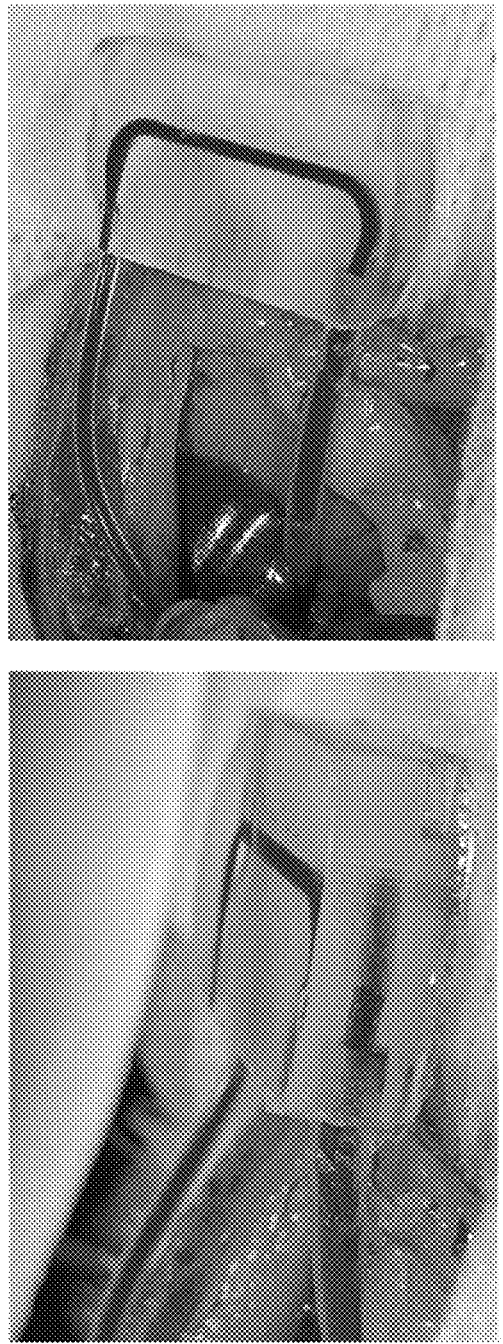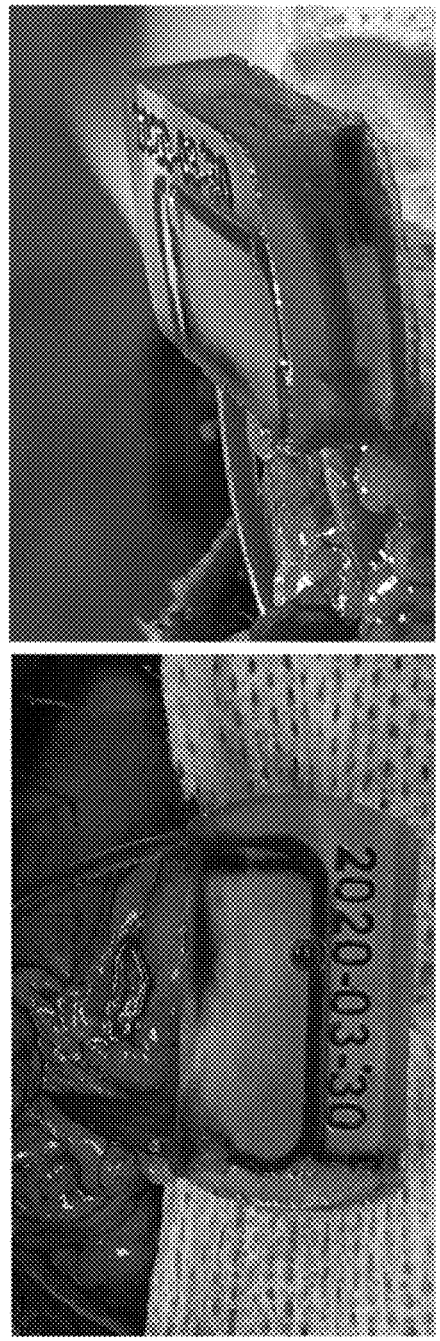
Fig. 36

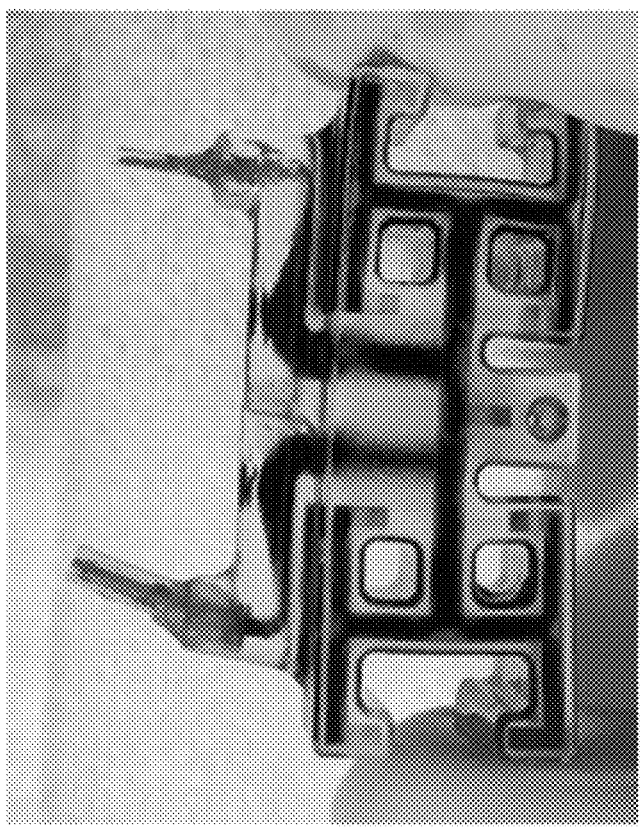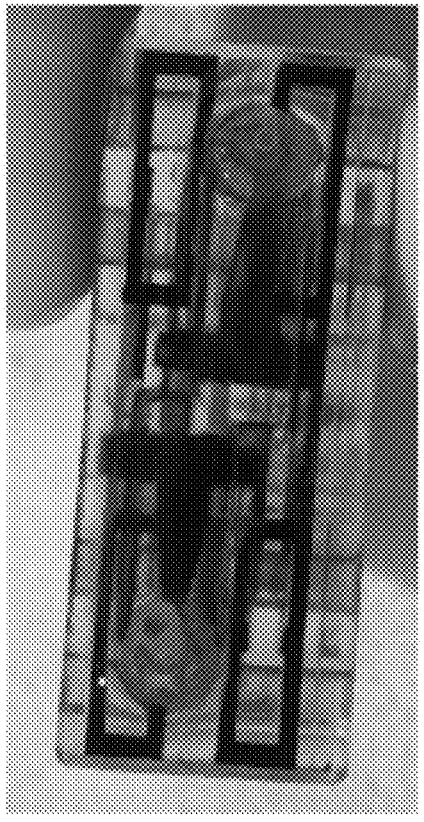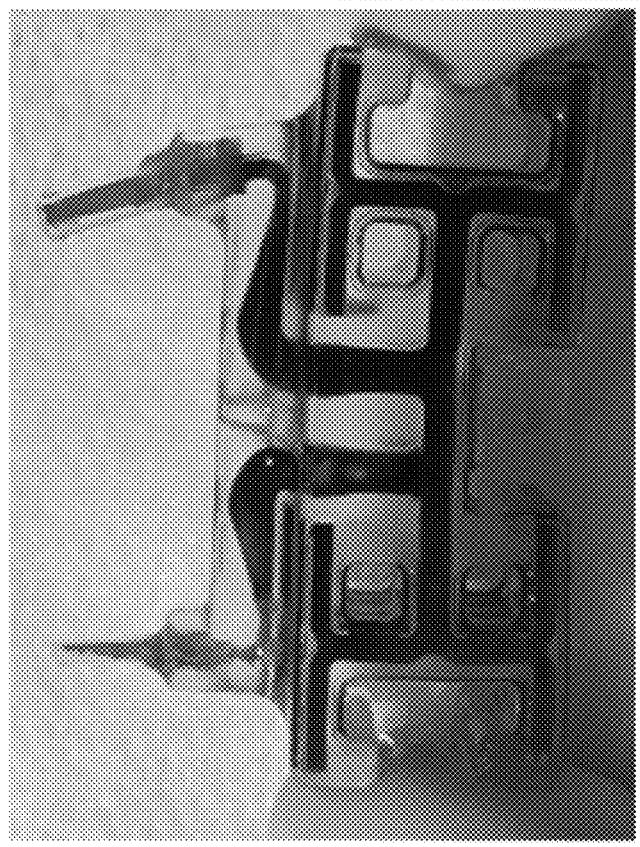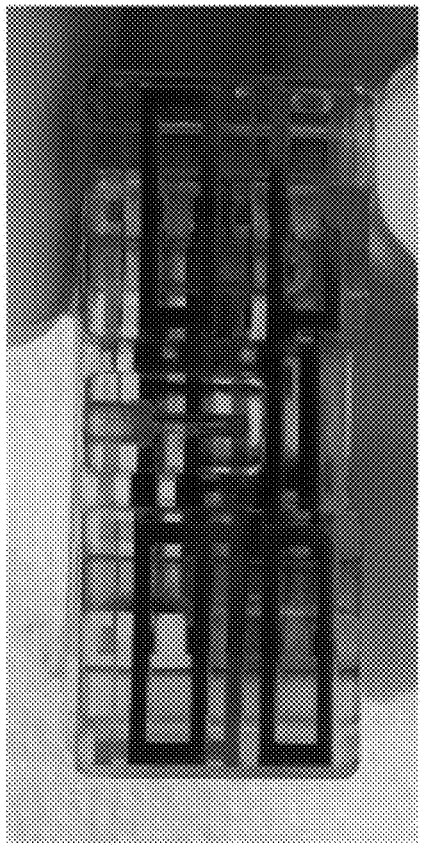
Fig. 38

SYSTEMS AND METHODS FABRICATING A MICROCHANNEL VASCULAR NETWORK DEVICE AND SEEDING A MICROCHANNEL

CROSS REFERENCE TO RELATED APPLICATION

This application claims the benefit of U.S. Provisional Application No. 62/863,165, filed Jun. 18, 2019, entitled "Systems and Methods for Retarding or Arresting Flow in a Microchannel," and U.S. Provisional Application No. 62/863,169, filed Jun. 18, 2019, entitled "Systems and Methods for Directing Flow in a Bioreactor Device," each of which is hereby incorporated by reference in its entirety.

BACKGROUND OF THE INVENTION

Field of the Invention

The present disclosure relates to vascular networks. More particularly, the present disclosure relates to systems and methods for fabricating a microchannel vascular network and seeding a microchannel.

Description of Related Art

Gelatin methacryloyl (GelMA) hydrogels have been widely adopted throughout a variety of biomedical applications, including the generation of three-dimensional biofabricated tissue analogs. This widespread adoption is due, in part, to the combined desired biological properties of gelatin and the alterable physical characteristics that the GelMA hydrogels exhibit, as well as the cell attaching and matrix metalloproteinase response peptide motif characteristics of the hydrogel. These attributes closely resemble various properties of a native extracellular matrix, which are essential to the various biomedical applications that the GelMA hydrogel is utilized by.

In some biomedical applications, it is desirable to have a configurable device that includes one or more microchannels and allows for a controllable flow of a medium within the device. For instance, during a process including seeding cells within such a device, the microchannels of the device require the flow to be retarded or arrested therethrough in order to allow for the cells to properly attach to various walls of the device without being detached from the flow itself. Once the cells have properly attached to the walls of the device, flow within the microchannels may need to be accelerated or reopened to allow for a supply of nourishment to the cells and/or a removal of waste products produced by the cells. However, such temporary retarding or arresting of microchannels has been unattainable as of yet.

Moreover, bioreactors have been developed for culturing various types of cells, and subsequently conducting experiments on the cultured cells. For instance, conventional bioreactors include a well for culturing cells and a flow of fluid therethrough. However, these devices lack a means for providing a flow of fluid in more than one direction and controlling a direction of the flow. Additionally, these devices require the cells to be removed from the bioreactor once cultured, and are only capable of culturing spheroid models of cells.

Additionally, vascular network devices have been developed for culturing various types of cells and conducting analysis, and/or implantation in a subject. However, these vascular network devices have yet to allow for culturing physiologically relevant masses of differing geometries. Furthermore, these vascular network devices cannot culture these masses using biodegradable materials.

Thus, prior to the present disclosure there existed a need for a method of retarding or arresting flow in microchannels. Furthermore, prior to the present disclosure there existed a need for systems and methods for directing flow in cell culturing devices capable of culturing physiologically relevant masses of differing geometries. Additionally, prior to the present disclosure, there existed a need for systems and methods for fabricating microchannel vascular network devices capable culturing physiologically relevant masses of differing geometries.

The information disclosed in this Background of the Invention is only for enhancement of understanding of the general background of the invention and should not be taken as an acknowledgement or any form of suggestion that this information forms the prior art already known to a person skilled in the art.

BRIEF SUMMARY

Given the above background, what is needed in the art are systems and methods for fabricating a microchannel vascular network device and seeding a plurality of cells within a respective microchannel vascular network device.

The present disclosure provides improved systems and methods for fabricating a microchannel vascular network device and seeding a plurality of cells within a respective microchannel vascular network device.

In more detail, one aspect of the present disclosure provides a method of fabricating a microchannel vascular network device. The method includes determining, based on a plurality of design criteria, a microchannel vascular network design. The microchannel vascular network design includes a first channel network, a second microchannel network based on the first channel network, and a structure for providing fluidic communication through between the first channel network and the second channel network. The method includes receiving, in electronic form, the microchannel vascular network design at a fabrication system. Additionally, the fabrication system includes a pre-polymer solution. Furthermore, the method includes forming, based on the microchannel vascular network design, a microchannel vascular network device of a polymer material at the fabrication system using the pre-polymer solution. In this way, the method facilitates fabricating the microchannel vascular network device.

In some embodiments, the determining further includes determining one or more design criteria in the plurality of the design criteria that is associated with the forming of the polymer material from the pre-polymer solution.

In some embodiments, the polymer material includes poly-dimethyl-siloxane (PDMS), poly-glycerol-sebacate (PGS), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon©, nylon silicon, and shape memory materials, such as poly(styrene-block-butadiene), polynorbornene, hydrogels, metallic alloys, and oligo (ε-caprolactone)diol as switching segment/oligo (p-dioxyanone) diol as physical crosslink.

In some embodiments, the polymer is a biodegradable material.

In some embodiments, the pre-polymer solution includes a photoinitiator. Moreover, the forming includes exposing the pre-polymer solution to ultraviolet light for a predetermined period of time.

In some embodiments, the polymer material of the microchannel vascular network device is transparent.

In some embodiments, the structure includes a first end portion in communication with the first channel network with the first end portion including a first diameter, and a second end portion in communication with the second channel network with the second end portion including a second diameter. Moreover, the first diameter and the second diameter of the structure define an interior transition region of the structure.

In some embodiments, the first diameter is different from the second diameter.

In some embodiments, the first diameter is from about 992 microns (μm) to about 623 μm, and the second diameter is from about 832 μm to about 553 μm.

In some embodiments, the interior transition region of the structure includes an interior surface define by revolving a continuous, smooth curve about an axis of the structure.

In some embodiments, the continuous, smooth curve comprises a conical shape, an ellipsoidal shape, or a cylindrical shape.

In some embodiments, the interior transition region of the structure includes an interior surface define by a monotonic function.

In some embodiments, the interior transition region of the structure includes a corresponding length from about 399 μm to about 701 μm.

In some embodiments, a length defined from a first end portion to a second end portion of the microchannel vascular network device is from about 15 centimeters (centimeters) to about 7.5 cm.

In some embodiments, the plurality of design criteria comprise one or more length design criteria, one or more mass design criteria, one or more temporal design criteria, one or more polymer design criteria, one or more temporal design criteria, one or more illuminance design criteria, or a combination thereof.

In some embodiments, the one or more length design criteria in the plurality of design criteria of the determining includes a first length associated with the microchannel vascular network design and a second length associated with the microchannel vascular network device. Furthermore, in some embodiments, the second size is less than the first size.

In some embodiments, the second length is based on the first length, the polymer, the fabrication system, or a combination thereof.

In some embodiments, the one or more polymer design criteria in the plurality of design criteria includes selecting the polymer of the forming based on a degree of swelling of the polymer.

In some embodiments, the one or more length design criteria in the plurality of design criteria includes a resolution of a length of the microchannel vascular network device.

In some embodiments, the one or more polymer design criteria in the plurality of design criteria includes a porosity of the microchannel vascular network device.

In some embodiments, a median size of a pore of the microchannel vascular network device is from about 19 μm to about 231 μm.

In some embodiments, the fabrication system utilizes an additive manufacturing method for the forming.

In some embodiments, the forming forms the microchannel vascular network device with a positive mold, thereby forming a void in between the first channel network and the second channel network.

In some embodiments, the forming forms the microchannel vascular network device with a positive mold, thereby forming a void in between the first channel network and the second channel network.

In some embodiments, the additive manufacturing method is selected from the group consisting of: binder jetting, material extrusion, material jetting, polyjet, powder bed, sheet lamination, and vat photopolymerization.

Another aspect of the present disclosure is directed to providing a method of retarding or arresting flow in a microchannel device. The microchannel device includes a first channel and a second channel. The first channel and the second channel being interconnected by one or more structures. Accordingly, the method includes perfusing a suspension including a plurality of GelMA microgels in a solution through the first channel of the device. Accordingly, the perfusing the solution causes one or more GelMA microgels to retard or arrest flow in at least one of the one or more structures.

In some embodiments, the plurality of GelMA microgels is fabricated using a photomasking technique.

In some embodiments, the photomasking technique includes disposing a pre-polymer solution comprising GelMA in a buffer solution and a photoinitiator onto a first slide whose outer edge portion is surrounded by a spacer. A second slide is disposed above the first slide upon completion of the disposing of the pre-polymer solution onto the first slide, thereby forming a contained structure. The method includes disposing a photomask on a top surface of the second slide. Furthermore, the method includes exposing the photomask and the contained structure to ultraviolet light for a predetermined period of time, thereby generating GelMA microgels.

In some embodiments, the method further includes disassembling the contained structure to retrieve the generated GelMA microgels, thereby fabricating the plurality of GelMA microgels.

In some embodiments, the pre-polymer solution includes of from about 7% to about 20% parts by weight GelMA, and about 1% photoinitiator.

In some embodiments, the pre-polymer solution is formed with a degree of methacryloyl substitution of from about 75% to about 90%.

In some embodiments, the array of transparencies is an array of circles. Each circle in the array of circles has a diameter of from about 50 micrometers (μm) to about 650 μm.

In some embodiments, the spacer has a thickness of from about 50 μm to about 550 μm.

In some embodiments, prior to the disposing the pre-polymer solution, for at least one slide and/or spacer the method further includes disposing a sample of a stock solution of about 0.5 wt % of methoxy polyethylene glycol 5000 Si (mPEG5000-Si), about 1 wt % acetic acid, and ethyl alcohol onto the at least one slide and/or spacer. Additionally, the method includes subjecting the at least one slide and/or spacer to an incubation at about 70° C. for about 30 minutes, thereby forming an incubated slide and/or spacer.

By immersing the incubated slide and/or spacer in deionized water, an immersed slide and/or spacer is formed. Moreover, the method includes sonicating the immersed slide and/or spacer for a predetermined period of time, thereby forming a sonicated slide and/or spacer. Furthermore, the method includes drying the sonicated slide and/or spacer, thereby forming a prepared slide and/or spacer.

In some embodiments, the predetermined period of time is less than or equal to about 30 seconds.

In some embodiments, the ultraviolet light has a wavelength of from about 360 nanometers (nm) to about 480 nm, and an intensity of about 12.4 milliwatts per cubic centimeter.

In some embodiments, the retrieving the GelMA microgels includes transferring the generated GelMA microgels into a mineral oil bath, and agitating the mineral oil bath.

In some embodiments, the retrieving the GelMA microgels includes immersing the generated GelMA microgels in a sodium hydroxide solution. Furthermore, the retrieving includes immersing the GelMA microgels of immersing in an ethyl alcohol solution, and sonicating the GelMA microgels of retrieving for a third predetermined period of time.

In some embodiments, the plurality of GelMA microgels is fabricated using a microfluidic process.

In some embodiments, the one or more GelMA microgel in the plurality of GelMA microgels is formed as a sphere.

In some embodiments, the one or more structures is in a shape of a truncated cone.

In some embodiments, the method further includes, subsequent to the perfusing the suspension of the plurality of GelMA microgels and the first solution through the first channel of the device, applying a flow of fluid in the second channel of the device, thereby creating a pressure differential between the first channel and the second channel of the device.

Yet another aspect of the present disclosure is directed to providing a bioreactor system. The bioreactor control system in configured for controlling a flow through a microchannel vascular network device. Moreover, the bioreactor control system includes one or more processors, a memory coupled to the one or more processors, and a controller coupled to the memory and the one or more processors. Furthermore, the bioreactor control system includes the microchannel vascular network device. The microchannel vascular network device includes an inlet channel including a first inflow opening and a first outflow opening, a well that is configured to hold a cell culture insert, and an outlet channel. The well includes an inlet in communication with the first outflow opening, an outlet that is disposed below the cell culture insert and in communication with a second inflow opening of an outlet channel. The outlet channel includes the second inflow opening and a second outflow opening. Furthermore, the bioreactor system includes a pump coupled to the microchannel vascular network device and configured to promote a flow of a fluid through the microchannel vascular network device from the inlet channel through the outlet channel based on one or more instructions provided by the controller.

In some embodiments, the bioreactor system further comprises a caplet disposed above the cell culture insert and removably coupled to the microchannel vascular network device.

In some embodiments, the caplet of the device comprises a second outlet.

In some embodiments, the caplet is shaped as an inverted funnel.

In some embodiments, the caplet is coupled to the well via an O-ring.

In some embodiments, each surface of the caplet that is in contact with at least a wall of the well includes a hydrophobic material.

In some embodiments, the O-ring includes a hydrophobic material.

In some embodiments, the cell culture insert is a sponge or a mesh.

In some embodiments, the cell culture insert is coated in gelatin.

In some embodiments, the bioreactor system includes a plurality of microchannel vascular network devices connected in series and in fluidic communication with each other such that a respective inlet channel of a second microchannel vascular network device in the plurality microchannel vascular network devices is coupled to a respective outlet channel of a first microchannel vascular network device.

In some embodiments, the bioreactor system includes a plurality of microchannel vascular network devices, wherein the plurality of microchannel vascular network devices is connected in parallel, such that each microchannel vascular network device the plurality of microchannel vascular network devices is coupled to the pump.

Yet another aspect of the present disclosure is directed to providing a method of culturing a plurality of cells in a microchannel vascular network device, the method includes preparing, based on a candidate subject, a microchannel vascular network device, thereby forming a prepared microchannel vascular network device, wherein the prepared microchannel vascular channel device includes a first channel network, and a second channel network. Furthermore, the method includes seeding, based on the candidate subject, the plurality of cells for culturing in the prepared microchannel vascular device, thereby forming a plurality of seed cells.

Additionally, the method includes flowing, using a bioreactor system coupled to the prepared microchannel vascular network device, a culture medium comprising the plurality of seed cells through the prepared microchannel vascular network device, thereby culturing the plurality of cells in the microchannel vascular network device.

In some embodiments, the preparing further includes, preparing the plurality of cells for the seeding.

In some embodiments, the preparing the plurality of cells includes exposing the plurality of cells to a solution. The solution includes calcium and magnesium.

In some embodiments, an exposure time of the plurality of cells to the solution is from about 15 minutes to about 25 minutes.

In some embodiments, the preparing the microchannel vascular network device includes modifying a surface of the microchannel vascular network device.

In some embodiments, the surface modification of the microchannel vascular network device is a chemical surface modification.

In some embodiments, the chemical surface modification comprises forming a peptide conjugation on the surface of the microchannel vascular network device.

In some embodiments, the peptide conjugation is an arginylglycylaspartic acid peptide.

In some embodiments, the surface modification of the microchannel vascular network device is a mechanical surface modification.

In some embodiments, the mechanical surface modification includes applying a coating to the surface of the microchannel vascular network device.

In some embodiments, the coating includes collagen, fibronectin, gelatin, GelMA, PEGdA, PLL, or a combination thereof.

In some embodiments, the coating includes a first percentage by weight (wt %) of PEGdA from about 8% to about 12%, and a second wt % of GelMa from about 0.5% to about 7%.

In some embodiments, the first wt % of PEGdA is 10%, and the second wt % of GelMA from about 1% to about 5%.

In some embodiments, the coating includes a first coating comprising PEGdA, PPL, GelMA, or a combination thereof. The first coating including an first upper surface and a first lower surface. The coating further includes a second coating including either collagen or gelatin. The second coating includes second upper surface and a second lower surface. Furthermore, the first lower surface is adjacent to the surface of the microchannel vascular network device, and the second lower surface is adjacent to the first upper surface.

In some embodiments, the seeding includes encapsulating the plurality of cells in the culture medium.

In some embodiments, the culture medium includes a photoinitiator, and preceding the encapsulating the plurality of cells, the seeding further includes exposing the culture medium and the plurality of cells to ultraviolet light for a predetermined period of time.

In some embodiments, the culture medium includes a thickness from about 5 µm to about 15 µm.

In some embodiments, a density of the plurality of seed cells of the seeding from about $1*10^4$ cells per square cm to about $1*10^5$ cells per square cm.

In some embodiments, a flow rate of the flowing is from about 375 microliters (µL) per minute to about 425 µL per minute.

In some embodiments, prior to the flowing, a portion of the prepared microchannel vascular network device is in either a dry condition or a hydrated condition.

In some embodiments, prior to the flowing, the portion of the prepared microchannel vascular network device is a lower end portion of the microchannel vascular network device.

The retarding or arresting of flow in microchannels of the present invention have other features and advantages that will be apparent from, or are set forth in more detail in, the accompanying drawings, which are incorporated herein, and the following Detailed Description, which together serve to explain certain principles of exemplary embodiments of the present invention.

Other features and advantages of the invention will be apparent from, or are set forth in more detail in, the accompanying drawings, which are incorporated herein, and the following Detailed Description, which together serve to explain certain principles of exemplary embodiments of the present invention.

BRIEF DESCRIPTION OF THE DRAWINGS

FIG. 5 illustrates a first flow chart of methods for fabricating a microchannel vascular network device, in accordance with embodiments of the present disclosure, in which optional elements are indicated by dashed boxes and/or lines;

FIG. 6 illustrates a second flow chart of methods for seeding a plurality of cells in a microchannel vascular network device, in accordance with embodiments of the present disclosure, in which optional elements are indicated by dashed boxes and/or lines;

FIGS. 25, 26, 27, 28, 29, 30A, 30B, 30C, 30D, 31A, 31B, 31C, 32, 33, 34, 35, 36, 37, 38, 39, and 40 illustrate examples for systems and methods for fabricating and culturing cells in a microchannel vascular network device, in accordance with embodiments of the present disclosure.

Figure 1:
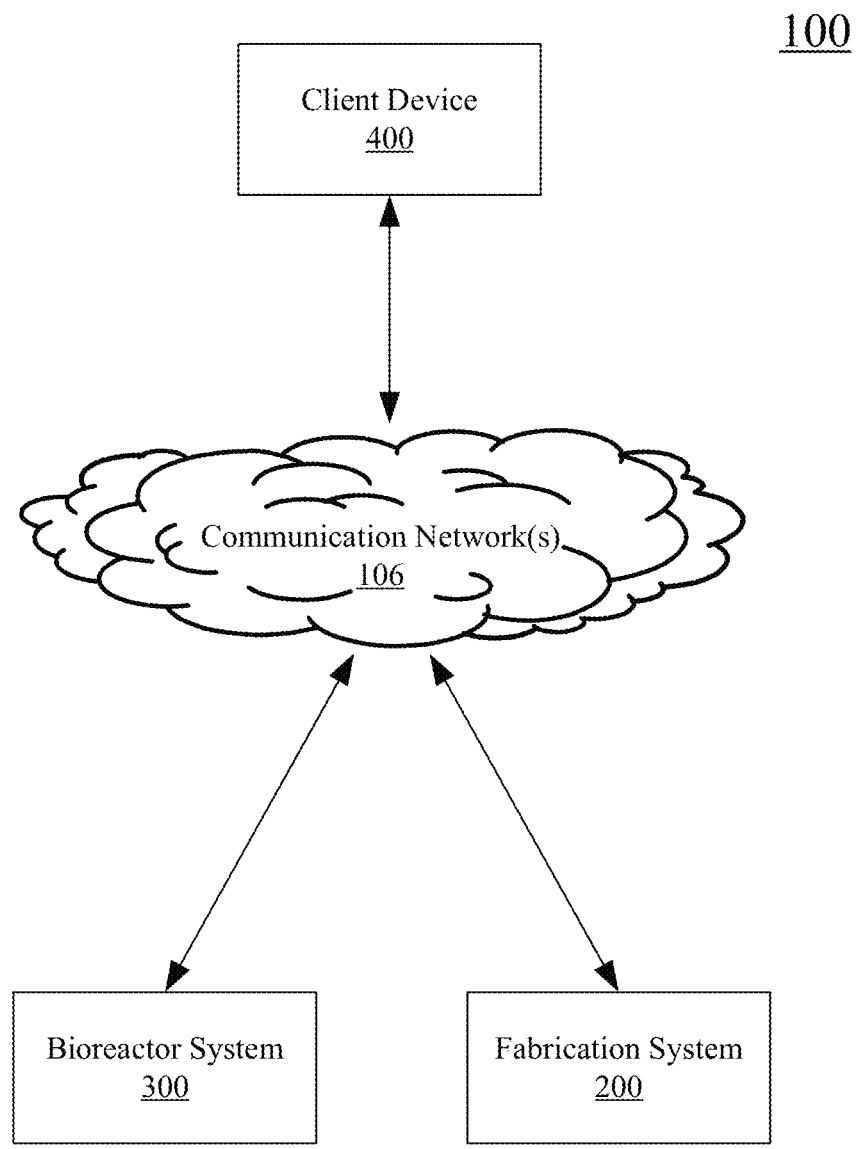
FIG. 1 illustrates a block diagram illustrating an embodiment of a system for fabricating a microchannel vascular network device and/or seeding a plurality of cells in a microchannel device, in accordance with embodiments of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, and components have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For instance, a first graphical chart could be termed a second graphical chart, and, similarly, a second graphical chart could be termed a first graphical chart, without departing from the scope of the present disclosure. The first graphical chart and the second graphical chart are both graphical charts, but they are not the same graphical chart.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The foregoing description included example systems, methods, techniques, instruction sequences, and computing machine program products that embody illustrative implementations. For purposes of explanation, numerous specific details are set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions below are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of +20%, +10%, +5%, or +1% of a given value. Where particular values are described in the application and claims, unless otherwise stated, the term "about" means within an acceptable error range for the particular value. The term "about" can have the meaning as commonly understood by one of ordinary skill in the art. The term "about" can refer to +10%. The term "about" can refer to +5%.

As used herein, the term "biological sample," "patient sample," or "sample" refers to any sample taken from a subject, which includes nucleic acids reflecting the genotype of the subject with respect to the loci described herein. Examples of biological samples include, but are not limited to, blood samples, saliva samples, buccal cell samples, and the like. A sample can be a liquid sample or a solid sample (e.g., a cell or tissue sample).

As used herein, the term "equally spaced" means that a distance from a first feature to a corresponding second feature is the same for successive pairs of features unless expressly stated otherwise.

By "biodegradeable," as used herein, is meant materials that are bioresorbable and/or degrade and/or break down by mechanical degradation (e.g., dissolve, resorb, etc.) upon interaction with a physiological environment into components that are metabolizable or excretable, over a period of time from minutes to three years, preferably less than one year, while maintaining the requisite structural integrity.

By "exchange mechanism," as used herein, is meant a material or structure configured to substantially allow or inhibit a flow of material from a first element to a second element including fenestrated walls, permeable membranes, permeable walls, porous walls, porous membranes, perforations, and the like.

By "diameter," as used herein, is meant to be inclusive of equivalent characteristic lengths including hydraulic diameters of non-circular structures.

By "flush," as used herein, is meant as a surface of a first element and a coplanar surface of a second element to have a distance, or level, separating the first element and the second element to be within a tolerance of 0 µm, within a tolerance of 5 µm, within a tolerance of 10 µm, within a tolerance of 20 µm, or within a tolerance of 100 µm.

By "direct flow," as used herein, is meant as a transfer or a flow of at least one substance or material from a first element to at least a second element.

By "indirect flow," as used herein, is meant as an exchange or flow of at least one substance or material from a first element to at least a second element which is mediated by an exchange mechanism.

By "natural manner," as used herein, is meant a process or development as found in a nature.

By "polymer," as used herein, is meant to include polymers and monomers that can be polymerized or adhered to form an integral unit. The polymer can be non-biodegradable or biodegradable, typically via hydrolysis or enzymatic cleavage.

By "subsequent channel," as used herein, is meant, for a given channel, a channel which material flows therefrom. Accordingly, by "preceding channel," as used herein, is meant, for the given channel, a channel which material flows thereto.

By "rigid," as used herein, is meant a material that is stiff and does not deform easily. By "elastomeric," as used herein, is meant a material or a composite material that is not rigid as defined herein.

Additionally, the terms "client," "patient," "subject," and "user" are used interchangeably herein unless expressly stated otherwise.

A "disease" is a state of health of an animal wherein the animal cannot maintain homeostasis, and wherein if the disease is not ameliorated then the animal's health continues to deteriorate. In an exemplary embodiment, the device of the invention is implanted into a subject afflicted with a disease and in treatment thereof by means of such implantation.

"Amino Acid," as used herein refers to the genus encompassing hydrophilic amino acids, acidic amino acids, basic amino acids, polar amino acids, hydrophobic amino acids, aromatic amino acids, non-polar amino acids and aliphatic amino acids, including the genus and the species therein. A "peptide" is formed from such amino acids linked via peptide bonds. Amino acids also encompass amino-carboxylic acid species other than «-amino acids, e.g., aminobutyric acid (aba), aminohexanoic acid (aha), aminomethylbenzoic acid (amb) etc. In an exemplary embodiment, the cyanine dye of the invention is conjugated to a carrier molecule through a linker having one or more than one amino acid. Exemplary amino acids of use in such linkers include lysine, proline and acidic amino acids.

"Activated derivatives of carboxyl moieties," and equivalent species, refers to moiety on a precursor component of a conjugate of the invention (e.g., dye, adaptor, linker, polyvalent moiety) having a leaving group, e.g., an active ester, acyl halide, acyl imidazole, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e., $C_1$-$C_{10}$ means one to ten carbons).

Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, optionally, those derivatives of alkyl defined in more detail below, such as "alkenyl", "alkynyl", "alkyldiyl", "alkyleno" and "heteroalkyl."

"Alkenyl", refers to an unsaturated branched, straight-chain or cyclic alkyl radical having at least one carbon-carbon double bond derived by the removal of one hydrogen atom from a single carbon atom of a parent alkane. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc., and the like. In exemplary embodiments, the alkenyl group is ($C_2$-$C_6$) alkenyl.

"Alkynyl" refers to an unsaturated branched, straight-chain or cyclic alkyl radical having at least one carbon-carbon triple bond derived by the removal of one hydrogen atom from a single carbon atom of a parent alkene. Typical alkynyl groups include, but are not limited to, ethynyl; propynyls such as prop-1-yn-1-yl, prop-2-yn-1-yl, etc.; butynyls such as but-1-yn-1-yl, but-3-yn-1-yl, etc., and the like. In exemplary embodiments, the alkynyl group is ($C_2$-$C_6$) alkynyl.

"Alkyldiyl," refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,3-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In preferred embodiments, the alkyldiyl group is ($C_2$-$C_6$) alkyldiyl. Also preferred are saturated acyclic alkanyldiyl radicals in which the radical centers are at the terminal carbons, e.g., methandiyl (methano); ethan-1,2-diyl(ethano); propan-1,3-diyl(propano); butan-1,4-diyl(butano), and the like (also referred to as alkylenos, defined infra).

"Alkyleno," refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop [1]eno, propa [1,2]dieno, prop [1]yno, etc.; butylenos such as butano, but [1]eno, but [2]eno, buta [1,3]dieno, but [1]yno, but [2]yno, but [1,3]diyno, etc., and the like. Where specific levels of saturation are intended, the nomenclature alkano, alkeno and/or alkyno is used. In preferred embodiments, the alkyleno group is ($C_2$-$C_6$) alkyleno.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P and S, and wherein the nitrogen and sulfur atoms may optionally be oxidized and the nitrogen heteroatom may optionally be quaternized. The heteroatom(s) O, N, S, P and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula-C(O)$_2$R'-represents both-C(O)$_2$R'-and-R'C(O)$_2$—.

The terms "cycloalkyl" and "heterocycloalkyl," by themselves or in combination with other terms, represent, unless otherwise stated, cyclic versions of "alkyl" and "heteroalkyl," respectively. Also included are di- and multi-valent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$) alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes aryl and, optionally, heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy) propyl, and the like).

Each of the above terms (e.g., "alkyl," "heteroalkyl," "aryl," and "heteroaryl") include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O) R', —C(O) R', —CO$_2$R', —CONR'R", —OC(O) NR'R", —NR"C(O) R', SO$_3$R', —NR'—C(O) NR"R'", —NR"C(O)$_2$R', —NR—C(NR'R"R'")=NR"", —NR—C(NR'R")=NR", —S(O) R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. Accordingly, from the above discussion of substituents, one of skill in the art will understand that the terms "substituted alkyl" and "heteroalkyl" are meant to include groups that have carbon atoms bound to groups other than hydrogen atoms, such as haloalkyl (e.g., —CF$_3$ and —CH$_2$CF$_3$) and acyl (e.g., —C(O) CH$_3$, —C(O) CF$_3$, —C(O) CH$_2$OCH$_3$, and the like).

The substituents set forth in the paragraph above are referred to herein as "alkyl group substituents."

Similar to the substituents described for the alkyl radical, substituents for the aryl and heteroaryl groups are varied and are selected from, for example: halogen, —OR', =O, =NR', =N—OR', —NR'R", —SR',-halogen, —SiR'R"R'", —OC(O) R', —C(O) R', —CO$_2$R', —CONR'R", —OC(O) NR'R", —NR"C(O) R', —NR'—C(O) NR"R'", —NR"C(O)$_2$R', —NR—C(NR'R")=NR'", —S(O) R', —S(O)$_2$R', SO$_3$R', —S(O)$_2$NR'R", —NRSO$_2$R', —CN and —NO$_2$, —R', —N$_3$, —CH(Ph)$_2$, fluoro (C$_1$-C$_4$) alkoxy, and fluoro (C$_1$-C$_4$) alkyl, in a number ranging from zero to the total number of open valences on the aromatic ring system; and where R', R", R'" and R"" are preferably independently selected from hydrogen, (C$_1$-C$_8$) alkyl and heteroalkyl, unsubstituted aryl and heteroaryl, (unsubstituted aryl)-(C$_1$-C$_4$) alkyl, and (unsubstituted aryl)oxy-(C$_1$-C$_4$) alkyl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently -NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$) alkyl.

The substituents set forth in the two paragraphs above are referred to herein as "aryl group substituents."

A "linkage fragment" is a bond, or is a group that is formed by reaction of two reactive functional groups of complementary reactivity. An exemplary linkage fragment is an amide formed by the reaction of an amine and an activated derivative of a carboxylic acid (e.g., acyl halide, acyl imidazole, active ester, etc.). When the cyanine dyes of the invention are conjugated to a carrier molecule, they can be conjugated directly through a linkage fragment or through a linker that includes one or more linkage fragment. For example, a conjugate in which the dye is bound to a carrier molecule through a linker optionally includes a linkage fragment joining the linker and the dye and/or joining the linker and the carrier molecule.

The term "Linker" or "L", as used herein, refers to a single covalent bond or a series of stable covalent bonds incorporating 1-40, e.g., 10-30 nonhydrogen atoms selected from the group consisting of C, N, O, S and P that covalently attach the fluorogenic or fluorescent compounds to another moiety such as a chemically reactive group or a biological or non-biological component, e.g., a carrier molecule. Exemplary linkers include one or more linkage fragment, e.g., —C(O) NH—, —C(O)O—, —NH—, —S—, —O—, joining the dye to the linker and/or the linker to the carrier molecule and the like. Linkers are also of use to join the cyanine nucleus component of the compound to a reactive functional group, or a component of a reactive functional group.

As used herein, "fluorophore" refers to a fluorescent species.

"Moiety" refers to the radical of a molecule that is attached to another moiety.

Furthermore, when a reference number is given an "ith" denotation, the reference number refers to a generic component, set, or embodiment. For instance, a graphical icon termed "graphical icon i" refers to the ith graphical icon in a plurality of graphical icons (e.g., a graphical icon 616-*i* in a plurality of graphical icons 616).

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

In the present disclosure, unless expressly stated otherwise, descriptions of devices and systems will include implementations of one or more computers. For instance, and for purposes of illustration in FIG. 1, a client device (e.g., client device 400 of FIG. 4) is represented as single device that includes all the functionality of the client device 400. However, the present disclosure is not limited thereto. For instance, the functionality of the client device 400 may be spread across any number of networked computers and/or reside on each of several networked computers and/or by hosted on one or more virtual machines and/or containers at a remote location accessible across a communications network (e.g., communications network 106). One of skill in the art will appreciate that a wide array of different computer topologies is possible for the client device 400, and other devices and systems of the preset disclosure, and that all such topologies are within the scope of the present disclosure.

FIG. 1 depicts a block diagram of a distributed client-server system (e.g., distributed client-server system 100) according to some embodiments of the present disclosure. The system 100 facilitates fabricating a microchannel vascular network device (e.g., microchannel vascular network device 700-1 of FIG. 7, microchannel vascular network device 700-2 of FIG. 14, etc.). Furthermore, the system 100 facilitates seeding and culturing a plurality of cells within the microchannel vascular network device 700. In the way, the present disclosure provides systems and methods for fabricating and seeding cells within a microchannel vascular network device 700, that otherwise was not previously feasible.

Of course, other topologies of the system 100 are possible. For instance, in some embodiments, any of the illustrated devices and systems can in fact constitute several computer systems that are linked together in a network, or be a virtual machine or container in a cloud-computing environment. Moreover, rather than relying on a physical communications network 106, the illustrated devices and systems may wirelessly transmit information between each other. As such, the exemplary topology shown in FIG. 1 merely serves to describe the features of an embodiment of the present disclosure in a manner that will be readily understood to one of skill in the art.

Referring to FIG. 1, in some embodiments, a distributed client-server system 100 includes a fabrication system 200 for facilitating the fabrication of a microchannel vascular network device 700, a bioreactor system 200 for facilitating a culturing of cells within the microchannel vascular network device 700, and one or more client devices 400 (e.g., a first client device 400-1), hereinafter "client device,"

In some embodiments, the communication network 106 optionally includes the Internet, one or more local area networks (LANs), one or more wide area networks (WANs), other types of networks, or a combination of such networks.

Examples of communication networks 106 include the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VOIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Now that a distributed client-server system 100 has generally been described, an exemplary fabrication system 200 for fabricating a microchannel vascular network device 700 will be described with reference to FIG. 2.

In various embodiments, the fabrication system 200 includes one or more processing units (CPUs) 202, a network or other communications interface 204, and memory 212.

Memory 212 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. Memory 212 may optionally include one or more storage devices remotely located from the CPU(s) 202. Memory 212, or alternatively the non-volatile memory device(s) within memory 212, includes a non-transitory computer readable storage medium. Access to memory 212 by other components of the fabrication system 200, such as the CPU(s) 202, is, optionally, controlled by a controller. In some embodiments, memory 212 can include mass storage that is remotely located with respect to the CPU(s) 202. In other words, some data stored in memory 212 may in fact be hosted on devices that are external to the system 200, but that can be electronically accessed by the fabrication system 200 over an Internet, intranet, or other form of network 106 or electronic cable using communication interface 204.

In some embodiments, the memory 212 of the fabrication system 200 for generating a microchannel vascular network device 700 stores:

- an operating system 216 (e.g., ANDROID, IOS, DARWIN, RTXC, LINUX, UNIX, OS X, WINDOWS, or an embedded operating system such as VxWorks) that includes procedures for handling various basic system services;
- an electronic address 218 associated with the fabrication system 200 that identifies the fabrication system 200;
- a design control module 220 for forming a respective microchannel vascular network device based one or more design criteria 230;
- a design storage 240 for storing a plurality of designs 240, each of which is associated with a corresponding microchannel vascular network device; and a fabrication module 260 for facilitating a fabrication of a microchannel vascular network device.

An electronic address 218 is associated with the system 200, which is utilized to at least uniquely identify the system 200 from other devices and components of the distributed system 100. For instance, in some embodiments, the electronic address 218 is utilized to receive a request from a client device 300.

A design control module 220 includes a plurality of design criteria 230, which for a basis for fabricating a respective microchannel vascular network device. For instance, in some embodiments, a respective design criterion 230 in the plurality of design criteria 230 is associated with a parameter of the microchannel vascular network device (e.g., a length of the microchannel vascular network device, a porosity of a material forming the microchannel vascular network device, etc.), a parameter of the fabrication system 200 (e.g., a resolution of the fabrication system 200, etc.), or both. In some embodiments, the plurality of design criteria 230 include one or more predetermined design criteria. In some embodiments, a predetermined design criteria includes a predetermined range of selections for a subject to choose from in fabrication a microchannel vascular network device. In this way, the subject is preventing from selecting a design criteria that is outside a functional embodiment of a microchannel vascular network device 700.

For instance, in some embodiments the plurality of design criteria are utilized and/or based from empirical parameters used to model a flow within a respective microchannel device. For instance, in some embodiments, the plurality of design criteria include a plurality of flow design criteria including a flow rate, a diffusion rate, or both (e.g., a diffusion rate during flow and/or a diffusion rate without flow).

A design storage 240 retains one or more microchannel vascular network devices designs 250. Each respective design 250 includes a respective selection of one or more design criteria 230. In this way, a subject can select a design 250 from the design 240 without having to individually select respective design criteria 230 in order to fabricate a microchannel vascular network device 700. For instance, in some embodiments, a subject determines a respective plurality of design criteria 230 to fabricate a corresponding microchannel vascular network. Accordingly, in response to determine a respective plurality of design criteria 230, the fabrication system 200 can retain a corresponding device design 250 that is associated with the corresponding microchannel vascular network. Thus, the subject can fabricate a plurality of the corresponding microchannel vascular network without having to determine the design criteria for each instance of the fabricating.

For instance, in some embodiments, the one or more device designs 250 includes a predetermined microchannel vascular network device design 250 that is configured for a candidate subject. As a non-limiting example, in some embodiments, a first microchannel vascular network device design is configured for a first mammalian candidate subject, and a second microchannel vascular network device design is configured for a second mammalian candidate subject. In some embodiments, the first mammalian candidate subject and the second mammalian candidate subject are the same species of mammalian (e.g., both are configured for a human mammalian candidate subject, both are configured for a rat mammalian candidate subject, etc.). Furthermore, in some embodiments, the first mammalian candidate subject and the second mammalian candidate subject are the same species of mammalian but are different candidate subjects (e.g., the first candidate subject is a first human and the second candidate subject is a second human different than the first human). However, the present disclosure is not limited thereto. For instance, in some embodiments, the first the first mammalian candidate subject and the second mammalian candidate subject belong to different species of and/or a different genus of mammals.

As another non-limiting examples, in some embodiments, the device designs 250 include one or more devices designs that is associated with an in vivo implementation, and one or more device designs that is associated with an in vitro implementation. For instance, in some embodiments, a first device design 250-1 is associated with a first microchannel vascular network device including a first plurality of design criteria 230 associated with a first channel, a second channel, and a structure interposing between the first and second channels, a layer thickness of 50 μm, an exposure time of 2 seconds, a first layer time scale factor (FLTSF) of about 2× to about 4×, and a fabrication time of about 48 minutes. In some embodiments, a second device design 250-2 is associated with a second microchannel vascular network device including a second plurality of design criteria 230 associated with a first channel, a second channel, and a structure interposing between the first and second channels, a layer thickness of 100 μm, an exposure time of 4 seconds, an FLTSF of about 2× to about 4×, and a fabrication time of about 24 minutes. In some embodiments, a third device design 250-3 is associated with a third microchannel vascular network device including a third plurality of design criteria 230 associated with a first channel, a second channel, and a structure interposing between the first and second channels, a layer thickness of 100 μm, an exposure time of 4 seconds, an FLTSF of about 4× to about 8×, and a fabrication time of about 72 minutes to about 77 minutes. In some embodiments, the third device design 250-3 is associated with a rat mammalian candidate subject.

The fabrication system 200 includes a fabrication module 260 that facilitates controlling a mechanism for fabricating a microchannel vascular network device. For instance, in some embodiments, the fabrication module communications one or more instructions to the mechanism, which, in response to the one or more instructions, traverses a region and conducts a fabrication of the microchannel vascular network device. As a non-limiting example, consider a fabrication system 200 including a vat photopolymerization mechanism. Accordingly, the fabrication module 260 communications one or more instructions to the vat photopolymerization mechanism associated with an intensity of light associated with the vat photopolymerization mechanism, an exposure time of light associated with the vat photopolymerization mechanism, a supply of a pre-polymer solution of the vat photopolymerization mechanism, a supply of a photoinitiator associated with the vat photopolymerization mechanism, and the like.

Each of the above identified modules and applications correspond to a set of executable instructions for performing one or more functions described above and the methods described in the present disclosure (e.g., the computer-implemented methods and other information processing methods described herein; method 500 of FIG. 5; method 600 of FIG. 6; etc.). These modules (e.g., sets of instructions) need not be implemented as separate software programs, procedures or modules, and thus various subsets of these modules are, optionally, combined or otherwise rearranged in various embodiments of the present disclosure. In some embodiments, the memory 212 optionally stores a subset of the modules and data structures identified above.

Furthermore, in some embodiments, the memory 212 stores additional modules and data structures not described above.

Figure 2:
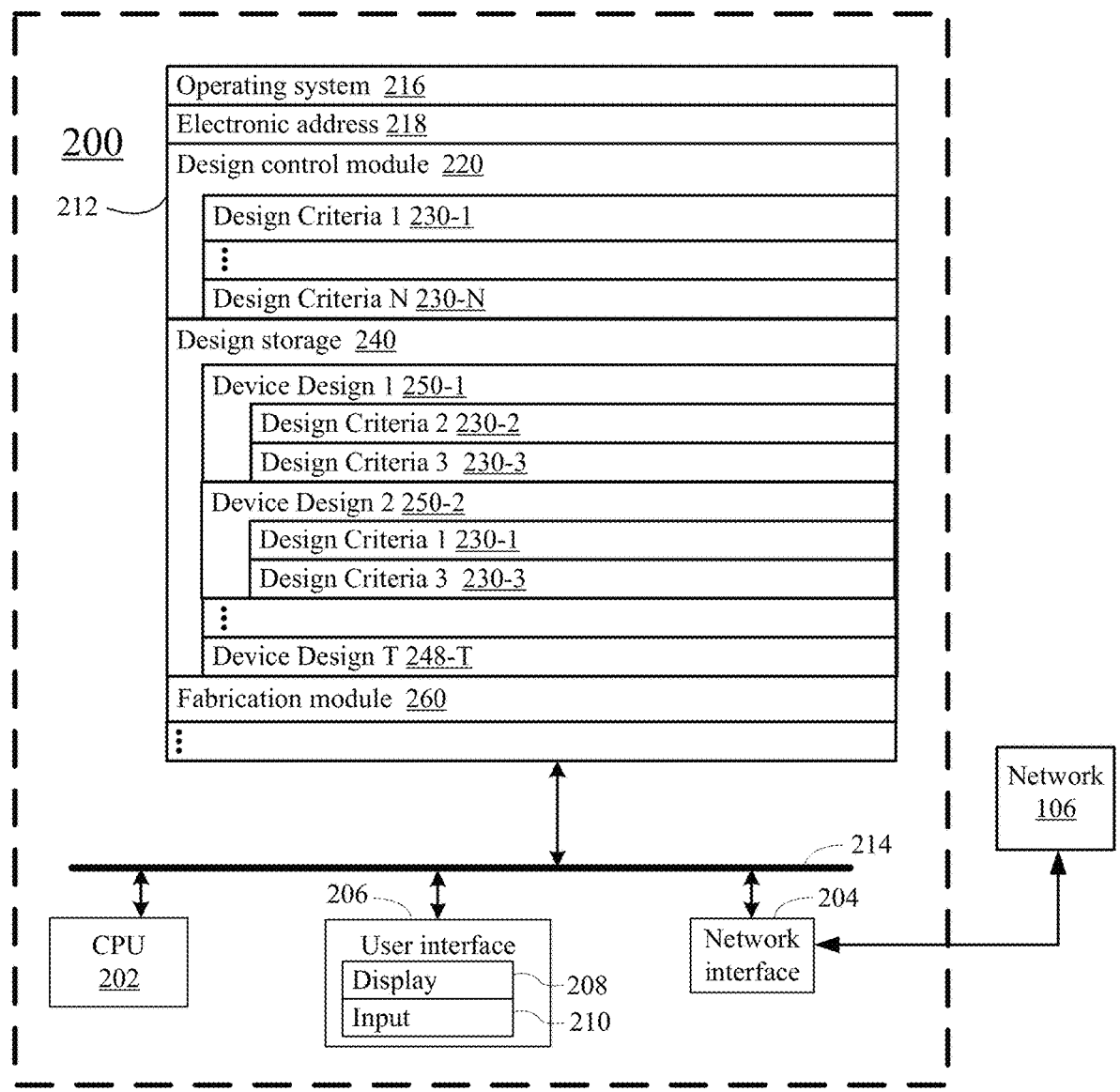
FIG. 2 illustrates a fabrication system for fabricating a microchannel vascular network device, in accordance with embodiments of the present disclosure.

It should be appreciated that the fabrication system 200 of FIG. 2 is only one example of an fabrication system 200, and that the fabrication system 200 optionally has more or fewer components than shown, optionally combines two or more components, or optionally has a different configuration or arrangement of the components. The various components shown in FIG. 2 are implemented in hardware, software, firmware, or a combination thereof, including one or more signal processing and/or application specific integrated circuits.

Figure 3:
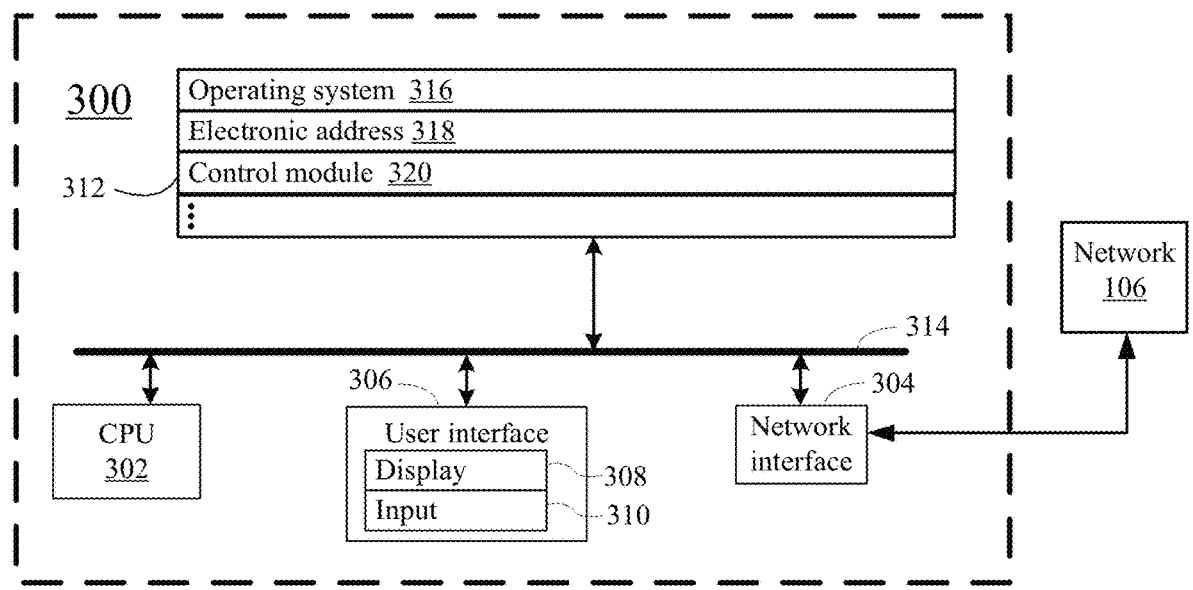
FIG. 3 illustrates a bioreactor system for controlling flow through a microchannel device, in accordance with embodiments of the present disclosure.

Referring to FIG. 3, in various embodiments, the present disclosure includes a bioreactor system 300. The bioreactor system 300 includes one or more processing units (CPUs) 302, a network or other communications interface 304, and memory 312.

Memory 312 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. Memory 312 may optionally include one or more storage devices remotely located from the CPU(s) 202. Memory 312, or alternatively the non-volatile memory device(s) within memory 312, includes a non-transitory computer readable storage medium. Access to memory 312 by other components of the bioreactor system 300, such as the CPU(s) 302, is, optionally, controlled by a controller. In some embodiments, memory 312 can include mass storage that is remotely located with respect to the CPU(s) 302. In other words, some data stored in memory 312 may in fact be hosted on devices that are external to the bioreactor system 300, but that can be electronically accessed by the bioreactor system 300 over an Internet, intranet, or other form of network 106 or electronic cable using communication interface 304.

In some embodiments, the memory 312 of the bioreactor system 300 for culturing a plurality of cells within a microchannel vascular network device 700 stores:
an operating system 316 (e.g., ANDROID, IOS, DARWIN, RTXC, LINUX, UNIX, OS X, WINDOWS, or an embedded operating system such as VxWorks) that includes procedures for handling various basic system services;
an electronic address 318 associated with the bioreactor system 300 that identifies the bioreactor system 300; and
a control module for controlling one or more system parameters of the bioreactor system 300.

An electronic address 318 is associated with the bioreactor system 300, which is utilized to at least uniquely identify the system 300 from other devices and components of the distributed system 100. For instance, in some embodiments, the electronic address 318 is utilized to receive a design of a microchannel vascular network device 700 from a client device 400.

A control module 320 facilitates communicating one or more instructions to a component of the bioreactor system 300. For instance, in some embodiments, the bioreactor system 300 includes a pump (e.g., pump 1720 of FIG. 17) and/or one or more reservoirs (e.g., reservoir(s) 1710 of FIG. 17), whose operation is controlled through the control module 320. For instance, in some embodiments, the control module 320 controls a flow rate of the bioreactor system 300.

Figure 17A:
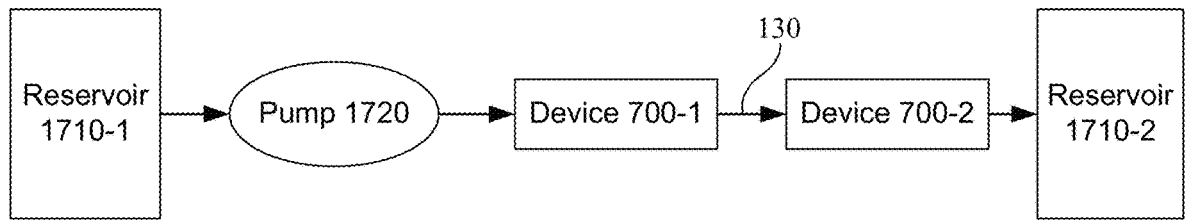
FIG. 17A illustrates a bioreactor system including a first microchannel vascular network device and a second microchannel vascular network device coupled in series, in accordance with an embodiment of the present disclosure.
Figure 17B:
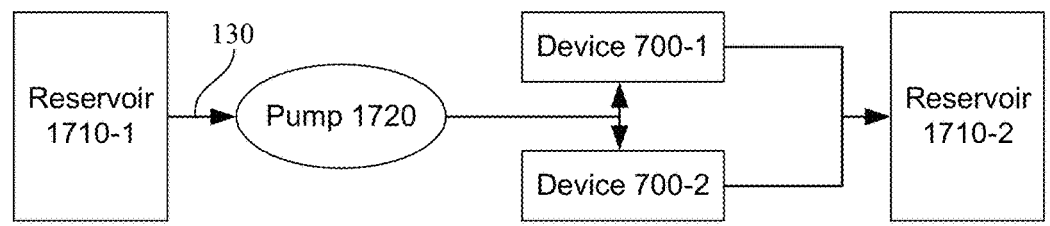
FIG. 17B illustrates a bioreactor system including a first microchannel vascular network device and a second microchannel vascular network device coupled in parallel, in accordance with an embodiment of the present disclosure.
Figure 17C:
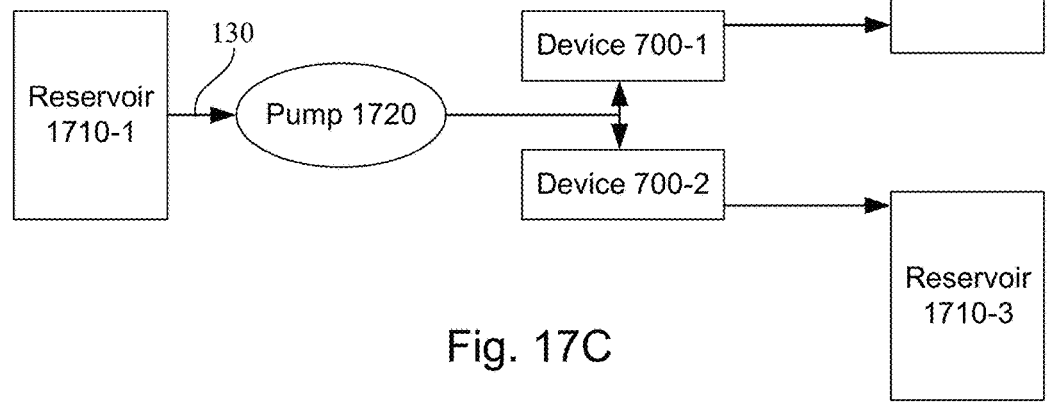
FIG. 17C illustrates a bioreactor system including a first microchannel vascular network device and a second microchannel vascular network device coupled in parallel, in accordance with an embodiment of the present disclosure.

Referring briefly to FIGS. 17A, 17B, and 17C, various arrangements a bioreactor system 300 including one or more devices microchannel vascular network devices 700 in the bioreactor system 300 are illustrated. For instance, the system of FIG. 17A illustrates an embodiment in which first device 700-1 and second device 700-2 are coupled in series such that medium 130 is drawn from by the pump from first reservoir 1720-1 through the first device, through the second device, and collected by second reservoir 1720-2. Accordingly, cells accommodated by second device 700-2 are subjected to material output from first device 700-1 (e.g., waste material), in order to determine how the material output from the first device effects the cells of the second device. This determining is useful as a component of toxicity assays a wide array of compounds, including pharmaceutical composition, unknown substances, putative toxins, known toxins, agents of war, or the like. Similarly, FIG. 17B illustrates an embodiment of a bioreactor system in which first device 700-1 and second device 700-2 are coupled in parallel, such that medium 130 is drawn by the pump from first reservoir 1720-1 and diverges to flow through the first device and through the second device, which is in turn collected by second reservoir 1720-2. Such a configuration as illustrated in FIG. 17B can be used to test how conditions of medium 130 effect different cells stored in the respective devices 700 (e.g., determine how a pharmaceutical composition included in medium 130 effects a first cell of a first device and a second cell of a second device simultaneously). Referring to FIG. 17C, in some embodiments, one or more devices 700 of the bioreactor system is allocated a respective reservoir 1720. For instance, in some embodiments, each device 700, or a subset of devices, is provided a dedicated reservoir 1720 that collects medium 130 output by the respective device (e.g., output via the outlet of the channel or the outlet of the caplet of the respective device) in order to conduct testing on the collected medium (e.g., conducting a toxicity assay).

Figure 18A:
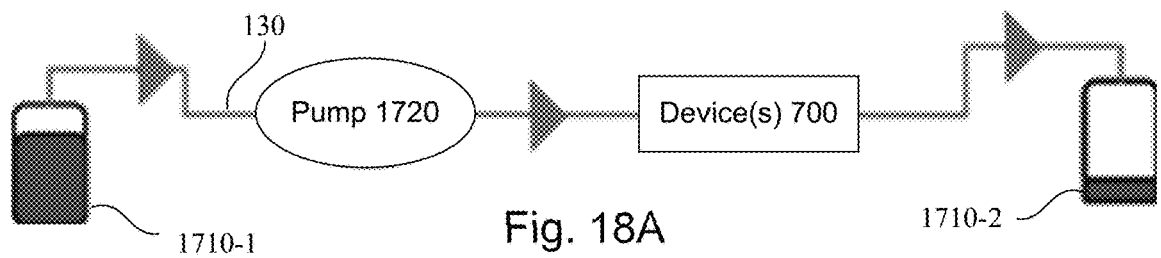
FIGS. 18A, 18B, 18C, and 18D illustrate various configurations of bioreactor systems, in accordance with embodiments of the present disclosure.
Figure 18B:
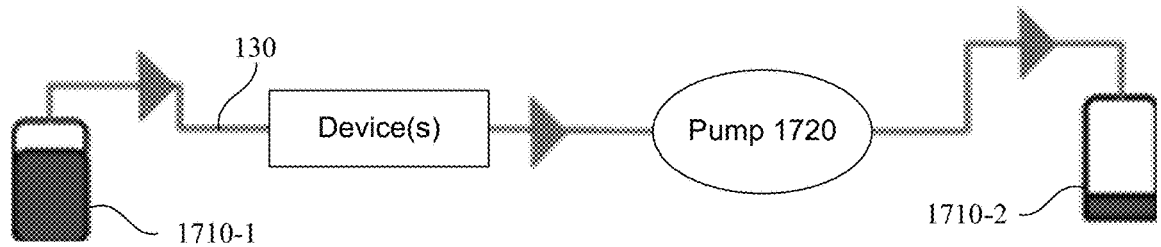
Figure 18C:
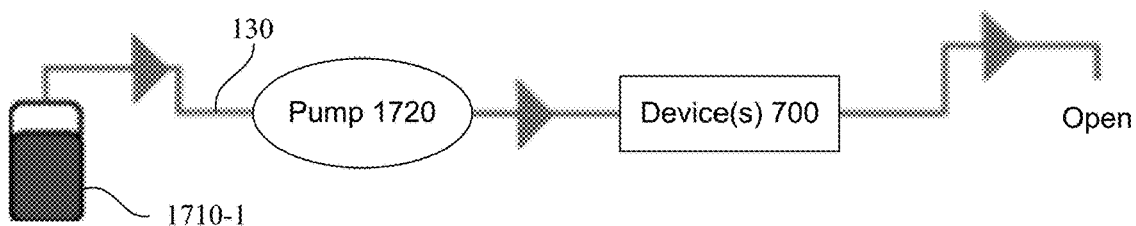
Figure 18D:
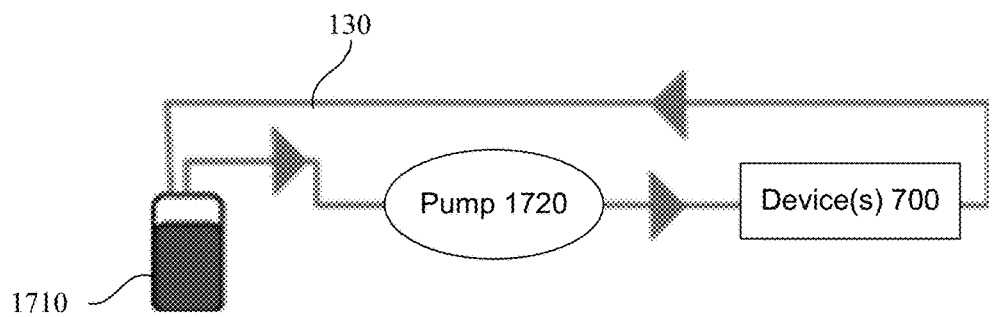

Referring to FIG. 18A through FIG. 18D, various embodiments of a bioreactor system and flow paths are illustrated. In the various systems of FIG. 18A through FIG. 18D, any useful configuration of devices (e.g., a plurality of devices in series, a plurality of devices in parallel, etc.) is represented by a portion of the bioreactor system indicated by "devices(s) 100." FIG. 18A illustrates an embodiment of a system in which reservoir 1720-1 supplies a flow of medium 130, which is collected by reservoir 1720-2 after flowing through the system. FIG. 18B illustrates a similar embodiment as depicted in FIG. 18A but instead utilizes pump 1720 to draw medium 130 through the system instead of pushing, or driving, the medium. FIG. 18C illustrates a bioreactor system in which a portion of an outlet of device(s) 700 is open (e.g., exposed to an external environment). In some embodiments, this open configuration is used to form a siphon type pressure differential or to collect medium 130 outside of a respective reservoir. Furthermore, FIG. 18D illustrates a bioreactor system in which a portion of an outlet of device(s) 700 is in communication with reservoir 200, thus forming a closed flow path for medium 130. In some embodiments, this closed configuration is used to determine an effect (e.g., exposure to medium 130) on cells of devices 700 over a period of time (e.g., medium 130 flows through the system continuously for a period of time).

While the systems of FIG. 17A through FIG. 18D each illustrate an arrangement including at least one reservoir, one skilled in the art will recognize that these systems are only exemplary and that the present disclosure include systems not utilizing a reservoir, or utilizing a plurality of reservoirs (e.g., a reservoir for each device of the system).

Each of the above identified modules and applications correspond to a set of executable instructions for performing one or more functions described above and the methods described in the present disclosure (e.g., the computer-implemented methods and other information processing methods described herein; method 500 of FIG. 5; method 600 of FIG. 6; etc.). These modules (e.g., sets of instructions) need not be implemented as separate software programs, procedures or modules, and thus various subsets of these modules are, optionally, combined or otherwise re-arranged in various embodiments of the present disclosure. In some embodiments, the memory 312 optionally stores a subset of the modules and data structures identified above. Furthermore, in some embodiments, the memory 312 stores additional modules and data structures not described above.

It should be appreciated that the bioreactor system 300 of FIG. 3 is only one example of a bioreactor system 300, and that the bioreactor system 300 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Figure 4:
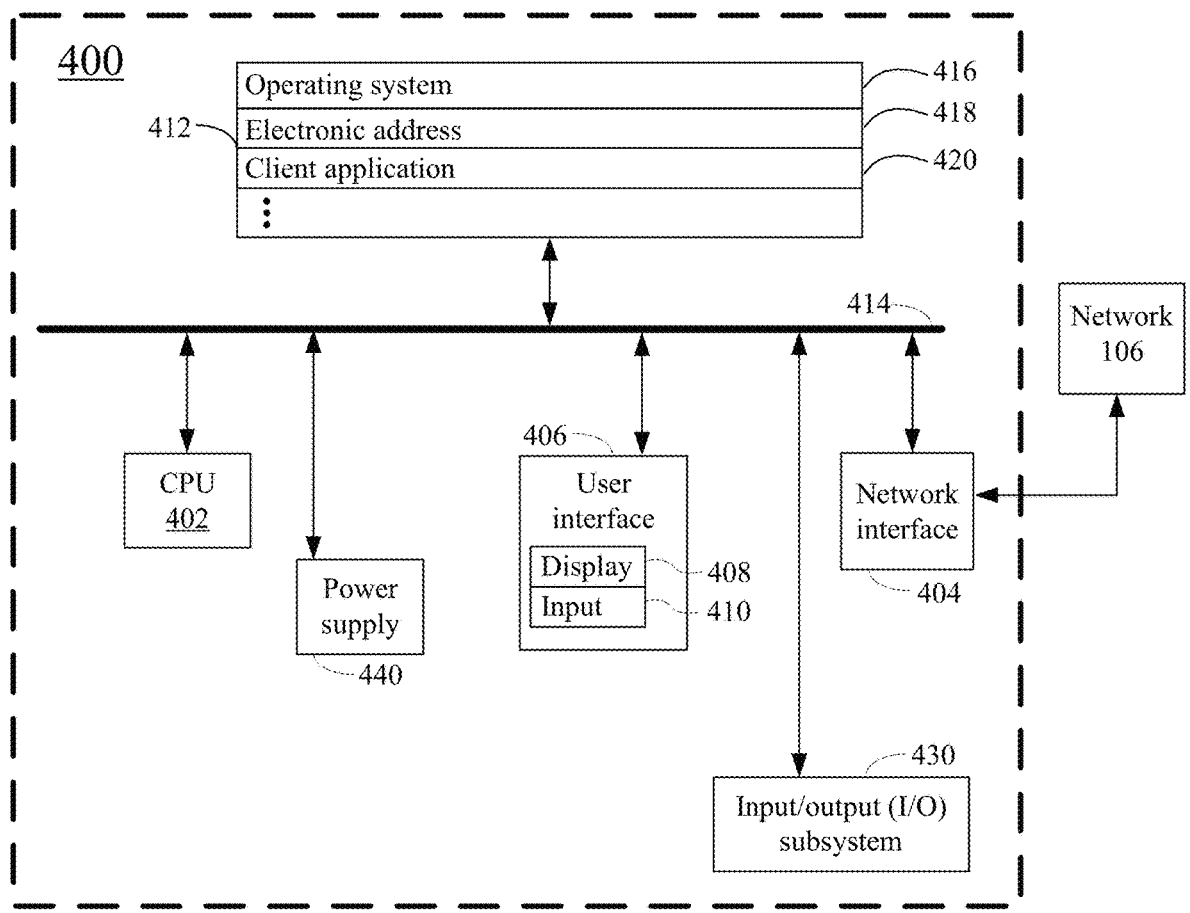
FIG. 4 illustrates a client device for designing and/or controlling a flow through a microchannel vascular network device, in accordance with embodiments of the present disclosure.

Referring to FIG. 4, an exemplary client device 400 is provided (e.g., first client device 400-1). A client device 400 includes one or more processing units (CPUs) 402, one or more network or other communication interfaces 404, memory 411 (e.g., random access memory and/or non-volatile memory) optionally accessed by one or more controllers, and one or more controllers, and one or more communication busses 414 interconnecting the aforementioned components.

In some embodiments, a client device 400 includes a mobile device, such as a mobile phone, a tablet, a laptop computer, a wearable device such as a smart watch, and the like. Alternatively, in some embodiments, the client device 400 is a desktop computer or other similar devices. Furthermore, in some embodiments, the client devices 400 (e.g. a first user device 300-1, a second user device 400-2, a third user device 400-3, etc.) communicate with a centralized client device 400 (e.g., a server client device 400) that facilitates communicating a design of a microchannel vascular network device 700 to the fabrication system 200.

In addition, the client device 400 includes a user interface 406. The user interface 406 typically includes a display device 408 for presenting media, such as a graphical user interface associated with a client application 420 and receiving instructions from the subject operating the client device 400. In some embodiments, the display device 408 is optionally integrated within the client device 400 (e.g., housed in the same chassis as the CPU 402 and memory 412), such as a smart (e.g., smart phone) device. In some embodiments, the client device 400 includes one or more input device(s) 410, which allow the subject to interact with the client device 400. In some embodiments, input devices 410 include a keyboard, a mouse, and/or other input mechanisms. Alternatively, or in addition, in some embodiments, the display device 408 includes a touch-sensitive surface, e.g., where display 408 is a touch-sensitive display or client device 400 includes a touch pad.

In some embodiments, the client device 400 includes an input/output (I/O) subsystem 430 for interfacing with one or more peripheral devices with the client device 400. For instance, in some embodiments, audio is presented through an external device (e.g., speakers, headphones, etc.) that receives audio information from the client device 400 and/or a remote device (e.g., fabrication system 200), and presents audio data based on this audio information. In some embodiments, the input/output (I/O) subsystem 430 also includes, or interfaces with, an audio output device, such as speakers or an audio output for connecting with speakers, earphones, or headphones. In some embodiments, the input/output (I/O) subsystem 430 also includes voice recognition capabilities (e.g., to supplement or replace an input device 410).

In some embodiments, the client device 400 also includes one or more sensors (e.g., an accelerometer, a magnetometer, a proximity sensor, a gyroscope, etc.), an image capture device (e.g., a camera device or an image capture module and related components), a location module (e.g., a Global Positioning System (GPS) receiver or other navigation or geolocation system module/device and related components), or a combination thereof, and the like.

Memory 412 includes high-speed random access memory, such as DRAM, SRAM, DDR RAM, or other random access solid state memory devices, and optionally also includes non-volatile memory, such as one or more magnetic disk storage devices, optical disk storage devices, flash memory devices, or other non-volatile solid state storage devices. Memory 412 may optionally include one or more storage devices remotely located from the CPU(s) 402. Memory 412, or alternatively the non-volatile memory device(s) within memory 412, includes a non-transitory computer readable storage medium. Access to memory 412 by other components of the client device 400, such as the CPU(s) 402 and the I/O subsystem 330, is, optionally, controlled by a controller. In some embodiments, memory 412 can include mass storage that is remotely located with respect to the CPU 402. In other words, some data stored in memory 412 may in fact be hosted on devices that are external to the client device 400, but that can be electronically accessed by the client device 400 over an Internet, intranet, or other form of network 106 or electronic cable using communication interface 404.

In some embodiments, the memory 412 of the client device 400 stores:
- an operating system 416 that includes procedures for handling various basic system services;
- an electronic address 418 associated with the client device that identifies the client device; and
- a client application 420 for generating content for display through a graphical user interface presented on the display 408 the client device 400.

An electronic address 418 is associated with the client device 400, which is utilized to at least uniquely identify the client device 400 from other devices and components of the distributed system 100. In some embodiments, the electronic address 418 associated with the client device 400 is used to determine a source of a communication received from and/or provided to the client device 400.

In some embodiments, a client application 420 is a group of instructions that, when executed by a processor (e.g., CPU(s) 402), generates content (e.g., a graphical user interface for selecting one or more design criteria of a microchannel vascular network device 700) for presentation to the subject. In some embodiments, the client application 420 generates content in response to one or more inputs received from the subject through the user interface 406 of the client device 400. For instance, in some embodiments, the client application 420 includes a media presentation application for viewing the contents of a file or web application.

Each of the above identified modules and applications correspond to a set of executable instructions for performing one or more functions described above and the methods described in the present disclosure (e.g., the computer-implemented methods and other information processing methods described herein; method 500 of FIG. 5; method 600 of FIG. 6; etc.). These modules (e.g., sets of instructions) need not be implemented as separate software programs, procedures or modules, and thus various subsets of these modules are, optionally, combined or otherwise rearranged in various embodiments of the present disclosure. In some embodiments, the memory 312 optionally stores a subset of the modules and data structures identified above. Furthermore, in some embodiments, the memory 312 stores additional modules and data structures not described above.

It should be appreciated that the client device 400 of FIG. 4 is only one example of a client device 400, and that the client device 400 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Now that a general topology of the distributed system 100 has been described in accordance with various embodiments of the present disclosures, details regarding some processes for fabricating a microchannel vascular network device in accordance with FIG. 5 will be described. FIG. 5 illustrates a first flow chart of methods (e.g., method 500) for fabricating a microchannel vascular network device 700 in accordance with embodiments of the present disclosure. In the flow charts, the preferred parts of the methods are shown in solid line boxes, whereas optional variants of the methods, or optional equipment used by the methods, are shown in dashed line boxes.

Various modules in the memory 212 of the fabrication detection system 200, the memory 412 of a client device 400, or both perform certain processes of the methods described in FIG. 5, unless expressly stated otherwise. Furthermore, it will be appreciated that the processes in FIG. 5 can be encoded in a single module or any combination of modules.

Block 502. Referring to block 502 of FIG. 5, a method 500 includes determining, based on a plurality of design criteria (e.g., design criteria 230 of FIG. 2), a microchannel vascular network design (e.g., device design criteria 250 of FIG. 2) for a microchannel vascular network device (e.g., microchannel vascular device 700 of FIG. 7).

Figure 7:
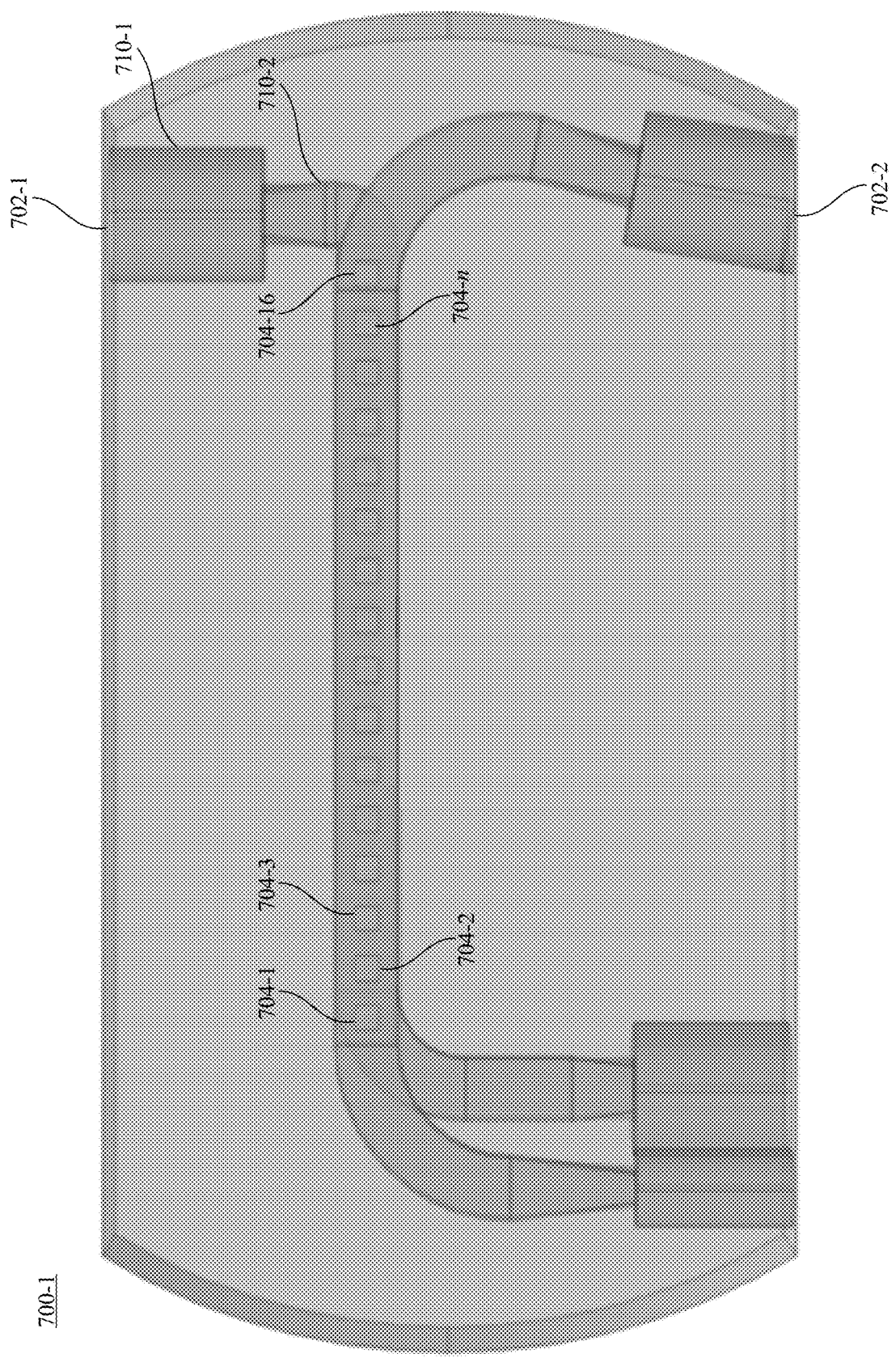
FIG. 7 illustrates a view of an exemplary microchannel device in accordance with embodiments of the present disclosure.

The microchannel vascular network design includes a first channel network (e.g., first channel network 702-1 of FIG. 7) and a second microchannel network based on the first channel network (e.g., first channel network 702-1 of FIG. 7).

In some embodiments, a structure (e.g., structure 704 of FIG. 7) for providing fluidic communication through between the first channel network and the second channel network is provided interposing between the first channel network and the second channel network. In some embodiments, the structure is a material (e.g., the polymer material) of the microchannel vascular network device. In other embodiments, the structure includes a membrane. In some embodiments, the structure includes one or more intermediate channels interposing between the first channel network and the second channel network.

As a non-limiting example, referring to FIG. 25 through FIG. 27 and FIGS. 37 and 38, in some embodiments, a respective microchannel vascular design is associated with a candidate subject of a mammalian rat. Accordingly, the respective microchannel vascular design is configured to form a microchannel vascular network device having a first channel network configured as a hepatic vein (HB) and the second channel network is configured as a portal vein (PV). A structure is formed interposing between the first channel network and the second channel network, which allows for fluidic communication between the first channel network and the second channel network. In some embodiments, the fluidic communication between the first channel network and the second channel network. In some embodiments, the structure includes one or more intermediate channels, which are configured to trade a mechanism inside an internal structure of the one or more intermediate channels. Here, the respective microchannel vascular design fabricates a microchannel vascular network device with a length of 31 millimeters (mm) (e.g., y-axis length), a width of 11.4 mm (e.g., x-axis length), and a height of 11 mm (e.g., z-axis depth). Each of the first channel network and the second channel network includes a respective diameter.

In some embodiments, the structure includes a first end portion in communication with the first channel network with the first end portion including a first diameter, and a second end portion in communication with the second channel network with the second end portion including a second diameter. Moreover, the first diameter and the second diameter of the structure define an interior transition region of the structure.

In some embodiments, the first diameter is different from the second diameter. For instance, in some embodiments, the first diameter is from about 992 microns (μm) to about 623 μm, and the second diameter is from about 832 μm to about 553 μm. In some embodiments, the first diameter and/or the second diameter is from about 1,000 μm to about 399 μm. In some embodiments, the first diameter and/or the second diameter from about 900 μm to about 199 μm.

Figure 30A:
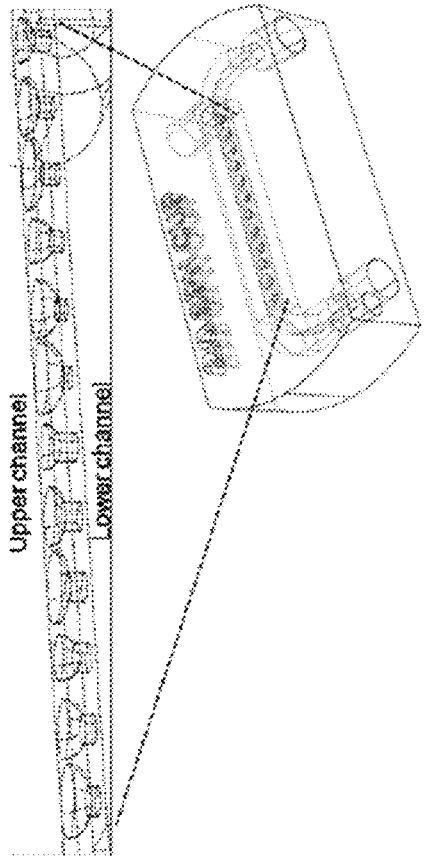
Figure 30B:
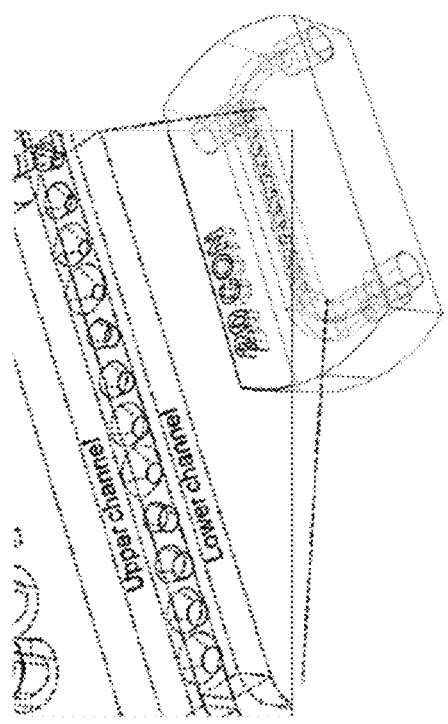
Figure 30C:
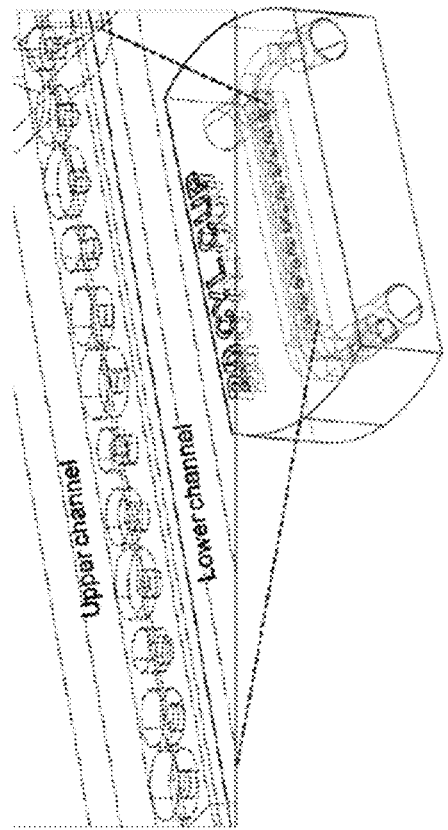
Figure 30D:
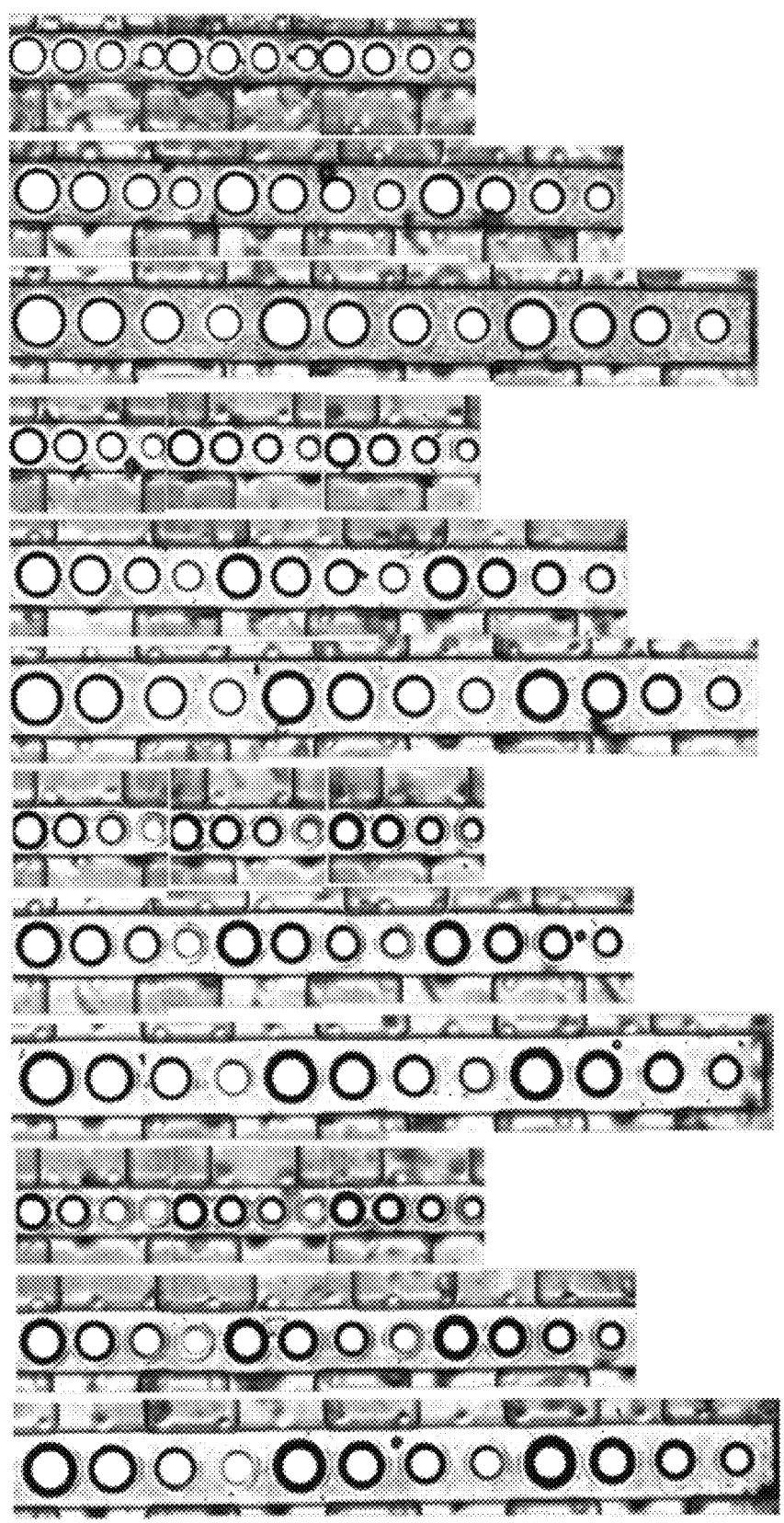
Figure 32:
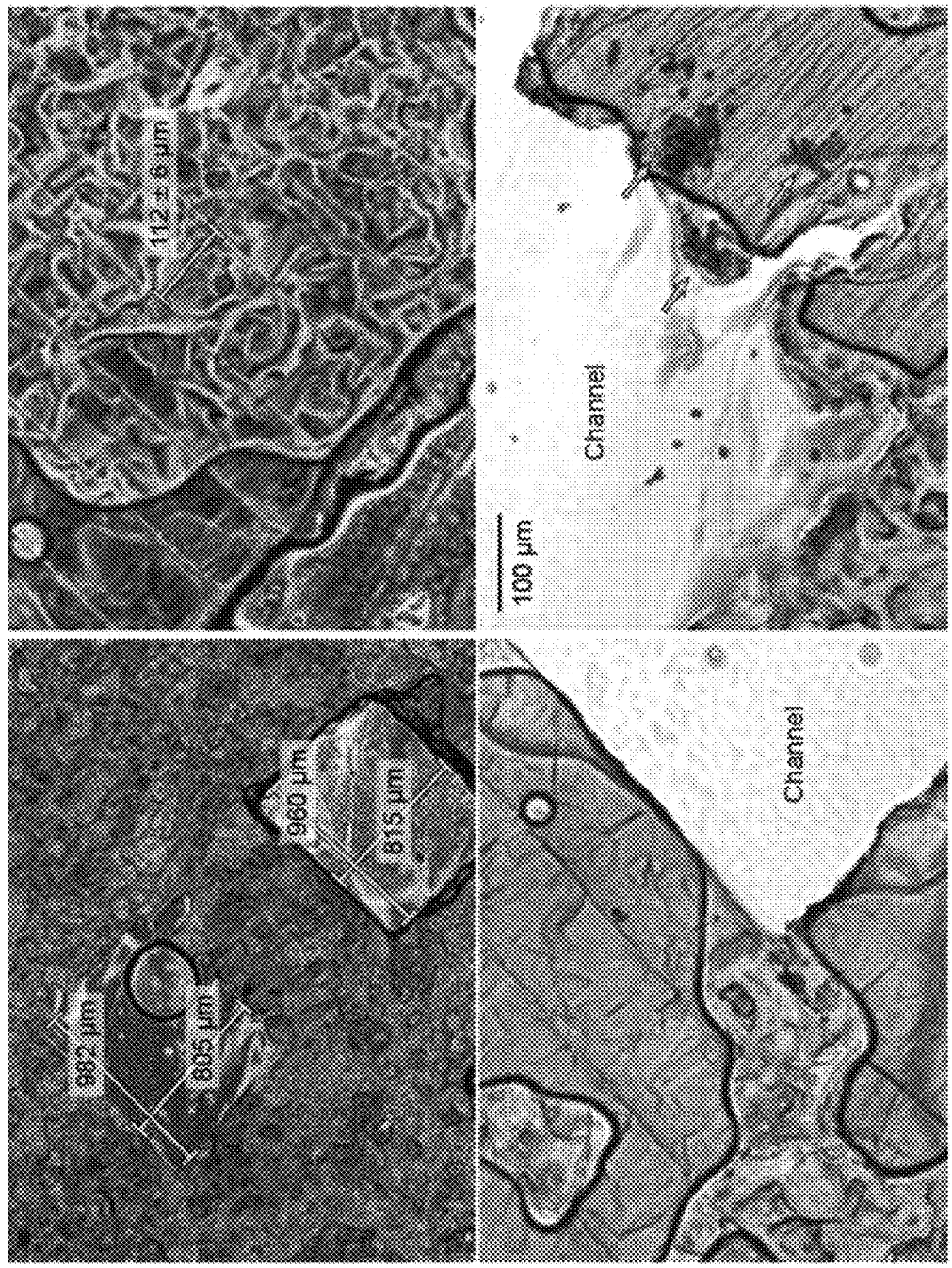

In some embodiments, the interior transition region of the structure includes an interior surface define by revolving a continuous, smooth curve about an axis of the structure. In some embodiments, the continuous, smooth curve comprises a conical shape, an ellipsoidal shape, or a cylindrical shape. As a non-limiting example, FIG. 30A illustrates a plurality of structures, each having an interior transition region in a conical shape. FIG. 30B illustrates a plurality of structures, each having an interior transition region in a cylindrical shape. Moreover, FIG. 30C illustrates a plurality of structures, each having an interior transition region in an ellipsoid shape. For instance, referring to FIG. 30D, a plurality of structures including a conical shape smooth continuous curve are provided, in which a range of a respective diameter is from about 1000 μm to about 573 μm. Referring briefly to FIG. 32, a cross section of a respective microchannel vascular network device is provided, in which a first structure includes a corresponding diameter from about 982 μm to about 805 μm and a second structure includes a corresponding diameter from about 960 μm to about 815 μm.

In some embodiments, the interior transition region of the structure includes an interior surface define by a monotonic function. In some embodiments, the monotonic function is a linear function (e.g., a truncated cone), a square root function, or a logarithmic function.

In some embodiments, the interior transition region of the structure includes a corresponding length from about 399 μm to about 701 μm. Accordingly, this length allows for an exchange of a medium between the first channel network and the second channel network without deteriorating an aspect of the medium.

In some embodiments, a length defined from a first end portion to a second end portion of the microchannel vascular network device is from about 15 centimeters (centimeters) to about 7.5 cm.

In some embodiments, the plurality of design criteria comprise one or more length design criteria, one or more mass design criteria, one or more temporal design criteria, one or more polymer design criteria, one or more temporal design criteria, one or more illuminance design criteria, or a combination thereof.

For instance, in some embodiments, the one or more design criteria include a molecular weight of a pre-polymer solution, a molecular weight of a polymer material, a concentration of the pre-polymer solution, a concentration of the polymer material, an exposure time, a power (e.g., an intensity of light emitted from a fabrication system), a thickness, a time scale factor (e.g., a first layer time scale factor), or a combination thereof. As a non-limiting example, in some embodiments, the molecular weight of the pre-polymer solution and/or the molecular weight of the polymer material is a about 2,000 molecular weight PEGdA-500. In some embodiments, the concentration of the pre-polymer solution and/or the concentration of the polymer material is about 20 wt %. In some embodiments, an exposure time is in a range of about 1.5 seconds to about 10 seconds. In some embodiments, the power is about 20 milliwatts per square centimeter ($mW/cm^2$). In some embodiments, a thickness (e.g., a layer thickness or a slice thickness) is from about 50 µm to about 100 µm. In some embodiments, a first layer time scale factor (e.g., a first layer time scale factor) is from about 2× seconds to about 8× seconds.

In some embodiments, the one or more length design criteria in the plurality of design criteria of the determining includes a first length associated with the microchannel vascular network design and a second length associated with the microchannel vascular network device. Furthermore, in some embodiments, the second size is less than the first size.

In some embodiments, the second length is based on the first length, the polymer, the fabrication system, or a combination thereof. In some embodiments, the second length forms a microchannel vascular network device with a volume in between 1.49 milliliter (mL) and 4.51 mL.

In some embodiments, the one or more polymer design criteria in the plurality of design criteria includes selecting the polymer of the forming based on a degree of swelling of the polymer. In some embodiments, the degree of swelling is based on or more parameters including one or more dimensional parameters (e.g., planar swelling, volumetric swelling), one or more mass parameters (e.g., mass swelling), a temporal parameter (e.g., per unit time), or a combination thereof. In some embodiments, the degree of swelling is a ratio of a difference between a wet weight and a dry weight in comparison to the wet weight. For instance, a swelling ratio of hydrogel is an important factor for tissue engineering application. To demonstrate swelling properties of PEGDA hydrogel microchannel devices, the devices were applied to a PBS solution, and a swelling weight of the devices was determined. Then, the hydrogel was lyophilized to obtain dry weight. The swelling degree was calculated as following equation: Swelling Ratio=Wwet-Wdry Wwet. A week of immersion in PBS at 4'C, the sizes w, h, d1, and d2 of printed devices were increased for 18%, 15%, 16%, and 13%, respectively. Following three weeks, the swelling was maintained steady which indicates that the swelling ratio and degradation ratio reached at equilibrium state.

In some embodiments, the one or more length design criteria in the plurality of design criteria includes a resolution of a length of the microchannel vascular network device. In some embodiments, the resolution is in between a 0.005 inch and 0.010 inch resolution. In some embodiments, the one or more length design criteria in the plurality of design criteria includes a first resolution of a first length of the microchannel vascular network device and a second resolution of a second length of the microchannel vascular network (e.g., a 0.005 inch resolution of the x-y plane of the microchannel vascular network device 700).

In some embodiments, the one or more polymer design criteria in the plurality of design criteria includes a porosity of the microchannel vascular network device. In some embodiments, the porosity of the microchannel vascular network device is determined based on a candidate subject associated with the microchannel vascular network device. For instance, in some embodiments, the porosity of the microchannel vascular network device is determined to allow a candidate subject cell to attach to a pore of the microchannel vascular network device. In some embodiments, a median size of a pore of the microchannel vascular network device is from about 19 µm to about 231 µm. For instance, in some embodiments, the plurality of design criteria include a permeability of a porous material of the microchannel device.

In some embodiments, the determining further includes determining one or more design criteria in the plurality of the design criteria that is associated with the forming of the polymer material from the pre-polymer solution. For instance, in some embodiments, the design the design criteria that is associated with the forming of the polymer material from the pre-polymer solution include a material design property of the pre-polymer solution.

Block 504. Referring to block 504, the method 500 includes receiving, in electronic form, the microchannel vascular network design at a fabrication system. In some embodiments, the receiving includes communicating one or more instructions to a fabrication mechanism associated with the fabrication control mechanism of the fabrication system based on the microchannel vascular network design.

In some embodiments, the fabrication system 200 includes a pre-polymer solution. For instance, in some embodiments, the fabrication system 200 includes a plurality of pre-polymer solutions, allowing the fabrication system provide the pre-polymer solution for fabricating a microchannel vascular network device 700. In some embodiments, the pre-polymer solution is provided to the fabrication system 200 is a pre-formed. However, the present disclosure is not limited thereto. For instance, in some embodiments, the fabrication system forms the pre-polymer solution for use in forming the microchannel vascular network device 700.

In some embodiments, the pre-polymer solution includes a photoinitiator, such that exposing the pre-polymer solution with the photoinitiator to light causes a crosslinking effect, which in turn forms a polymer material.

Block 506. Referring to block 506, the method includes forming, based on the microchannel vascular network design, a microchannel vascular network device of a polymer material at the fabrication system using the pre-polymer solution. In this way, the method facilitates fabricating the microchannel vascular network device.

In some embodiments, the polymer material includes poly-dimethyl-siloxane (PDMS), poly-glycerol-sebacate (PGS), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon©, nylon silicon, and shape memory materials, such as poly(styrene-block-butadiene), polynorbornene, hydrogels, metallic alloys, and oligo (ε-caprolactone)diol as switching segment/oligo (p-dioxyanone)diol as physical crosslink. For instance, in some embodiments, the PLGA polymer is a PLA/PGA polymer=50/50 with a molecular weight of 30,000 Da.

For instance, by utilizing a PLGA polymer, the present disclosure

In some embodiments, the polymer material of the microchannel vascular network device is transparent. In some embodiments, the polymer material of the microchannel vascular network device is transparent, translucent, opaque, or a combination thereof. By having a transparent and/or translucent microchannel vascular device, a subject can optically inspect an internal portion of the microchannel vascular network device without having to disturb the contents therein. For instance, referring to FIGS. 27, 29-34, and 36-40, embodiments include transparent and or translucent fabrications of a respective microchannel vascular network are provided. Specifically, FIG. 31 illustrates a plurality of microscopic images of a plurality of PLGA microspheres (e.g., beads) within (A) twenty conical shaped structures interposing between a corresponding first channel network and a corresponding second channel network; (B) twenty spherically shaped structures interposing between the corresponding first channel network and the corresponding second channel network; and twenty cylindrical shaped structures interposing between the corresponding first channel network and the corresponding second channel network. For instance, the respective microchannel device of FIG. 31 (A), depicts that a portion of the microspheres are trapped within the internal portions of the structures without a difference in top-to-bottom size, as opposed to the respective devices of FIG. 31 (B) and (C).

In some embodiments, the polymer is a biodegradable material. In some embodiments, the polymer is non-resorbable, resorbable, absorbable, biodegradable or a combination thereof. By utilizing a biodegradable material, such as PEGdA, a respective microchannel vascular network device can be implanted within a subject without having to later remove the microchannel vascular network device (e.g., with an invasion procedure).

In some embodiments, the forming includes exposing the pre-polymer solution to ultraviolet light for a predetermined period of time. For instance, in some embodiments, the fabrication system includes a vat photopolymerization mechanism, which facilitates exposing the pre-polymer solution to ultraviolet light. Moreover, in some embodiments, the fabrication system utilizes volumetric printing.

In some embodiments, the fabrication system utilizes an additive manufacturing method for the forming. In some embodiments, the additive manufacturing method is selected from the group consisting of: binder jetting, material extrusion, material jetting, polyjet, powder bed, sheet lamination, and vat photopolymerization. In some embodiments, the additive manufacturing method of vat photopolymerization includes stereolithography (e.g., projection stereolithography).

Figure 39:
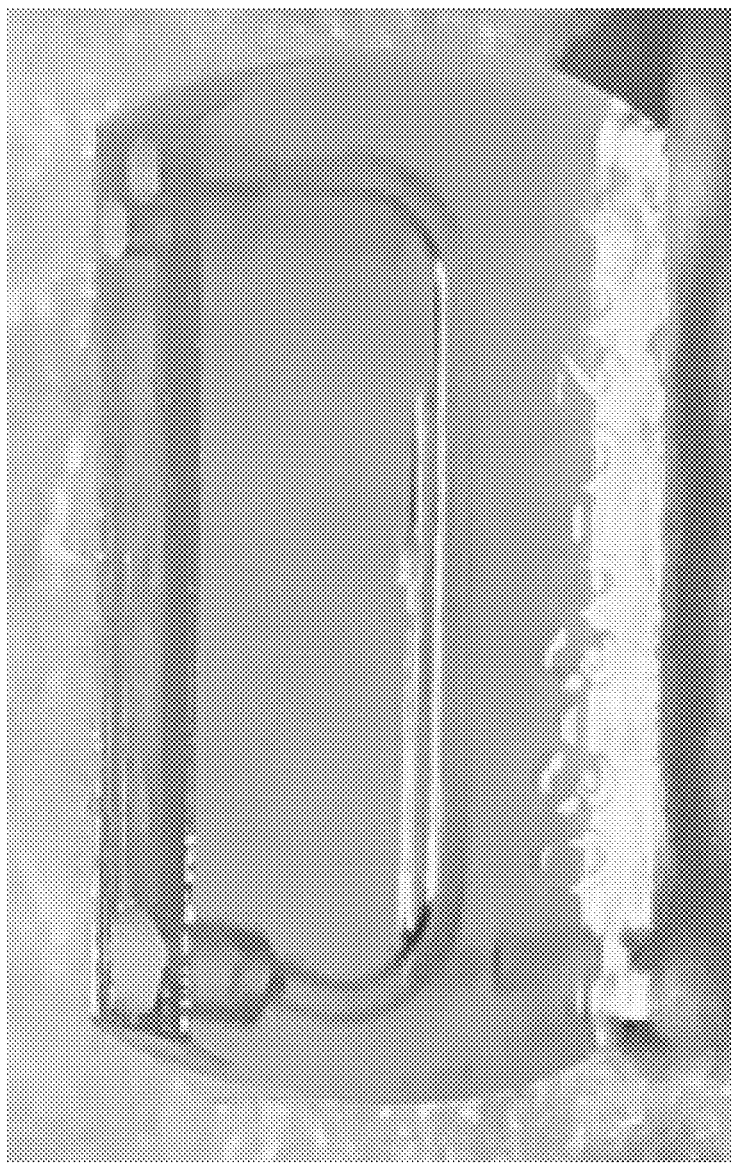
Figure 40:
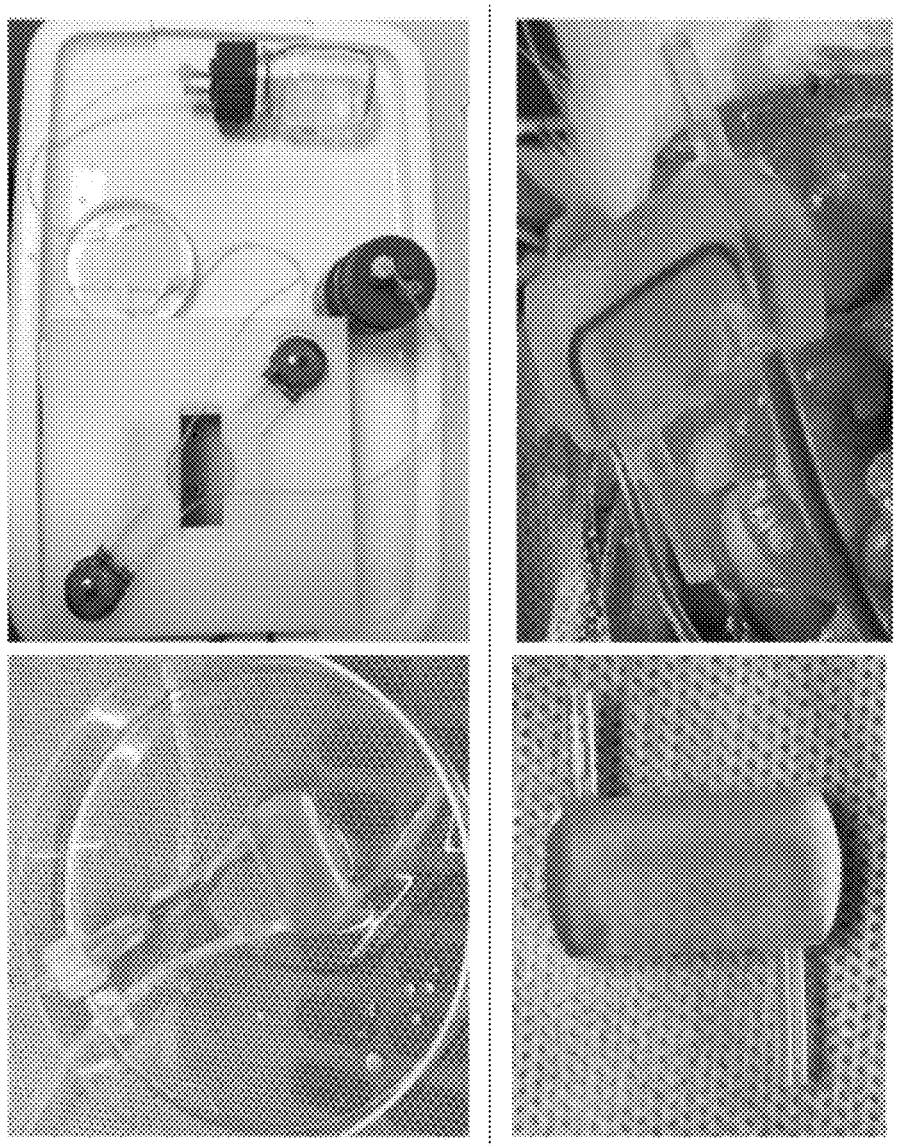

In some embodiments, the forming forms the microchannel vascular network device with a positive mold, thereby forming a void in between the first channel network and the second channel network. In some embodiments, the forming forms the microchannel vascular network device with a positive mold, thereby forming a void in between the first channel network and the second channel network. For instance, FIG. 38 illustrates a respective microchannel vascular network device formed as a positive mold, whereas FIG. 39 illustrates a respective microchannel vascular network device formed as a negative mold.

Now that a general method 500 for fabricating a microchannel vascular network device 700 has been described in accordance with various embodiments of the present disclosures, details regarding some processes for seeding a microchannel vascular network device in accordance with FIG. 6 will be described. FIG. 6 illustrates a second flow chart of methods (e.g., method 600) for seeding a microchannel vascular network device 700 in accordance with embodiments of the present disclosure. In the flow charts, the preferred parts of the methods are shown in solid line boxes, whereas optional variants of the methods, or optional equipment used by the methods, are shown in dashed line boxes.

Block 602. Referring to block 602 of FIG. 6, a method 600 includes preparing, based on a candidate subject, a microchannel vascular network device, thereby forming a prepared microchannel vascular network device. The prepared microchannel vascular channel device includes a first channel network and a second channel network.

In some embodiments, the preparing further includes, preparing the plurality of cells for the seeding.

In some embodiments, the preparing the plurality of cells includes exposing the plurality of cells to a solution. In some embodiments, the solution includes calcium and magnesium.

In some embodiments, an exposure time of the plurality of cells to the solution is from about 15 minutes to about 25 minutes. In some embodiments, the exposure time of the plurality of cells to the solution is approximately 20 minutes.

In some embodiments, the preparing the microchannel vascular network device includes modifying a surface of the microchannel vascular network device.

In some embodiments, the surface modification of the microchannel vascular network device is a chemical surface modification, a mechanical surface modification, or both. In some embodiments, the chemical surface modification is conducted prior to the mechanical surface modification. In other embodiments, the mechanical surface modification is conducted prior to, or concurrently with, the chemical surface modification.

In some embodiments, the chemical surface modification includes forming a conjugation on the surface of the microchannel vascular network device. Conjugating a compound of the present disclosure and a donor or acceptor through reactive functional groups on the conjugation partners and an appropriate linker, adaptor, carrier molecule or a combination thereof is well within the abilities of those of skill in the art.

For instance, in some embodiments, a surfactant of the present disclosure is conjugated to a carrier molecule through a linker having one or more than one amino acid.

Exemplary amino acids of use in such linkers include lysine, proline and acidic amino acids.

In some embodiments, the conjugation is a peptide conjugation. For instance, in some embodiments, a surfactant of the microchannel vascular network device 700 includes both polar and non-polar groups. Accordingly, through the forming the peptide conjugation, the non-polar groups of the surfactant conjugate with the surface of the microchannel vascular network device 700. On the other hand, the polar groups of the surfactant captures one or more proteins and/or one or more cells of within the microchannel vascular network device 700. Accordingly, by forming the peptide conjugation, a wettability of the surface of the microchannel vascular device 700 increases, which improves an ability of culturing cells within the microchannel vascular network device 700.

In an exemplary embodiment, the peptide is a tri-peptide. In various embodiments, the peptide contains one or more of arginyl, glycyl or aspartic acid residue(s). In some embodiments, the peptide includes a member selected from arginyl and glycyl, arginyl and aspartic acid, and glycyl and aspartic acid. In an exemplary embodiment, the peptide includes a dipeptidyl residue selected from Arginylglycyl, glycylaspartic acid, and combinations thereof. For instance, in some embodiments, the peptide conjugation is an arginylglycylaspartic acid peptide. The peptide is conjugated either directly or through a linker to the surface. Many routes of conjugating peptides to surfaces are known. In one example, a carboxylic acid group on the peptide is activated and reacted with a surface or a linker having an amine or hydroxyl moiety. In another example a carboxylic acid moiety on the surface is activated and is subsequently reacted with an amine on the peptide. As will be apparent, the same is true of those embodiments, using linkers. The peptide can be conjugated to a linker bound to the surface or, alternatively, a peptide-linker cassette can be bound to the surface, or two a second linker already present on the surface.

Further non-limiting information on conjugation strategies in various embodiments are set forth below.

The compounds and conjugates of the invention are assembled from covalent bonding reactions between precursors bearing a reactive functional group, which is a locus for formation of a covalent bond between the precursors. The precursors of compounds of the invention bear a reactive functional group, which can be located at any position on the compound. The finished dye conjugates can include a further reactive functional group at any point on the molecule. In various embodiments, a reactive functional group on the peptide is reacted with a reactive functional group on a surface (or a linker attached to a surface) to couple the two components together covalently through a linkage fragment.

Exemplary species include a reactive functional group attached directly to an peptide nucleus or to a linker attached to a component of a surface. An exemplary reactive functional group is attached to an alkyl or heteroalkyl moiety. When the reactive group is attached a substituted or unsubstituted alkyl or substituted or unsubstituted heteroalkyl linker moiety, the reactive group is preferably located at a terminal position of the alkyl or heteroalkyl chain. Reactive groups and classes of reactions useful in practicing the present invention are generally those that are well known in the art of bioconjugate chemistry. Currently favored classes of reactions available with reactive dye-based compounds of the invention are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and derivatives thereof including, but not limited to activated esters, e.g., N-hydroxysuccinimide esters, N-hydroxyphthalimide, N-hydroxybenztriazole esters, p-nitrophenyl esters; acid halides; acyl imidazoles; thioesters; alkyl, alkenyl, alkynyl and aromatic esters; and activating groups used in peptide synthesis;

(b) hydroxyl groups and hydroxylamines, which can be converted to esters, sulfonates, phosphoramidates, ethers, aldehydes, etc.

(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, allowing derivatization via formation of carbonyl derivatives, e.g., imines, hydrazones, semicarbazones or oximes, or via such mechanisms as Grignard addition or alkyllithium addition;

(f) sulfonyl halide groups for reaction with amines, for example, to form sulfonamides;

(g) thiol groups, which can be converted to disulfides or reacted with acyl halides, for example;

(h) amine, hydrazine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

In various embodiments, the reactive functional group is a member selected from:

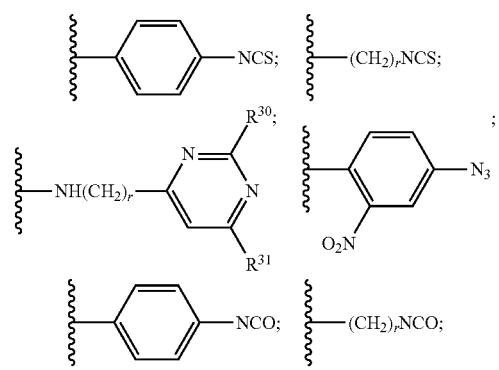

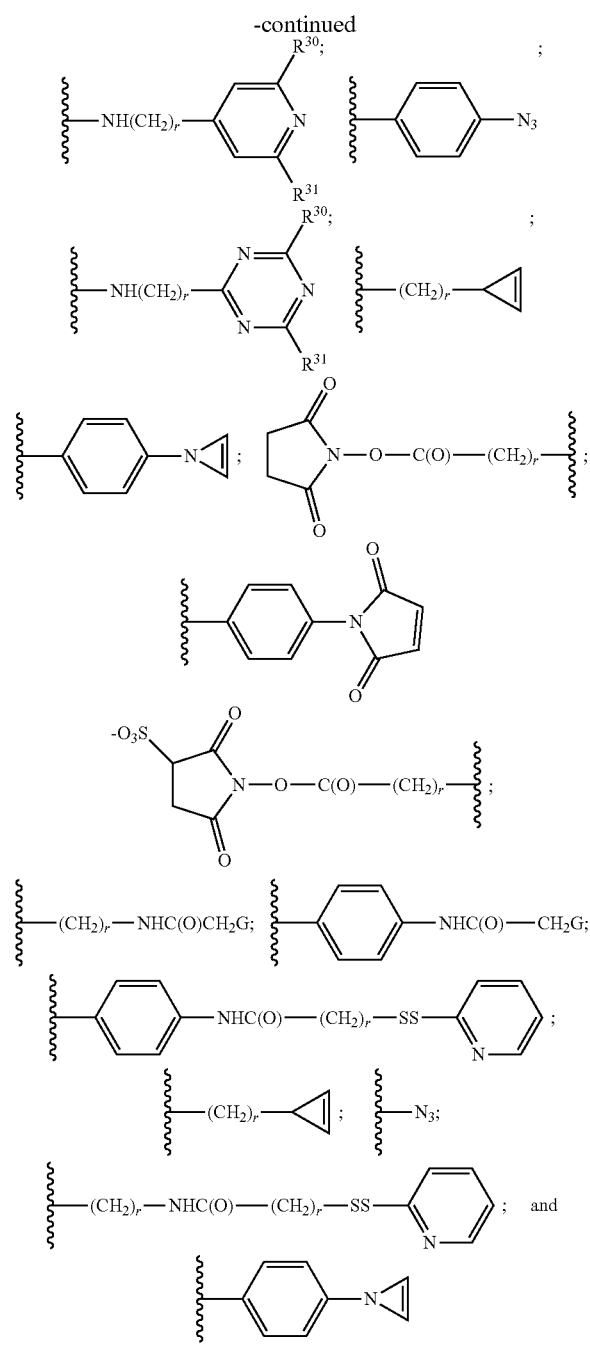

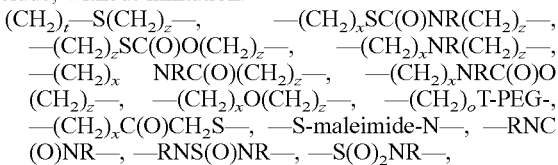

in which each r is independently selected from the integers from 1 to 10; G is a halogen; and $R^{30}$ and $R^{31}$ are members independently selected from H and halogen and at least one of $R^{30}$ and $R^{31}$ is halogen.

The reactive functional groups can be chosen such that they do not participate in, or interfere with, the reactions necessary to assemble or utilize the functionalized surface or peptide. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In various embodiments, the peptide is attached to the surface through a linkage fragment, or a linker including at least one linkage fragment. Exemplary linkage fragments include a bond and a moiety that includes at least one heteroatom, which is formed by the reaction of two reactive functional groups of complementary reactivity. Exemplary linkage fragments of use in the conjugates of the invention include, without limitation:

$(CH_2)_t$—$S(CH_2)_z$—, —$(CH_2)_x SC(O)NR(CH_2)_z$—, —$(CH_2)_z SC(O)O(CH_2)_z$—, —$(CH_2)_x NR(CH_2)_z$—, —$(CH_2)_x$ $NRC(O)(CH_2)_z$—, —$(CH_2)_x NRC(O)O$ $(CH_2)_z$—, —$(CH_2)_x O(CH_2)_z$—, —$(CH_2)_o T$-PEG-, —$(CH_2)_x C(O)CH_2 S$—, —S-maleimide-N—, —RNC(O)NR—, —RNS(O)NR—, —$S(O)_2 NR$—, Wherein T is a member selected from S, NH, NHC(O), C(O) NH, NHC(O) O, OC(O) NH, and O. The index o is an integer from 1 to 50; and the indices t and z are independently selected from the integers from 0 to 10.

The linkage fragments can also be formed via "Click Chemistry between one component having an azide moiety and another component with an alkyne moitey. The donor or acceptor can be derivatized with either reactive functional group as can the carrier molecule.

As a non-limiting example, consider a microchannel vascular network device include PEG-based hydrogol polymer material, which are well known for bioinert protein- and cell repellent properties. Accordingly, to improve a cellular attachment property of the PEGdA material, the present disclosure chemically activate a surface into of the microchannel vascular network device by conducting a chemical surface modification, which forms a biologically functional surface through a conjugation of RGD peptides. For instance, by an RGD conjugation chemical surface modification, an ability for a plurality of cells to proliferate (e.g., culture) within the microchannel vascular network device 700 is greatly improved.

In some embodiments, the chemical surface modification includes a surface grafting modification. For instance, in some embodiments, a surface of the microchannel vascular network device 700 includes an acrylic surface, such that the chemical surface modification includes conducting a surface grafting via opening an epoxy and/or kenotic group on the surface, thereby increasing a number of hydroxyl groups on the surface of the microchannel vascular network device 700.

In some embodiments, the surface modification of the microchannel vascular network device is a mechanical surface modification. In some embodiments, a mechanical surface modification is applied to the microchannel vascular network device 700, either alone or in combination with a chemical surface treatment. For instance, in some embodiments, the chemical surface treatment forms one or more contaminant particles, which requires treatment through the mechanical surface modification. In this way, the mechanical surface modification can create a structure between the surface of the microchannel vascular network device 700 and a plurality of cells within the microchannel vascular network device 700 to prevent an interaction between a respective cell and a respective contaminate particle.

In some embodiments, the mechanical surface modification includes applying a coating to the surface of the microchannel vascular network device. In some embodiments, the coating includes collagen, fibronectin, gelatin, GelMA, PEGdA, PLL, or a combination thereof.

In some embodiments, the coating includes a first percentage by weight (wt %) of PEGdA from about 8% to about 12%, and a second wt % of GelMa from about 0.5% to about 7%. In some embodiments, the first wt % of PEGdA is 10%, and the second wt % of GelMA from about 1% to about 5%. In some embodiments, the second wt % of GelMA is between 4% and 5%.

In some embodiments, the coating includes a first coating comprising PEGdA, PPL, GelMA, or a combination thereof. The first coating including an first upper surface and a first lower surface. The coating further includes a second coating including either collagen or gelatin. The second coating includes second upper surface and a second lower surface. Furthermore, the first lower surface is adjacent to the surface of the microchannel vascular network device, and the second lower surface is adjacent to the first upper surface.

For instance, in some embodiments, the coating includes 10% PEGdA, 5% GelMA, and 0.25% photoinitiator. In some embodiments, the coating includes 10% PEGdA coated with GelMA and then exposing the coating to UV light. In some embodiments, the coating includes 10% PEGdA further coated with 10% gelatin. In some embodiments, the coating includes 10% gelatin. In some embodiments, the coating includes aortic endothelial cells.

In some embodiments, the surface modification includes applying a NaOH-EtOH solution treatment for about 10 minutes. From this, an effectively change in surface morphology is provided by creating new cracks in the surface of the microchannel device.

Figure 35:
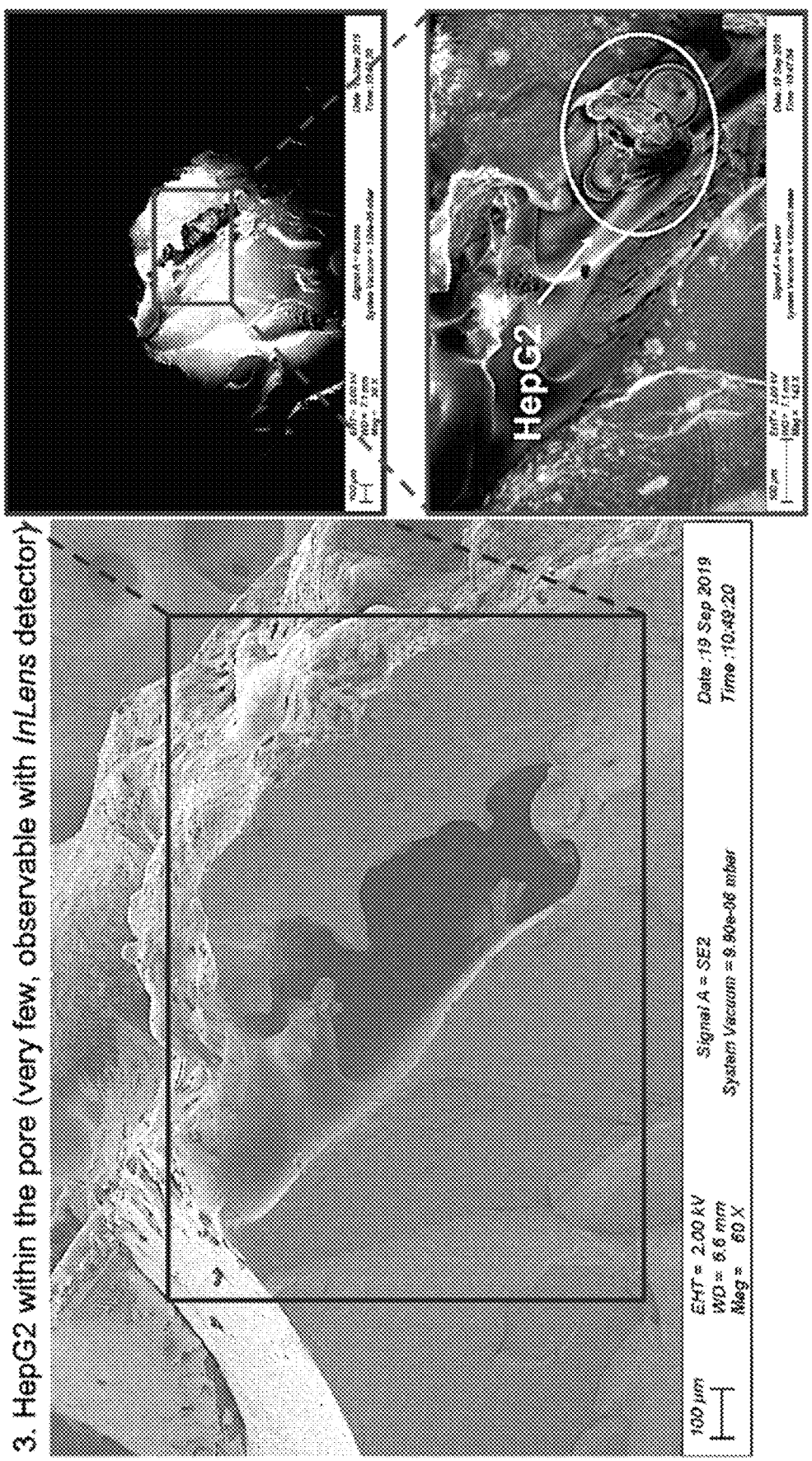
Figure 37:

For instance, referring briefly to FIG. 35, as a non-limiting example, a perfusability of cells within a respective microchannel device of PLGA polymer, an internal porous structure of the PLGA devices and cell attachment of the devices were characterized by SEM images. For the sample preparation for SEM samples, the HepG2-perfused PLGA devices were frozen and cracked manually into small fragments for the microscopic observation. The PLGA printing filaments were observed in almost all cracked PLGA fragments. BioX printer piston size is 100 um, and the real printed filaments were nearly same size. As shown in FIG. 35, irregular shaped pores (holes) were observed between filaments; sizes were varied from 20 um to 200 um. Based on this, HepG2 cells were observed on the surface of the microchannel device.

Block 604. Referring to block 604, the method 600 includes seeding, based on the candidate subject, the plurality of cells for culturing in the prepared microchannel vascular device, thereby forming a plurality of seed cells.

In some embodiments, the seeding includes encapsulating the plurality of cells in the culture medium.

In some embodiments, the culture medium includes a photoinitiator, and preceding the encapsulating the plurality of cells, the seeding further includes exposing the culture medium and the plurality of cells to ultraviolet light for a predetermined period of time.

Figure 24:
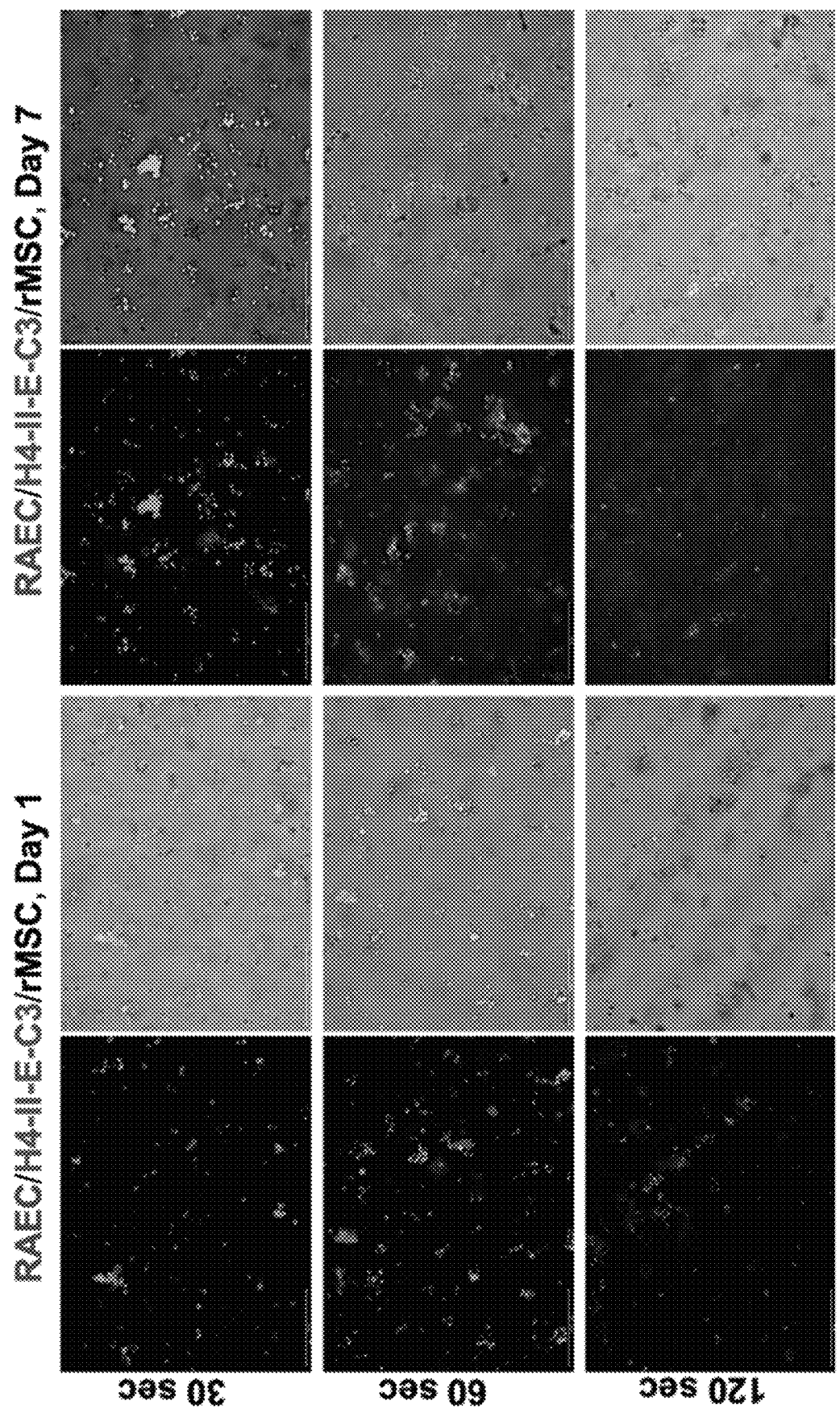
FIG. 24 illustrates an effect of cell proliferation within a PEGdA hydrogel microchannel vascular network device, in accordance with embodiments of the present disclosure.
Figure 25:
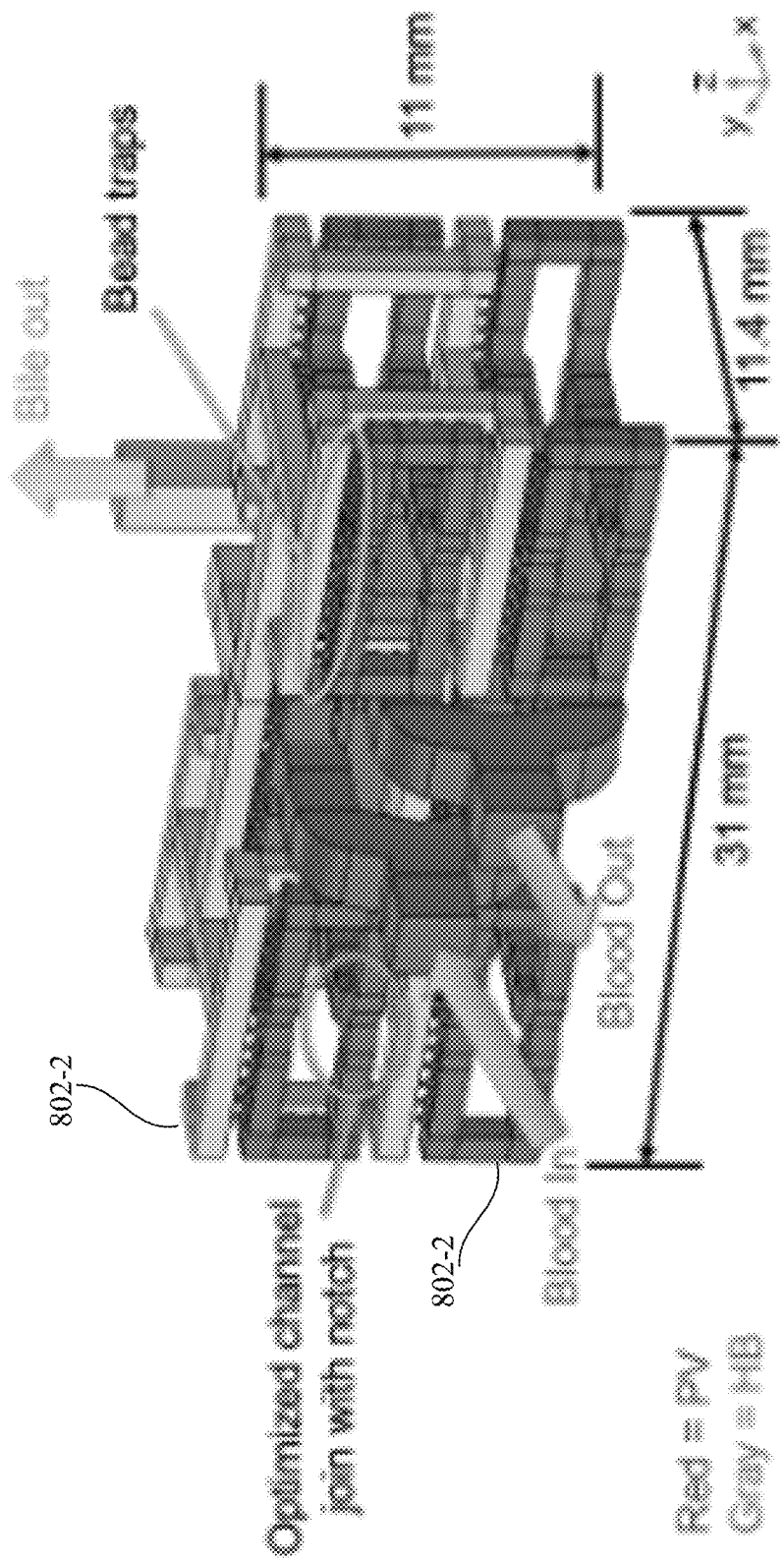
Figure 26:
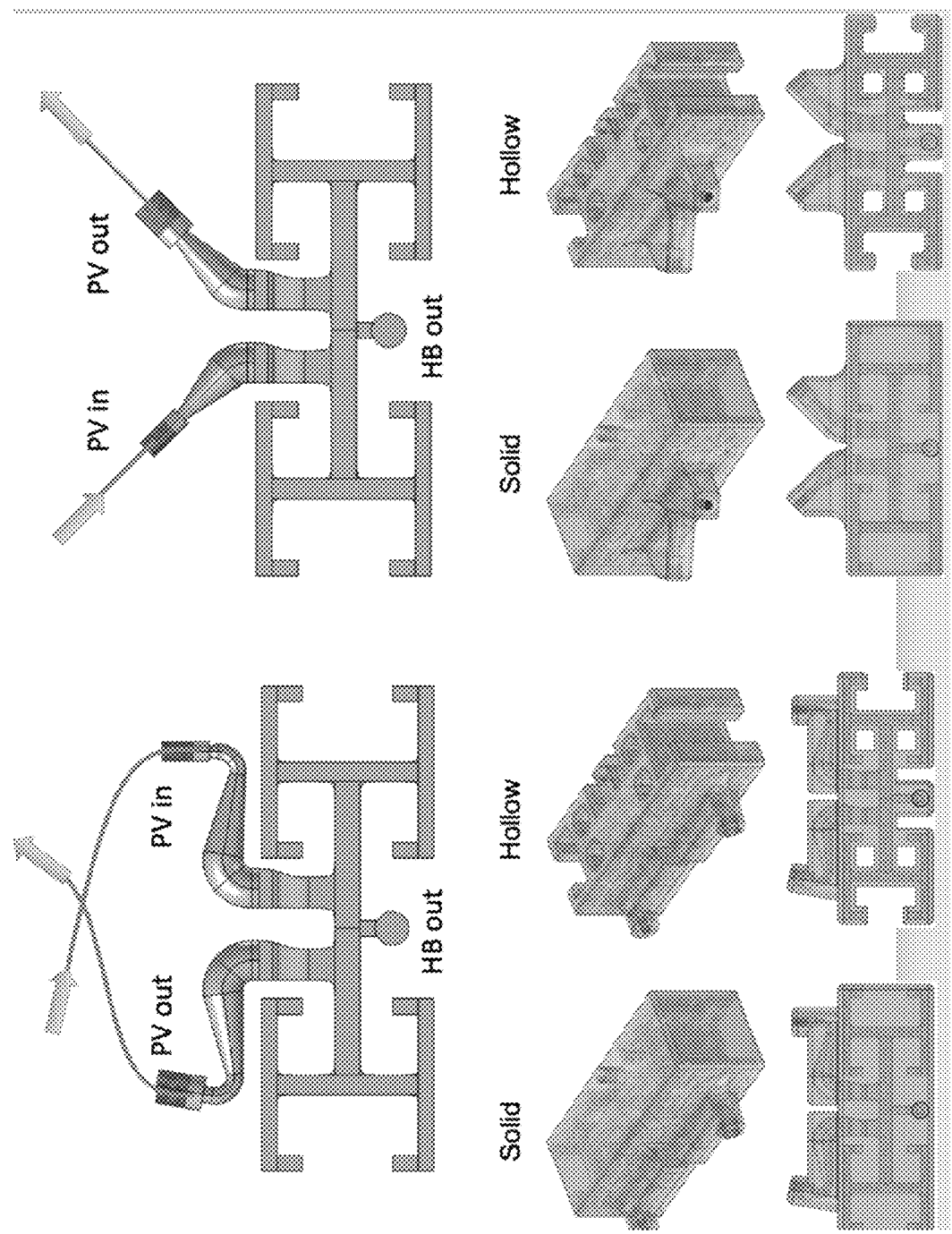
Figure 27:
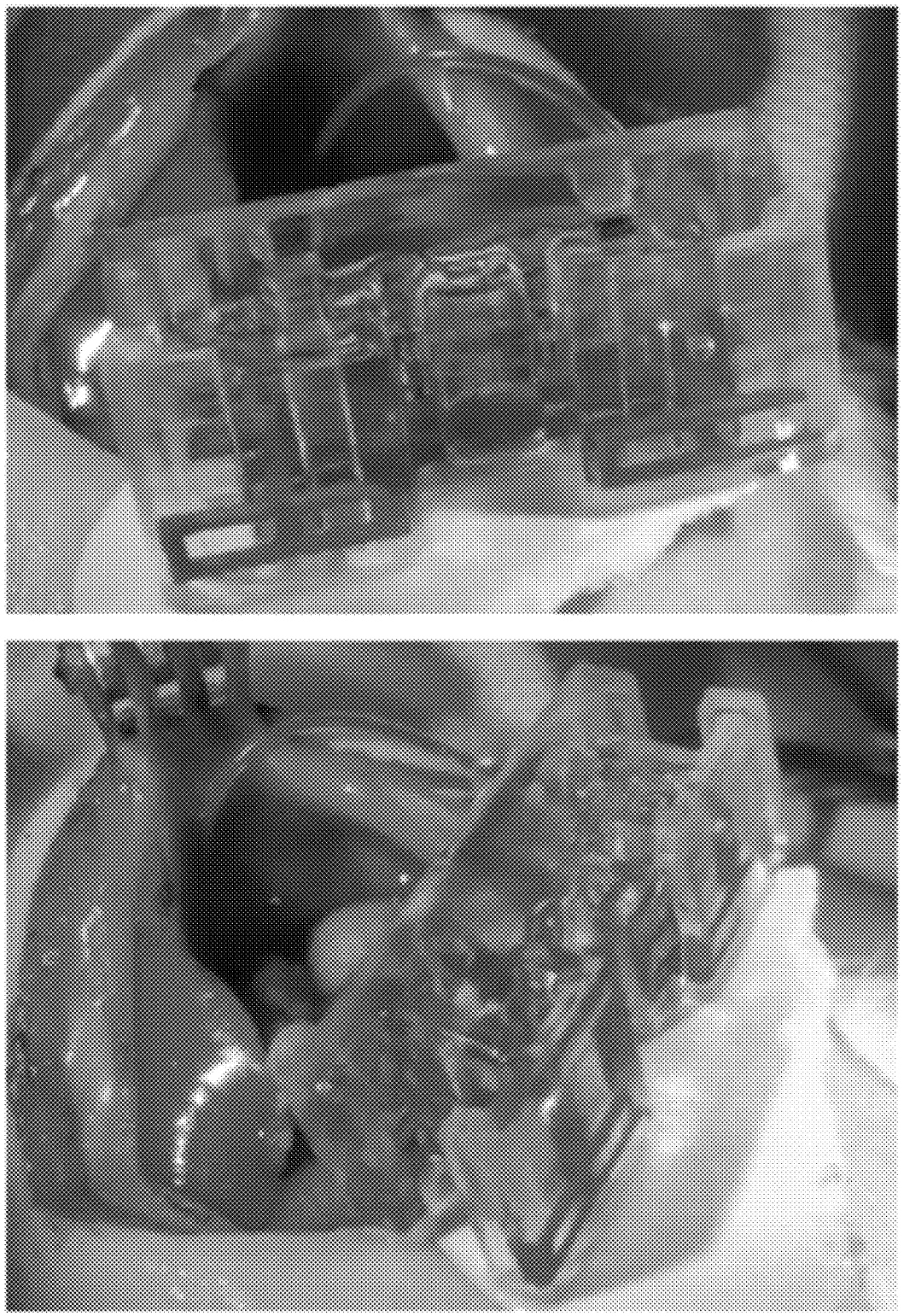
Figure 28:
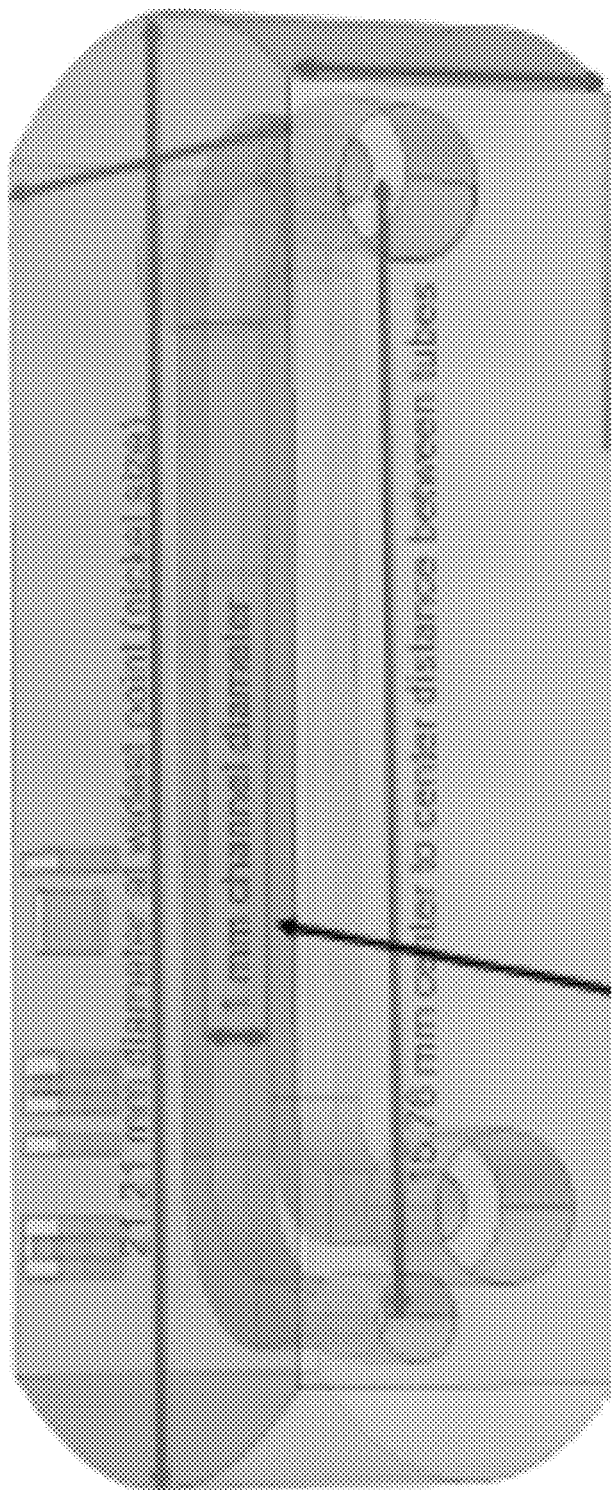
Figure 29:
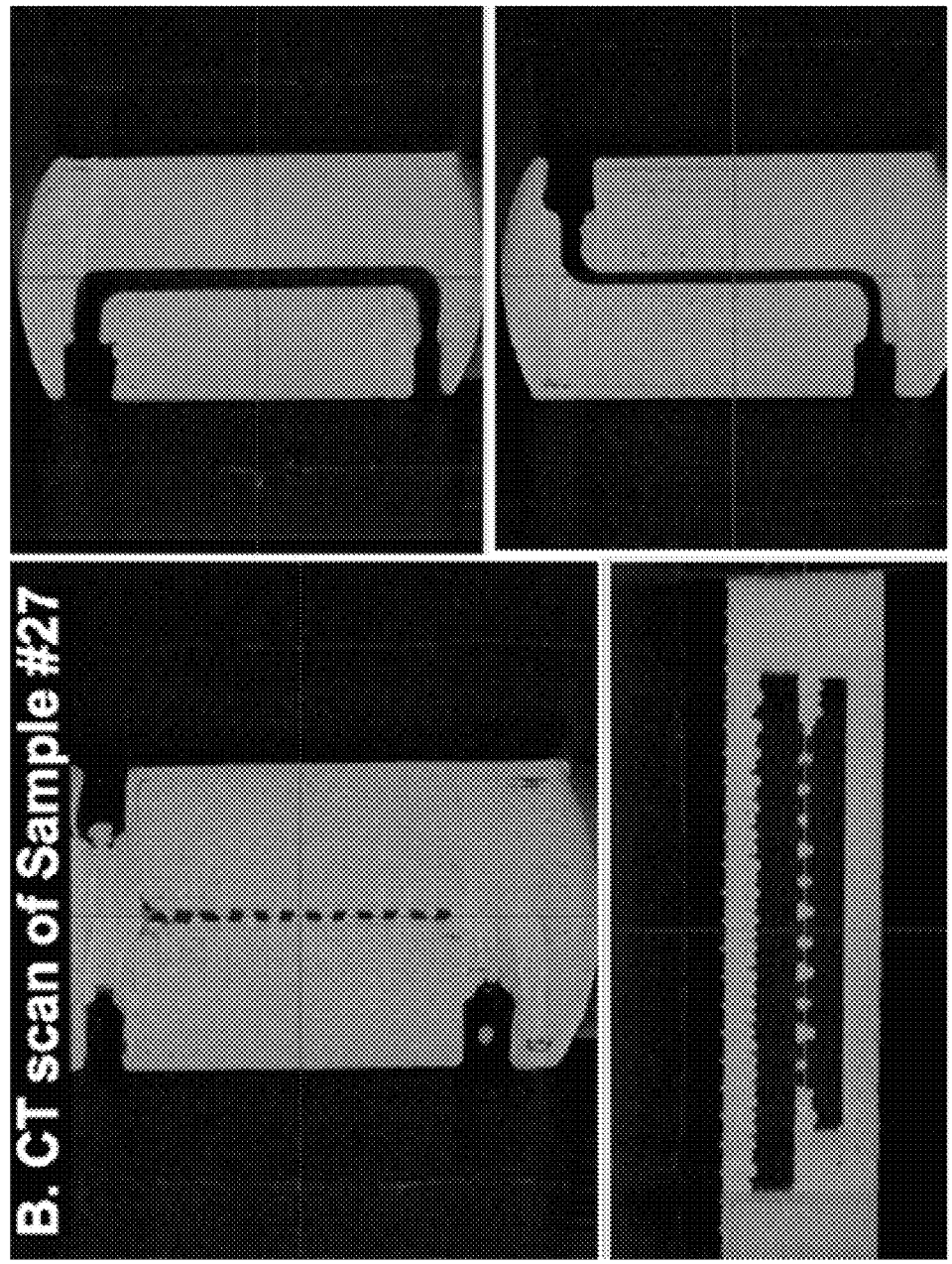

Referring briefly to FIG. 24, an effect of an exposure time on cell proliferation within PEGDA hydrogel microchannel vascular network devices is provided. Specifically, FIG. 24 illustrates a plurality of fluorescent images of encapsulated cells within a PEGDA microchannel vascular network device, with different exposure times (e.g., 30 seconds, 60 seconds, and 120 seconds). A mixture of 1.6M/mL RAEC, 0.8M/mL H4-II-EC3, and 0.4M/mL rMSCs were encapsulated in 20 wt % PEGDA hydrogel and crosslinked from about 30 sec to about 120 sec. The fluorescent images were captured on day 1 and day 7 and compared, as illustrated. RAEC cells were labeled with red, H4-II-EC3 cells were labeled with green, and the scale bar indicates 200 um. To demonstrate cellular proliferation within a hydrogel microchannel vascular network device 700, the cells were encapsulated within a 150 um thick hydrogels and cultured for 1 to 7 days (e.g., method 600 of FIG. 6). Photo-irradiation was varied from about 30 seconds to about 2 minutes, to evaluate an effect of photo exposure time on cell proliferation. On day 1, all samples showed high cellular viability regardless of photo exposure time. However, on day 7, the cells in the hydrogel that was exposed for 2 minutes were showed less than half of cellular viability comparing to that of day 1. This difference was due to phototoxicity of long irradiation and large amount of free radicals generates from photo-initiator molecules. In contrast, the cells within the hydrogels that were exposed 30 sec and 60 sec were maintained their cell viability after 7 days of culture. This indicates that up to 60 min of exposure time presented minimal cytotoxility towards encapsulated cells.

In some embodiments, the culture medium includes a thickness from about 5 μm to about 15 μm.

In some embodiments, a density of the plurality of seed cells of the seeding from about $1*10^4$ cells per square cm to about $1*10^5$ cells per square cm.

In some embodiments, the culture medium includes the plurality of cells encapsulated in collagen. This encapsulation provides an adequate support structure within the microchannel device to support culture the cells.

as cells are homogenously distributed throughout the cross section

Block 606. Referring to block 606, the method 600 includes flowing, using a bioreactor system coupled to the prepared microchannel vascular network device, a culture medium comprising the plurality of seed cells through the prepared microchannel vascular network device, thereby culturing the plurality of cells in the microchannel vascular network device.

Figure 33:
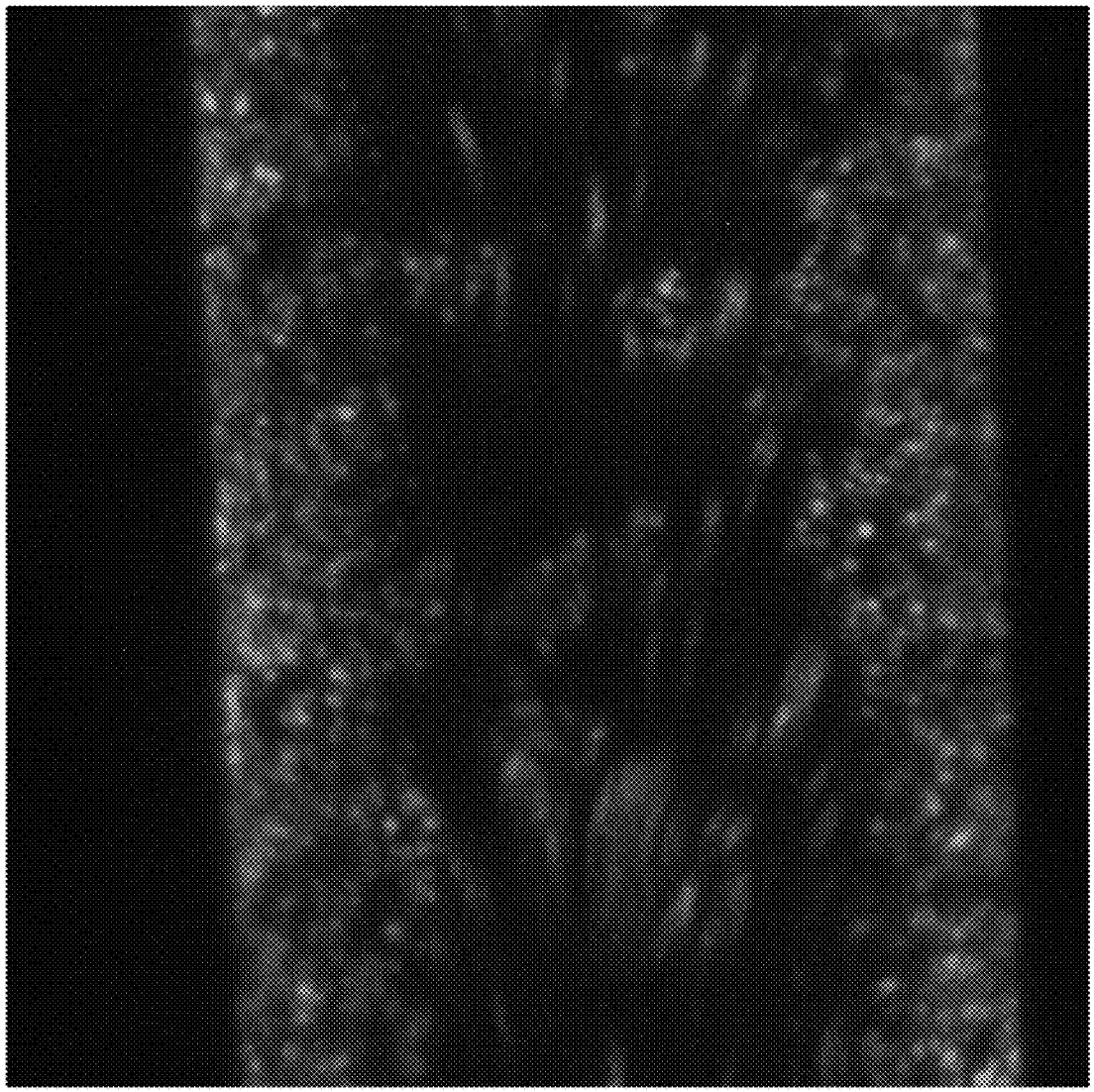
Figure 34:
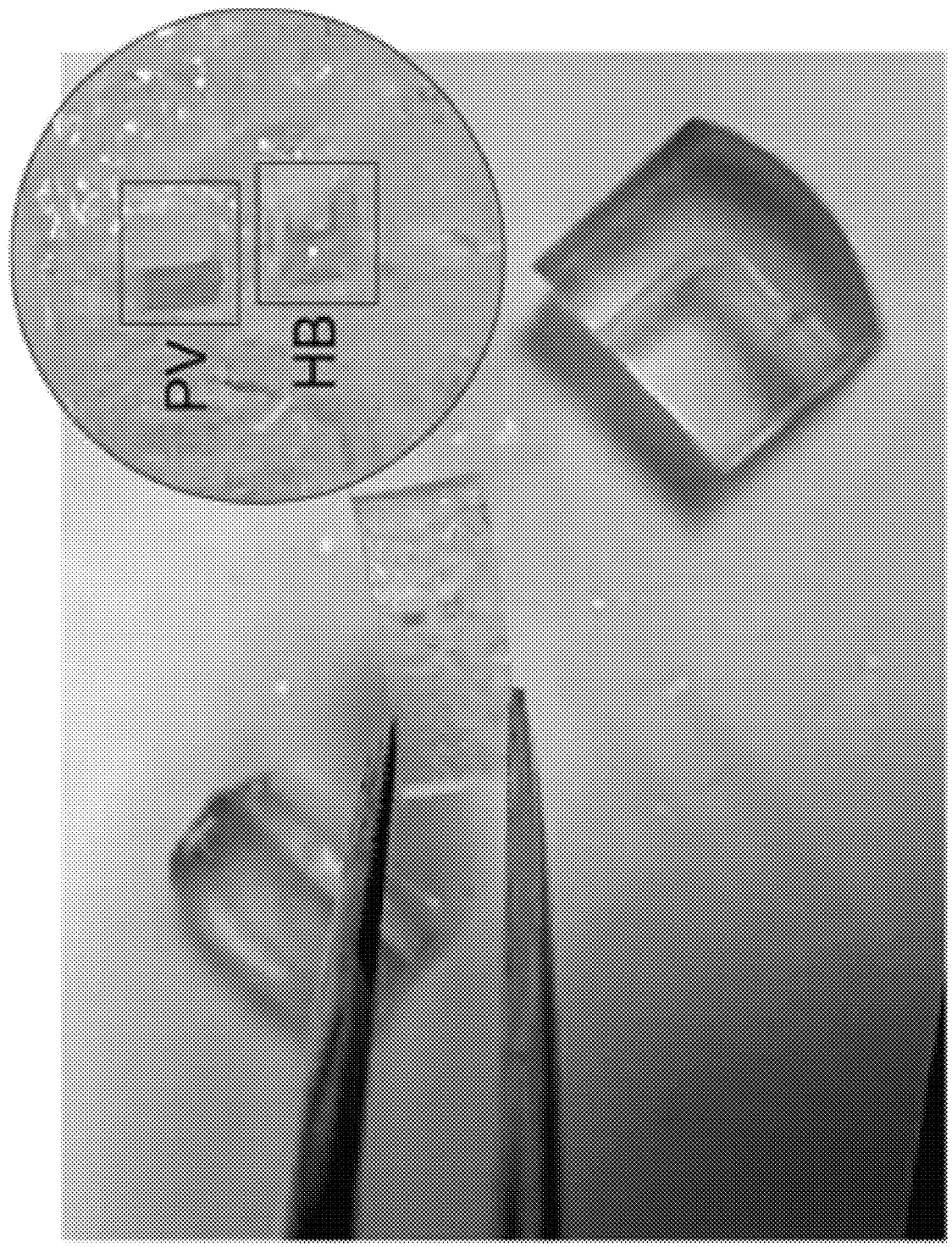

For instance, referring briefly to FIG. 33, an image of a first channel of a microchannel device is provided. As shown, movement of cells within the device is provided through a bioreactor system. Here, a diameter of the channel is about 920 μm. Accordingly, the present disclosure allows for a culture of cells within a microchannel vascular network device by allowing for a control flow within the device, as facilitated by a bioreactor system.

In some embodiments, a flow rate of the flowing is from about 375 microliters (μL) per minute to about 425 μL per minute. For instance, in some embodiments, a bioreactor system 200 communicates one or more instructions to a pump 1720, which facilitates control of the flow rate.

In some embodiments, prior to the flowing, a portion of the prepared microchannel vascular network device is in either a dry condition or a hydrated condition.

In some embodiments, prior to the flowing, the portion of the prepared microchannel vascular network device is a lower end portion of the microchannel vascular network device.

Various aspects of the present disclosure are directed to providing systems and methods for retarding or arresting flow of a medium in a device. A device of the present disclosure includes an artificial organ device (e.g., an implant), a bioreactor device, a lab on a chip device (e.g., an organ on a chip device), and the like. Accordingly, an exemplary device includes at least a first channel and a second channel through which the medium flows. Further, in some embodiments each of the first channel and the second channel includes a first opening disposed at a first end portion of the device and a second opening. The respective second openings of the first channel and the second channel may be disposed on the same end portion of the device (e.g., a second end portion of the device) or on different end portions of the device (e.g., the second end portion of the device and a third end portion of the device, respectively). Thus, each opening of a respective channel acts as an inlet or an outlet for the flow of the medium. However, the present disclosure is not limited thereto. In some embodiments, a device of the present disclosure includes a master inlet and a master inlet that are in communication with the first channel and the second channel.

As previously described, in some embodiments an exemplary device is a component of a system, such as a bioreactor system. Thus, in some embodiments each opening of a respective channel includes a portion for facilitating coupling to another component of the system, such as tubing in communication with a reservoir of the medium or a pump. In some embodiments, the coupling portion of each respective channel includes a coupling diameter that is different from a channel diameter of the respective channel. In some embodiments, the first opening and the second opening of the first channel and the second channel each have a channel diameter in a range of from about 500 micrometers (μm) to about 10,000 μm, about 500 μm to about 5,000 μm, about 500 μm to about 2,500 μm, about 500 μm to about 1,500 μm, about 500 μm to about 1,000 μm, about 650 μm to about 2,500 μm, about 650 μm to about 1,500 μm, about 650 μm to about 1,000 μm, or about 650 μm to about 750 μm. Furthermore, in some embodiments the first opening and the second opening of the first channel have a different diameter than the first opening and the second opening of the second channel.

One or more intermediate channels interconnect the first channel and the second channel. The one or more intermediate channels is configured to diffuse the medium, or a material within the medium such as nutrients and/or waste materials, to or from the first channel and the second channel of the device. In some embodiments, a rate of diffusion of the medium is proportional to a number of intermediate channels included in a device (e.g., the more intermediate channels the higher the rate of diffusion of the medium). In some embodiments, the device includes one intermediate channel, two intermediate channels, three or less intermediate channels, five or less intermediate channels, ten or less intermediate channels, fifteen or less intermediate channels, twenty or less intermediate channels, fifty or less intermediate channels, a hundred or less intermediate channels, two hundred or less intermediate channels, five hundred or less intermediate channels, a thousand or less intermediate channels, or ten thousand or less intermediate channels. Moreover, the one or more intermediate channels can be formed in a variety of shapes including a cylinder, a cuboid, a truncated cone, a three-dimensional mesh, and the like. In some embodiments, the one or more intermediate channels is formed with rounded or chamfered edges in order to provide a more uniform flow within the intermediate channel. Nevertheless, each intermediate channel is formed with an opening that is sufficiently wide to allow for a flow of the medium through the intermediate channel and be capable of receiving at least one microgel unit. In some embodiments, each channel in the one or more intermediate channels is formed with an opening of from about 50 μm to about 1,500 μm, about 50 μm to about 1,250 μm, about 50 μm to about 1,000 μm, about 100 μm to about 1,250 μm, about 100 μm to about 1,000 μm, about 100 μm to about 800 μm, about 400 μm to about 1,000 μm, about 300 μm to about 800 μm, about 300 μm to about 600 μm, or about 400 μm to about 800 μm. Moreover, in some embodiments each channel in the one or more intermediate channels is formed including a variable diameter, such that a diameter of each respective intermediate channel decreases from a first diameter of a first opening to a second diameter of a second opening. In some embodiments, the second opening is approximately from about 50% to about 90% of a size of the first opening. For instance, in some embodiments the first opening of a respective intermediate channel is 600 μm and the second opening of the respective intermediate channel is 500 μm (e.g., the second opening is approximately 83% of a size of the first opening). Furthermore, in some embodiments the diameter of the first opening of each respective intermediate channel is greater than or equal to a diameter of a microgel unit in the plurality of microgel units, while the diameter of the second opening is less than the diameter of the microgel unit in the plurality of microgel units. For instance, in some embodiments a plurality of microgel units is formed in a range of from 300 μm to 500 μm. Thus, the first opening of each intermediate channel is greater than or equal to 500 μm and the second opening of each intermediate channel is less than or equal to 300 μm. The above described configurations of variable diameters of the one or more intermediate channels allows for one or more microgel units in the plurality of microgel units suspended in the first solution to enter an intermediate channel through the first opening and subsequently become lodged in a portion of the intermediate channel that has a diameter less than that of the microgel.

For instance, referring to FIG. 7, an exemplary device 700 is illustrated. The device includes first channel 702-1 and second channel 702-2. Each channel 702 (e.g., first channel 702-1 and second channel 702-2) includes a first opening and a second opening. Accordingly, each respective opening of each channel 702 includes a coupling portion 710-1 having a coupling diameter configured to couple with another component of a system (e.g., receive a portion of a tube), and a channel portion 710-2 having a channel diameter. Further, interconnecting first channel 702-1 and second channel 702-2 are intermediate channels 704 (e.g., first intermediate channel 704-1, second intermediate channel 704-2, third intermediate channel 704-3, . . . , n'h intermediate channel 704-n). Device 700 of FIG. 7 illustrates an embodiment including sixteen intermediate channels (e.g., first intermediate channel 704-1, second intermediate channel 104-2, . . . , and sixteenth intermediate channel 704-16). In the exemplary embodiment, each intermediate channel is formed in a cuboid shape having an opening of about 400 μm.

Now that a general structure of various embodiments of devices 700 of the present disclosure have been described, various fabrication techniques and methods of the microgel units will now be described in detail.

In some embodiments, a flow of a medium within a device must be retarded or arrested. For instance, in order to seed cells within a device and have the cells attach to the channels of the device, the flow of a medium in which the cells are suspended must be retarded or arrested; otherwise, the cells risk being flushed through the device without attaching to the device. In order to facilitate this seeding, a solution including a suspension of microgel units (e.g., a medium) flows through at least one channel of the device. This flowing disposes one or more microgel units in at least one intermediate channel of the device, which retards or arrests the flow of the medium between the channels of the device.

Fabricating a plurality of gelatin methacryloyl (GelMA) microgel units can be conducted using a variety of methods. For instance, in some embodiments the plurality of GelMA microgels is fabricated via a micro-molding technique, via a photomasking technique, via a bio-printing technique, via a self-assembly technique, via an additive manufacturing technique (e.g., three-dimensional printing), via a microfluidic technique, or a combination thereof. Depending on a goal of a designer of the present disclosure and the technique of fabrication being utilized, at least a degree of methacryloyl substitution, a concentration of GelMA microgel, a concentration of a photo-initiator, and a period of time a sample solution is exposed to UV light may be controlled, either individually or in combination, to configure one or more physical properties of the resulting GelMA hydrogel. In some embodiments, the physical properties include a size of a resulting GelMA microgel such that a first fabrication technique produces one or more microgels of a first size (e.g., 50 µm) and a second fabrication technique produces one or more microgels of a second size (e.g., 500 µm). In some embodiments, the physical properties include a rate of degradation of a resulting GelMA microgel. Controlling the rate of degradation allows for the flow of the medium through the intermediate channels of a respective device to be retarded or arrested for a predetermined period of time proportional to the rate of degradation. In some embodiments, the physical properties include a shape of a resulting GelMA microgel. In some embodiments, the physical properties include a stickiness of a resulting GelMA microgel. One skilled in the art of the present disclosure will know of other physical properties that are controllable.

In some embodiments, GelMA is synthesized by a direct reaction of gelatin with methacrylic anhydride (MA) in the presence of a buffer. This reaction introduces methacryloyl substitution groups on the reactive amine and hydroxyl groups of the amino acid residues (FIG. 2). Different degrees of methacryloyl substitution are achievable in GelMA by tuning the amount of MA added to the reaction mixture, which produces GelMA with different physical properties. Photo-crosslinking of the synthesized GelMA can be conducted under exposure to ultraviolet (UV) light using a water-soluble initiator. The degree of substitution, a GelMA concentration, a photo-initiator (PI) concentration, and an exposure time to UV light are some of the parameters that allow tuning of the physical properties of the resulting GelMA hydrogel micro units.

Figure 8:
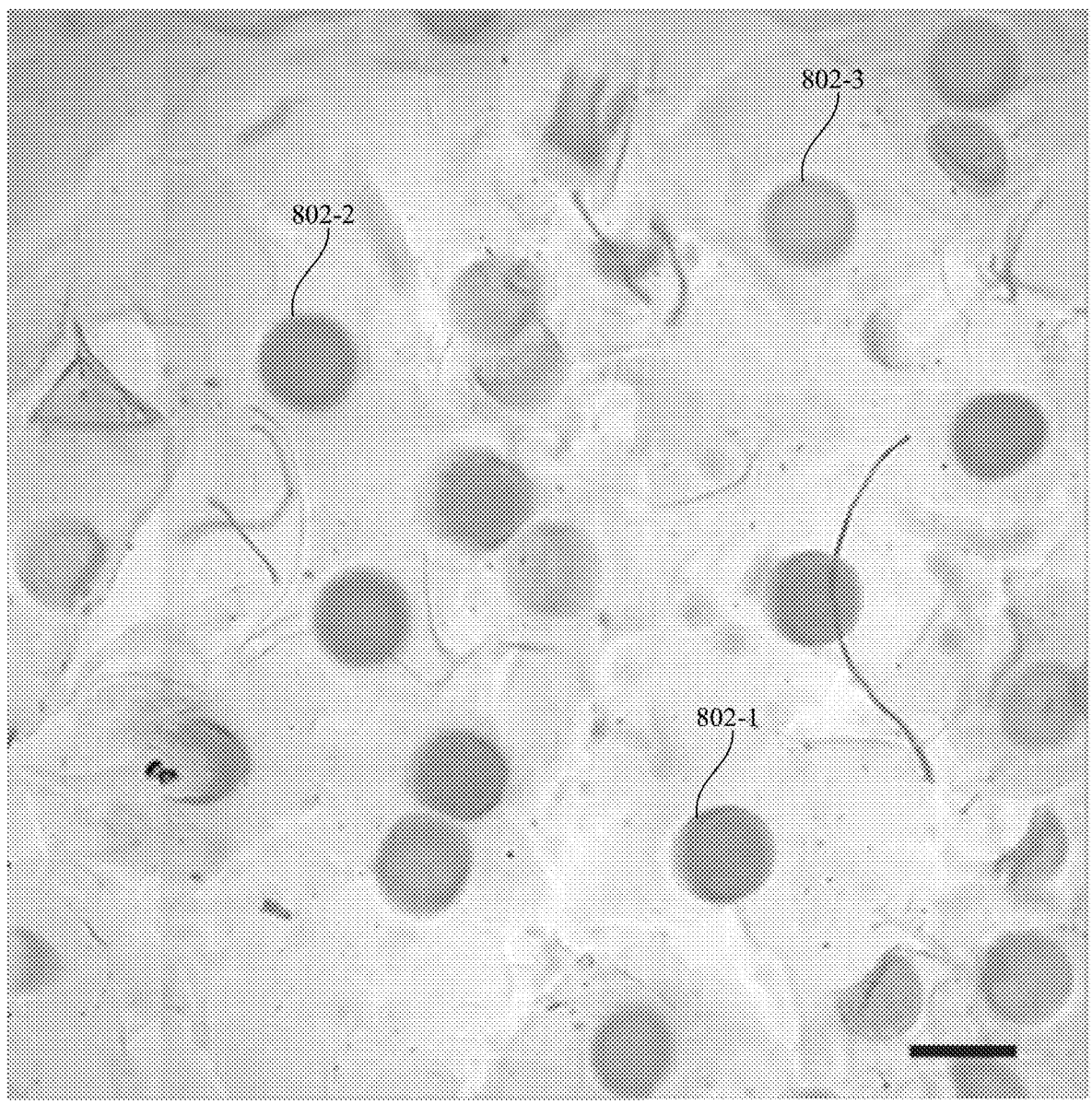
FIG. 8 illustrates exemplary microgel units in accordance with embodiments of the present disclosure.
Figure 9:
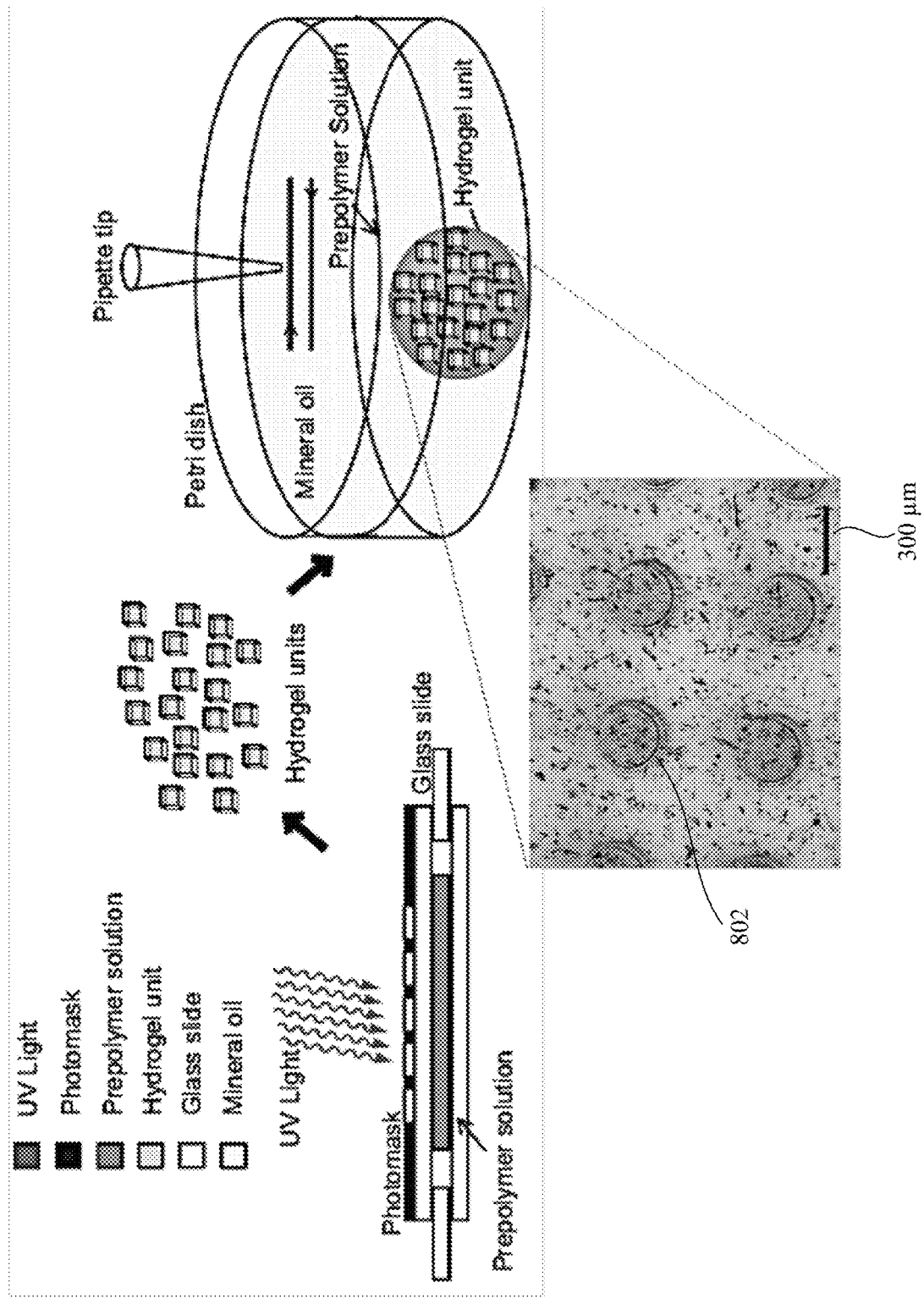
FIG. 9 illustrates an exemplary process for generating microgel units in accordance with embodiments of the present disclosure.
Figure 10:
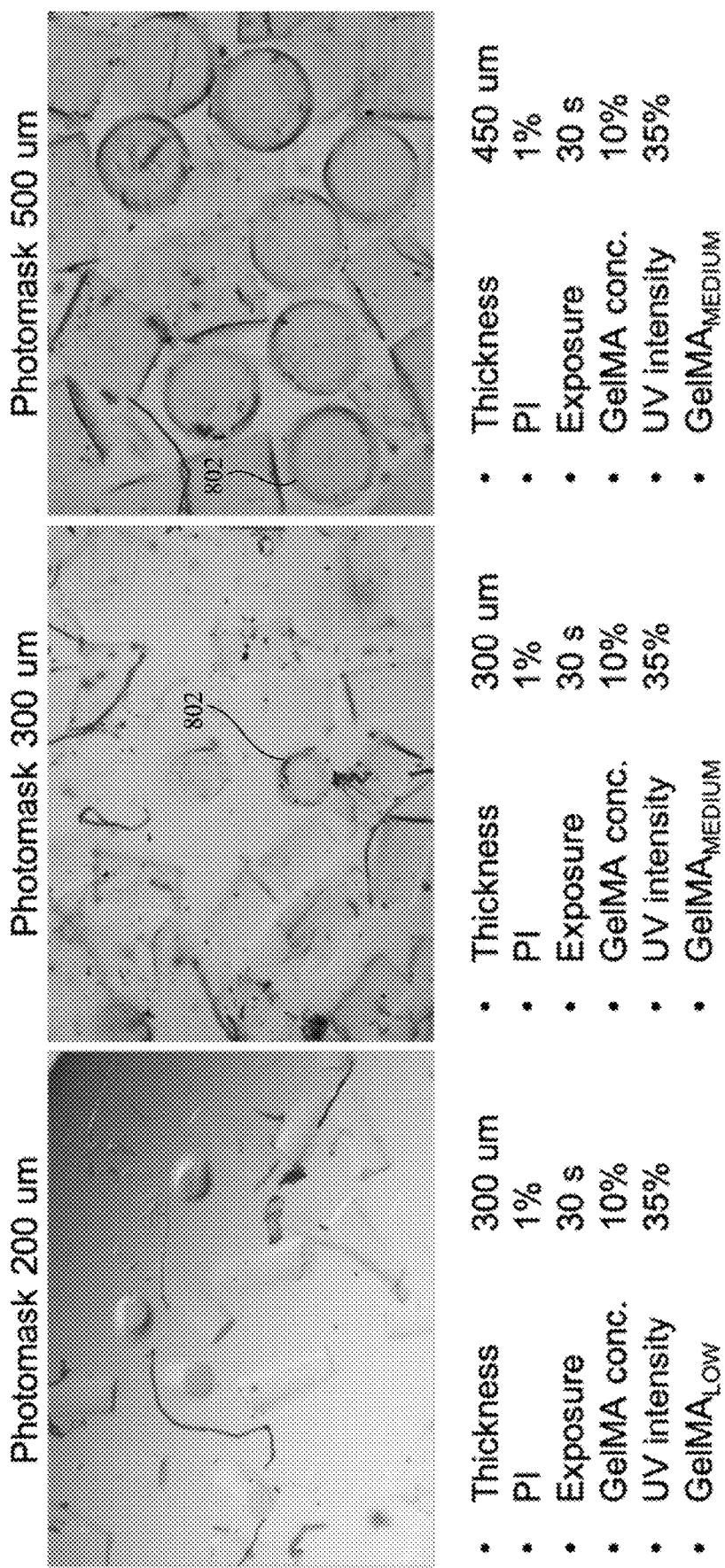
FIG. 10 illustrates various exemplary microgel units in accordance with embodiments of the present disclosure.
Figure 11:
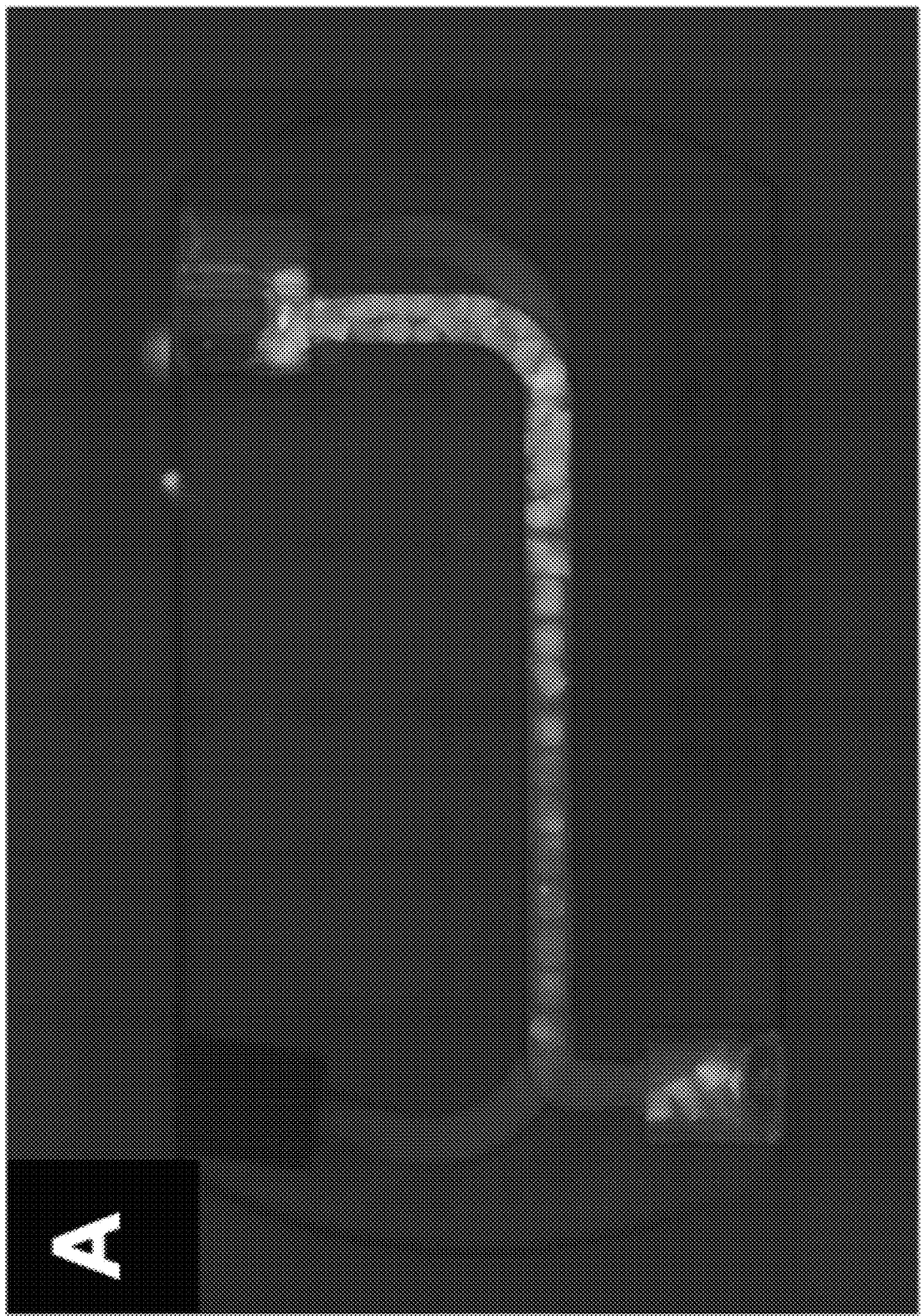
FIG. 11 illustrates a view of an exemplary microchannel device including microgel units in accordance with embodiments of the present disclosure.
Figure 12:
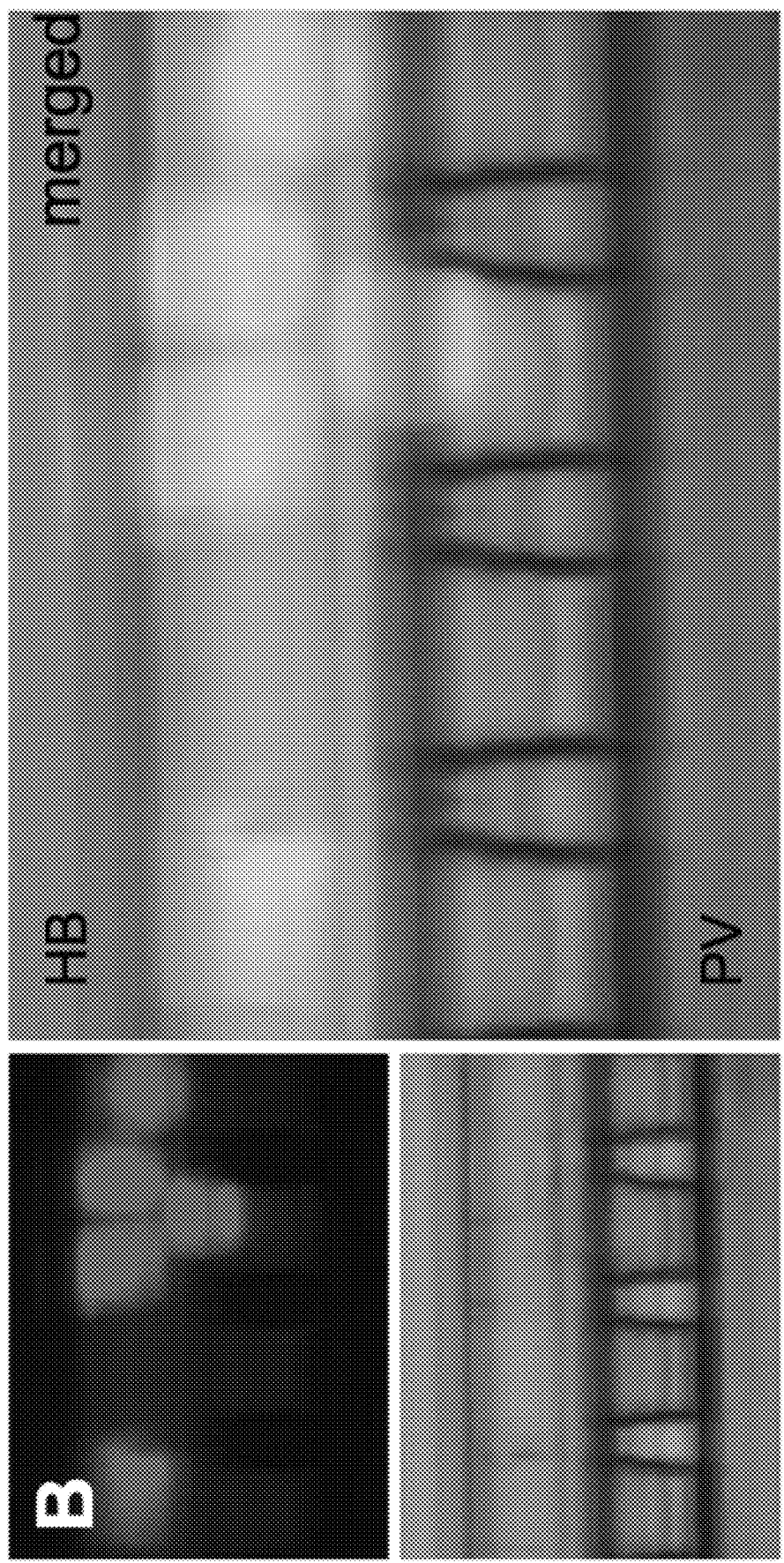
FIG. 12 illustrates another view of the exemplary microchannel device of FIG. 11.
Figures 13A, 13B:
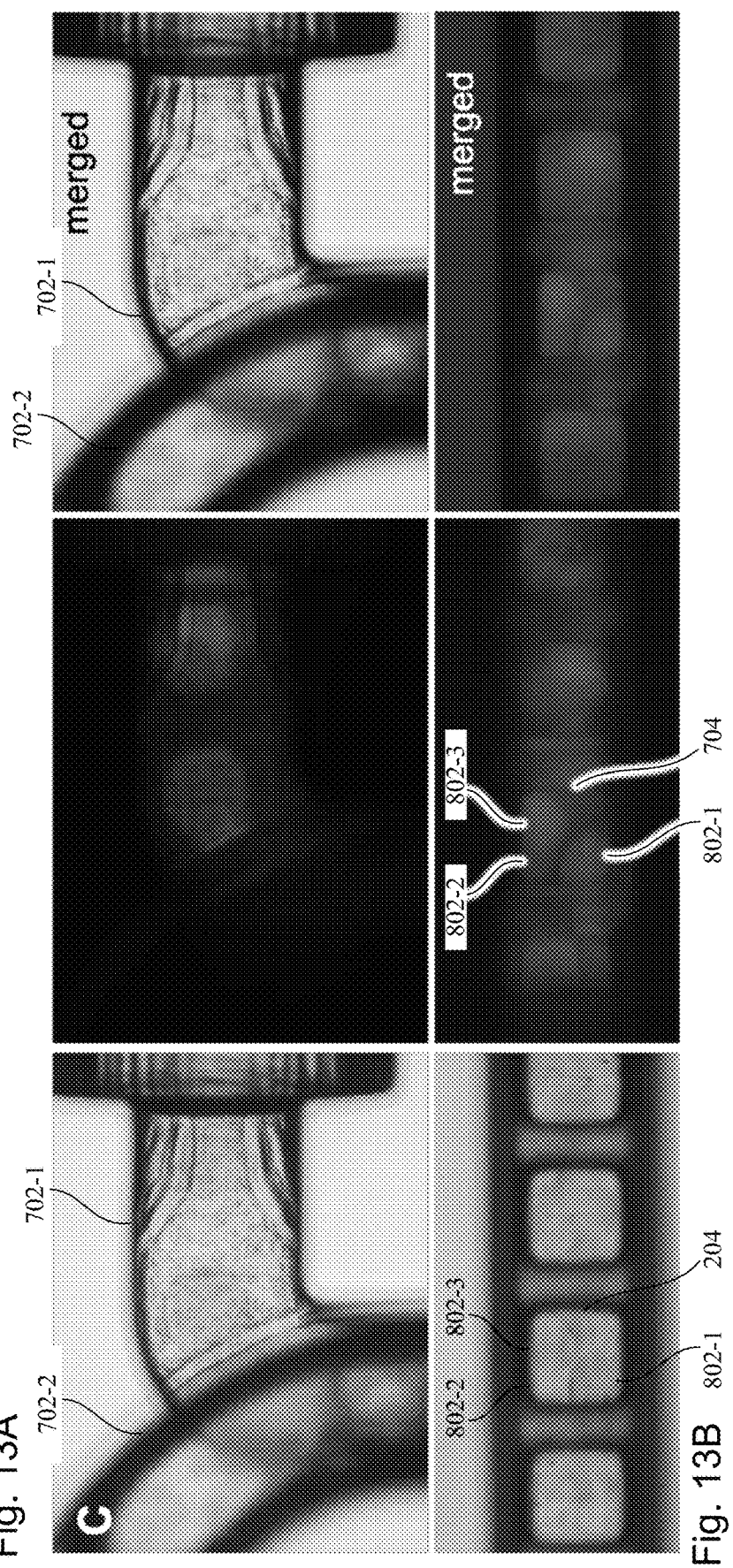
FIG. 13A illustrates yet another view of the microchannel device of FIG. 11 in which a first image and a second image are merged to highlight one or more microgel units in accordance with an embodiment of the present disclosure.
FIG. 13B illustrates yet another view of the microchannel device of FIG. 11 in which a first image and a second image are merged to highlight one or more microgel units in accordance with an embodiment of the present disclosure.

Accordingly, referring to FIG. 8 through FIG. 10, a method of fabricating the plurality of GelMA microgels via photomasking techniques will be described in accordance with embodiments of the present disclosure. In some embodiments, the photomasking techniques include forming a pre-polymer solution. Forming the pre-polymer solution includes dissolving GelMA in a buffer solution and adding a photoinitiator. In some embodiments, the buffer solution is phosphate-buffed saline (PBS). In some embodiments, the dissolving GelMA is in a range of from 5% wt/wt to 35% wt/wt, of from 7% wt/wt to 20% wt/wt, of from 10% wt/wt to 30% wt/wt, of from 15% wt/wt to 25% wt/wt, or of from 18% wt/wt to 22% wt/wt (e.g., 20% wt/wt). Furthermore, in some embodiments the photoinitiator is added at a range of from 0.5% wt/wt to 2% wt/wt of the pre-polymer solution, of from 0.5% wt/wt to 1.5% wt/wt of the pre-polymer solution, of from 1% wt/wt to 1.5% wt/wt of the pre-polymer solution, or of from 0.8% wt/wt to 1.2% wt/wt of the pre-polymer solution (e.g., 1% wt/wt). In some embodiments, the photoinitiator includes 2-hydroxy-1-(4-(hydroxyethoxy)phenyl)-2-methyl-1-propanone. In some embodiments, utilizing a lower parts by weight GelMA (e.g., 7% parts by weight as compared to 20% parts by weight GelMA) typically produces microgels that are more easily detachable from their fabricated environment as compared to higher parts by weight GelMA microgels. However, these lower parts by weight GelMA microgels often deform from their fabricated shape and/or degrade at a more rapid rate as compared to a higher parts by weight GelMA microgel. Likewise, the higher parts by weight GelMA (e.g., 20% parts by weight) produces microgels that are typically firm and/or do not stick to surrounding environments and structures, but may be difficult to detach from their fabricating environment. In some embodiments, the pre-polymer solution is formed with a degree of methacryloyl substitution of from about 75% to about 90%. As used herein, "GelMA_low" refers to a degree of methacryloyl substitution of less than or equal to about 80%, "GelMA_medium" refers to a degree of methacryloyl substitution of greater than about 80%, whereas "GelMA_high" refers to a degree of methacryloyl substitution of greater than about 90%.

In some embodiments, the photomasking techniques include fabricating and/or utilizing a photomask including an array of transparencies. Each transparency in the array of transparencies of the photomask forms at least one corresponding GelMA microgel. In some embodiments, the array of transparencies is formed as an array of circles (e.g., thin cylinders), which produces cylindrical or disc shaped microgels. Furthermore, in some embodiments each transparency is formed with a corresponding diameter in a range of from 50 µm to 750 µm, of from 50 µm to 650 µm, of from 100 µm to 650 µm, of from 100 µm to 500 µm, of from 150 µm to 650 µm, of from 150 µm to 550 µm, of from 200 µm to 550 µm, or of from 300 µm to 500 µm. Additional shapes and sizes of each transparency in the array of transparencies are utilizable in the present disclosure. In some embodiments, each transparency in the array of transparency is formed with a diameter that is approximately equal (e.g., within an acceptable range of tolerance, such as +10 µm), which allows for the photomask to produce multiple GelMA microgels of approximately equal size. Similarly, in some embodiments the array of transparencies includes a range of diameters, allowing the resulting GelMA microgels to be fabricated in a variety of size (e.g., in a range of from 300 µm to 500 µm).

In some embodiments, in order to fabricate the GelMA microgels, a predetermined amount (e.g., volume or mass) of the pre-polymer solution and the photoinitiator are disposed (e.g., pipetted) onto the first slide. In some embodiments, the predetermined amount is in a range of from 5 microliters (µL) to 1,000 µL, of from 5 µL to 750 µL, of from 10 µL to 500 µL, of from 10 µL to 250 µL, of from 10 µL to 150 µL, of from 10 µL to 100 µL, of from 5 µL to 100 µL, of from 10 µL to 80 µL, of from 20 µL to 75 µL, of from 25 µL to 75 µL, or, of from 35 µL to 65 µL (e.g., 50 µL). In some embodiments, the predetermined amount is a volume defined by an internal capacity (e.g., volume) of a contained structure formed by the slides (e.g., I an internal volume formed by internal surfaces of the slides). In some embodiments, the predetermined amount is a volume less than the volume of the contained structure (e.g., approximately 95% of the volume of the contained structure).

In some embodiments, an outer edge portion of the first slide surrounds one or more spacers. The one or more spacers provide a vertical separation (e.g., a height of the volume of the contained structure) between the first slide and a second slide, as well as aiding in the prevention of leaking of the solution. Furthermore, in some embodiments a second slide is disposed above the first slide upon completion of the disposal of the pre-polymer solution and the photoinitiator, forming the contained structure while also evenly distributing a film of the pre-polymer solution and the photoinitiator therein. By varying a size of the first slide and/or second slide, as well as the thickness (e.g., vertical separation formed) of the one or more spacers, the microgels may be formed with different aspect ratios. For instance, in some embodiments the thickness of the resulting microgel is in a range of from 50 μm to 1,000 μm, of from 50 μm to 750 μm, of from 150 μm to 750 μm, of from 100 μm to 650 μm, of from 150 μm to 650 μm, of from 100 μm to 550 μm, of from 150 μm to 550 μm, of from 150 μm to 500 μm, of from 100 μm to 450 μm, of from 150 μm to 450 μm, of from 200 μm to 500 μm, or of from 300 μm to 500 μm. Furthermore, in some embodiments a second slide is disposed above the first slide upon completion of the disposal of the pre-polymer solution and the photoinitiator, which forms a contained structure and an evenly distributes a film of the pre-polymer solution and the photoinitiator therein. By varying at least a size of the first slide and/or second slide, as well as the thickness of the one or more spacers, the microgels are configurable with different aspect ratios.

In some embodiments, the photomask is disposed to a top surface of the second slide. Accordingly, the photomask and the contained structure are exposed to UV light for a predetermined period of time, allowing the transparencies of the photomask to permit UV light to pass through while simultaneously blocking the remainder of the UV light. In some embodiments, the predetermined period of time is less than or equal to about 30 seconds. In some embodiments, the predetermined period of time is in a range of from 1 second to 180 seconds, of from 1 second to 150 seconds, of from 1 second to 120 seconds, of from 10 seconds to 120 seconds, of from 1 second to 90 seconds, of from 1 second to 60 seconds, of from 5 seconds to 60 seconds, of from 5 seconds to 50 seconds, of from 5 seconds to 40 seconds, of from 10 seconds to 40 seconds, of from 5 seconds to 30 seconds, or of from 10 seconds to 30 seconds. In some embodiments, the light has a wavelength in a range of from 10 nanometers (nm) to 480 nm, of from 100 nm to 480 nm, of from 100 nm to 400 nm, of from 200 nm to 480 nm, of from 200 nm to 400 nm, of from 300 nm to 480 nm, of from 300 nm to 400 nm, or of from 350 nm to 400 nm (e.g., a wavelength of 365 nm). Furthermore, in some embodiments the ultraviolet light has an intensity in a range of from 10 milliwatts per cubic centimeter (mW cm$^{-3}$) to 15 mW cm$^{-3}$, of from 10.5 mW cm$^{-3}$ to 14.5 mW cm$^{-3}$, of from 11 mW cm$^{-3}$ to 14 mW cm$^{-3}$, of from 11.5 mW cm$^{-3}$ to 13.5 mW cm$^{-3}$, of from 12 mW cm$^{-3}$ to 13 mW cm$^{-3}$, or of from 12.2 mW cm$^{-3}$ to 12.8 mW cm$^{-3}$ (e.g., 12.4 mW cm$^{-3}$). The exposure to UV light enables crosslinking of the pre-polymer solution, which in turn generates the GelMA microgels.

In some embodiments, the contained structure is at least partially disassembled (e.g., broken down) in order to retrieve the GelMA microgels, which can mark completion of the fabrication of the plurality of GelMA microgels. In some embodiments, the fabricated GelMA microgels is formed as a connected structure (e.g., a network or matrix of microgels) and require physical separation in order to ensure that the GelMA microgels properly flow within the device and plug the intermediate channels. For instance, in some embodiments fabrication of the GelMA microgels produces spars that interconnect the microgels. Accordingly, in some embodiments the retrieving of the GelMA microgels includes transferring the generated GelMA microgels into a mineral oil bath, which is subjected to a mechanical agitation (e.g., agitation to remove spars or dislodge microgels). In some embodiments, the agitating of the mineral oil bath includes agitating with a pipette (e.g., stirring a pipette in a back-and-forth and/or circular motion). In some embodiments, the agitating of the mineral oil bath includes sonication. Furthermore, in some embodiments the agitating of the mineral oil bath includes utilizing a magnetic stirrer. The above described agitating includes manual agitation and/or automatic agitating (e.g., agitating conducted using an automated system).

In some embodiments, retrieval of the fabricated GelMA microgels from the slides and/or the spacer of the contained structure requires treatment (e.g., preconditioning) of the slides and/or the spacer prior to disposal of the pre-polymer solution. For instance, in some embodiments failure to treat the slides and/or the spacer of the contained structure results in fabricated microgels that fail to detail from the respective slides (e.g., the fabricated microgels are sticky). Accordingly, in some embodiments the retrieval of the GelMA microgels includes immersing the slides and/or the spacer in a sodium hydroxide (NaOH) solution. In some embodiments, the slides and/or spacer are immersed for a predetermined period of time. In some embodiments, this predetermined period of time for immersion is in a range of from 5 minutes to 60 minutes, of from 5 minutes to 50 minutes, of from 10 minutes to 45 minutes, of from 20 minutes to 40 minutes, or of from 25 minutes to 35 minutes (e.g., 30 minutes). Subsequent immersion of the slides and/or the spacer in the sodium hydroxide solution, the slides and/or the spacer are immersed in an ethyl alcohol solution. Subsequently, the immersed slides and/or the spacer are subjected to sonication for a predetermined period of time, which forms a sonicated slide and/or spacer. In some embodiments, this predetermined period of time for in a range of from 5 minutes to 60 minutes, of from 5 minutes to 50 minutes, of from 10 minutes to 45 minutes, of from 5 minutes to 30 minutes, or of from 5 minutes to 20 minutes (e.g., 15 minutes).

Moreover, in some embodiments to promote retrieval (e.g., detachment) of the fabricated microgels, prior to the disposing the pre-polymer solution, for at least one slide and/or the spacer, the method further includes preparing a stock solution of about 0.5 wt % of methoxy polyethylene glycol 5000 Si (mPEG5000-Si), about 1 wt % acetic acid, and ethyl alcohol. A sample of the stock solution is disposed onto the at least one slide and/or spacer. In some embodiments, the sample has a volume in a range of from 5 μL to 500 μL, of from 5 μL to 250 μL, of from 10 μL to 250 μL, of from 5 μL to 100 μL, of from 10 μL to 100 μL, of from 5 μL to 750 μL, of from 25 μL to 70 μL, or of from 40 μL to 60 μL (e.g., 50 μL). In some embodiments, a size of a sample will depend on a size of a respective slide and/or spacer. Nevertheless, the at least one slide and/or the spacer is subjected to a heated environment for predetermined period of time, which forms an incubated slide and/or spacer. In some embodiments, the heated environment has a temperature of from 50° C. to 110° C., of from 50° C. to 100° C., of from 50° C. to 90° C., of from 60° C. to 100° C., of from 50° C. to 80° C., or of from 65° C. to 75° C. (e.g., 70° C.). Further, in some embodiments the predetermined heating period of time is in a range of from 5 minutes to 60 minutes, of from 5 minutes to 50 minutes, of from 10 minutes to 45 minutes, of from 20 minutes to 40 minutes, or of from 25 minutes to 35 minutes (e.g., 30 minutes). Nevertheless, the incubated slide and/or spacer is immersed in deionized water, which forms an immersed slide and/or spacer. This immersed slide and/or spacer is subjected to sonication each respective immersed slide and/or spacer for a predetermined period of time, which forms a sonicated slide and/or spacer. In some embodiments, this predetermined period of time in a range of from 5 minutes to 60 minutes, of from 5 minutes to 50 minutes, of from 10 minutes to 45 minutes, of from 5 minutes to 30 minutes, or of from 5 minutes to 20 minutes (e.g., 15 minutes). Furthermore, the sonicated slide and/or spacer is dried, thus forming a prepared slide and/or spacer that is ready for future use in fabricating the GelMA microgels. In some embodiments, the drying of the sonicated slide and/or spacer is conducted via a desiccator.

In some embodiments, the plurality of GelMA microgels is fabricated using a microfluidic technique. Microfluidic techniques include suspending a first solution (e.g., GelMA) in a second solution (e.g., a non-reactive fluid, such as mineral oil or glycerin) to form a suspension of droplets of the first solution. In some embodiments, the droplets are formed using a combination of channels that focus a flow of the first solution and the second solution. For instance, a first channel produces a stream of GelMA and a second channel and a third channel, each being orthogonal to the first channel, producing a stream of the second solution. The streams of the second solution assist in forming the droplets of the first solution. The droplets are further exposed to UV light to formed fabricated GelMA microgels. In some embodiments, one or more GelMA microgel in the plurality of GelMA microgels is formed as a sphere or spheroid. In some embodiments, the plurality of GelMA microgels includes a combination of cuboid microgels, cylindrical microgels, and/or spherical (e.g., spheroid) microgels. Furthermore, in some embodiments the plurality of GelMA microgels includes one or more microgels in a shape of a pyramid.

Furthermore, in some embodiments of the present disclosure the microgels include one or more pluronic hydrogel microgels. In some embodiments, the pluronic microgels are fabricated via a process including dissolving pluronic F127 (pl F127), which is a tri-block copolymer of poly(ethylene oxide) and poly(propylene oxide) of a nominal formula EO100-PO65-EO100, in pure water (e.g., deionized water) similar to the above described dissolving of GelMA. Accordingly, in some embodiments fabricating the pluronic F127 GelMA includes dissolving pluronic F127 in a 10% wt phosphate buffered saline (PBS) solution including about 0.25% photoinitiator. In some embodiments, the dissolving includes approximately 20 wt % pluraonic F127 in deionized water. In some embodiments, the dissolving includes using an organic solvent (e.g., hexane, toluene, chloroform (CHCl$_3$), dichloromethane, acetone, dimethylsulfoxide (DMSO), etc.) as a solution bath. In some embodiments, the solution bath includes a non-organic solution and/or non-aqueous solution (e.g., an oil-phase solution such as mineral oil, olive oil, glycerin, etc.). Furthermore, in some embodiments a size of one or more microgels in the plurality of microgels is determined according to an agitation mechanism during the fabricating of the microgels. For instance, in some embodiments a slower rate of stirring (RPM) (e.g., 4 RPM) produces a larger microgel. Moreover, in some embodiments a surface tension reducer surfactant (e.g., polysorbate 20 (TWEEN 20)) and/or an emulsifier (e.g., sorbitan monostearate (SPAN 60)) are included in the fabricating of the microgels to increase stability of the microgels.

In some embodiments, one or more microgels in the plurality of microgels is fabricated using additive manufacturing. In some embodiments, the one or more microgels includes poly(lactic-co-glycolic acid), PGLA, polycaprolactone (PCL), or a similar polymer. In some embodiments, the one or more microgels include GelMA, fibrin, and collagen.

In some embodiments, in order to retard and/or arrest flow within the intermediate channels of the device, the plurality of GelMA microgels is suspended within a first solution. In some embodiments, the first solution includes the suspension of the plurality of microgels in a range of from 10 microgels per mL of working solution to 10,000 microgels per mL of working solution, of from 10 microgels per mL of working solution to 5,000 microgels per mL of working solution, of from 100 microgels per mL of working solution to 5,000 microgels per mL of working solution, of from 500 microgels per mL of working solution to 5,000 microgels per mL of working solution, of from 100 microgels per mL of working solution to 2,500 microgels per mL of working solution, of from 500 microgels per mL of working solution to 2,500 microgels per mL of working solution, of from 500 microgels per mL of working solution to 2,000 microgels per mL of working solution, of from 500 microgels per mL of working solution to 1,500 microgels per mL of working solution, or of from 750 microgels per mL of working solution to 1,250 microgels per mL of working solution (e.g., approximately 1,000 microgels per mL of working solution). In some embodiments, once the suspension of the plurality of GelMA microgels in the first solution is formed, the suspension of the plurality of GelMA microgels in the first solution is perfused through the first channel of the device. Perfusion of the suspension of the plurality of GelMA microgels in the first solution causes one or more GelMA microgels in the plurality of GelMA microgels to retard and/or arrest flow in at least one of the one or more intermediate channels. In some embodiments, a single GelMA microgel is sufficient to retard and/or arrest flow in a respective intermediate channel. In some embodiments, a plurality of GelMA microgels is sufficient to retard and/or arrest flow in a respective intermediate channel. For instance, in some embodiments a respective GelMA microgel in the plurality of GelMA microgels has a size (e.g., diameter) approximately equal to that of an intermediate channel. Accordingly, the respective GelMA microgel deforms at and/or lodges within an opening of the intermediate channel in order to retard and/or arrest flow within the intermediate channel. In some embodiments, a respective GelMA microgel in the plurality of GelMA microgels has a size that is less than that of an opening of an intermediate channel. Accordingly, one or more GelMA microgels flow into the opening of the intermediate channel and become lodged within the intermediate channel, thereby retarding and/or arresting flow in the intermediate channel. For instance, referring briefly to FIG. 7B, a structure of one or more intermediate channels 704 includes at least three GelMA microgels 802 (e.g., first GelMA microgel 202-1, second GelMA microgel 802-2, and third GelMA microgel 802-3) which retard and/or arrest flow within the intermediate channel. Once retarding or arresting of the flow of the medium through the intermediate channels of the device is no longer required, the microgels retarding or arresting the flow may be removed. In some embodiments, removal of the microgels includes applying a flow of fluid through the device such that a pressure differential is formed that promotes dislodging of the microgels. Similarly, in some embodiments, removal of the microgels includes allowing a period of time to elapse such that the microgels degrade within the device (e.g., according to the rate of degradation of the microgels).

In some embodiments, subsequent to the perfusion of the suspension of the plurality of GelMA microgels in the first solution through the first channel of the device, a flow of fluid (e.g., medium) is applied to the second channel of the device. This flow of fluid creates a pressure differential between the first channel and the second channel of the device, which promotes the GelMA microgels to flow into and retard and/or arrest flow in the one or more intermediate channels. In some embodiments, this pressure differential is required to dispose a GelMA microgel within an intermediate channel since a force of gravity is insufficient to promote retarding or arresting flow in the intermediate channels via the GelMA microgels.

Referring to FIG. 11 through FIG. 13, and FIGS. 31A, 31B, and 31C, various views of a microchannel vascular network device filled with GelMA microgels are depicted. As depicted in FIG. 11 through FIG. 13, FIGS. 31A, 31B, and 31C a first channel is filled with a plurality of GelMA microgels 802, which subsequently retard and/or arrest flow in one or more intermediate channels 704 (e.g., structures).

Accordingly, the GelMA microgels of the present disclosure allow for a temporary retarding and/or arresting of flow within microchannels of various devices. The GelMA microgels are capable of being fabricated through a variety of techniques and in a wide array of shapes and sizes, allow flows to be retarded and/or arrested according to goal a designer of the present disclosure.

Furthermore, since the GelMA microgels are degradable the retarding and/or arresting of flow within the device is may be temporary, expanding upon the uses of such devices.

PLGA Arresting Flow. As a non-limiting example, PLGA degrades by hydrolysis of its ester linkages in the aqueous solution producing PLA and PGA monomers. In some embodiments, an initial average size of PLGA microspheres is about 533.7±58.62 μm on day 0, and decreased to a size of about as 520.6±117.04 μm after 24 hours in culture, and 509.9±63.24 μm after 48 hours in culture. These microspheres continued decreased following 8 days, which indicates the hydrolysis of PLGA microspheres in PBS solution (FIG. 1B). However, the mean diameter was increased on Day 11 and maintained its increase, which indicates swelling of microspheres whereas degradation continued throughout the culture period. As previously described, swelling is an important process during PLGA microspheres degradation which is caused by water diffusion (e.g., water uptake) from outside and inside due to the increased osmotic pressure. On day 16, microspheres were completely divided into small fractures due to the degradation process. On day 22, the PLGA microspheres were no longer maintained their spherical shape and the polymer itself completely spread and attached to the surface of 96-well plate and remained the same. Accordingly, the microspheres of the present disclosure allow for an arresting and/or a retarding of a flow within a microchannel device.

Various aspects of the present disclosure are directed to providing a system for directing flow of a medium through one or more devices. The system includes one or more devices configured to have the medium flow therethrough. The arrangement and flow of medium through the one or more devices is configurable such that the system provides a supply of nutrients and/or a removal of waste from various cells nurtured within the one or more devices depending on the arrangement of the system.

The device(s) of the present disclosure include a channel having an inlet and an outlet. Interposing the inlet and the outlet of the device is a well configured to accommodate an insert that includes a structure for culturing cells. In some embodiments, the inlet and the outlet of the device are generally tubular in shape and have the same internal diameter. Further, in some embodiments the inlet and the outlet of the device include a planar flow nozzle disposed within the respective channel. The planar flow nozzle causes the medium flowing within the system to have a planar, or a linear, flow path. In an exemplary embodiment, the planar flow path provides a substantially consistent velocity of flow of medium within the system. Generally, the velocity of the medium within a respective device determines a concentration of nutrients that are received by the cells of the respective device. This consistent velocity provides a consistent flow rate, and thus a consistent concentration of nutrients and/or waste material, throughout the one or more devices of the system. Accordingly, in some embodiments a device of the present disclosure is symmetrical about a vertical axis. In some embodiments, the flow of the medium is a laminar flow throughout the devices of the system.

Figure 14:
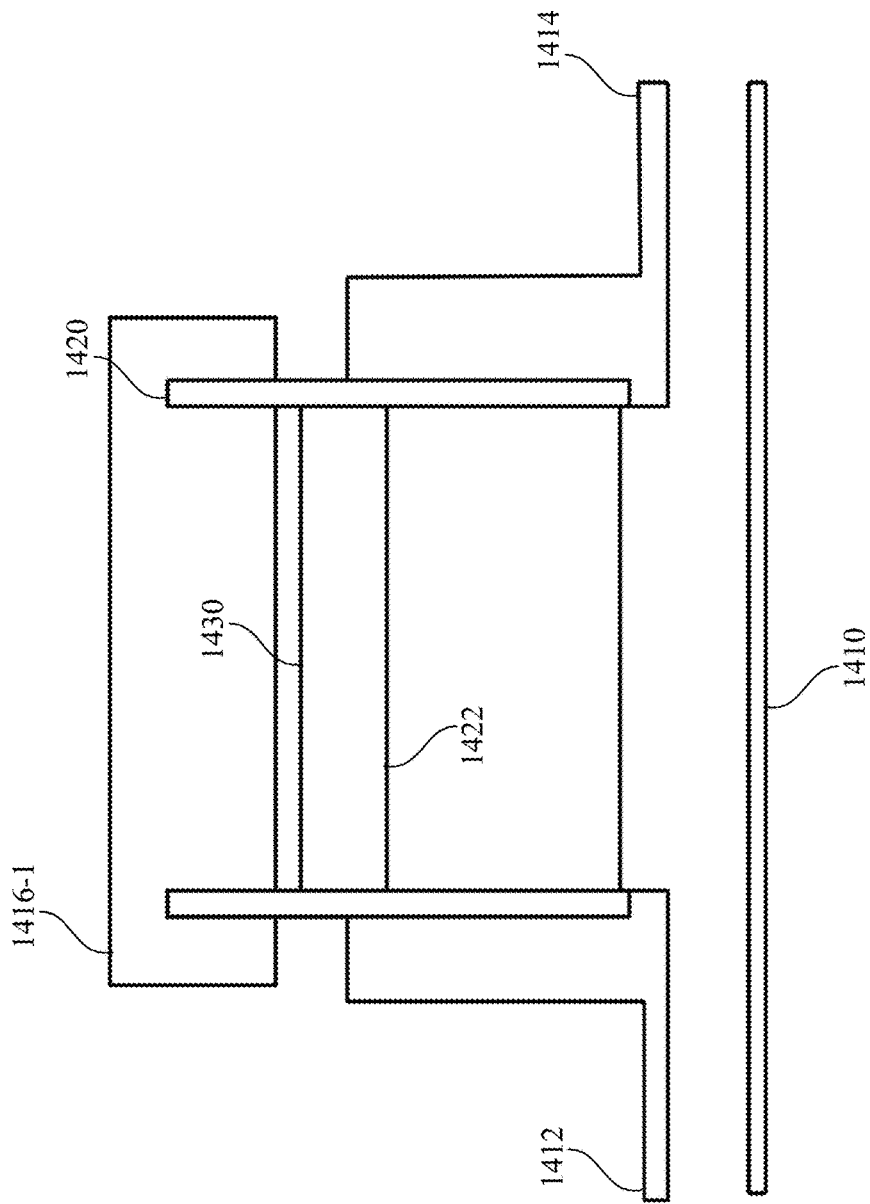
FIG. 14 illustrates an exemplary microchannel vascular network device, in accordance with an embodiment of the present disclosure.
Figure 15:
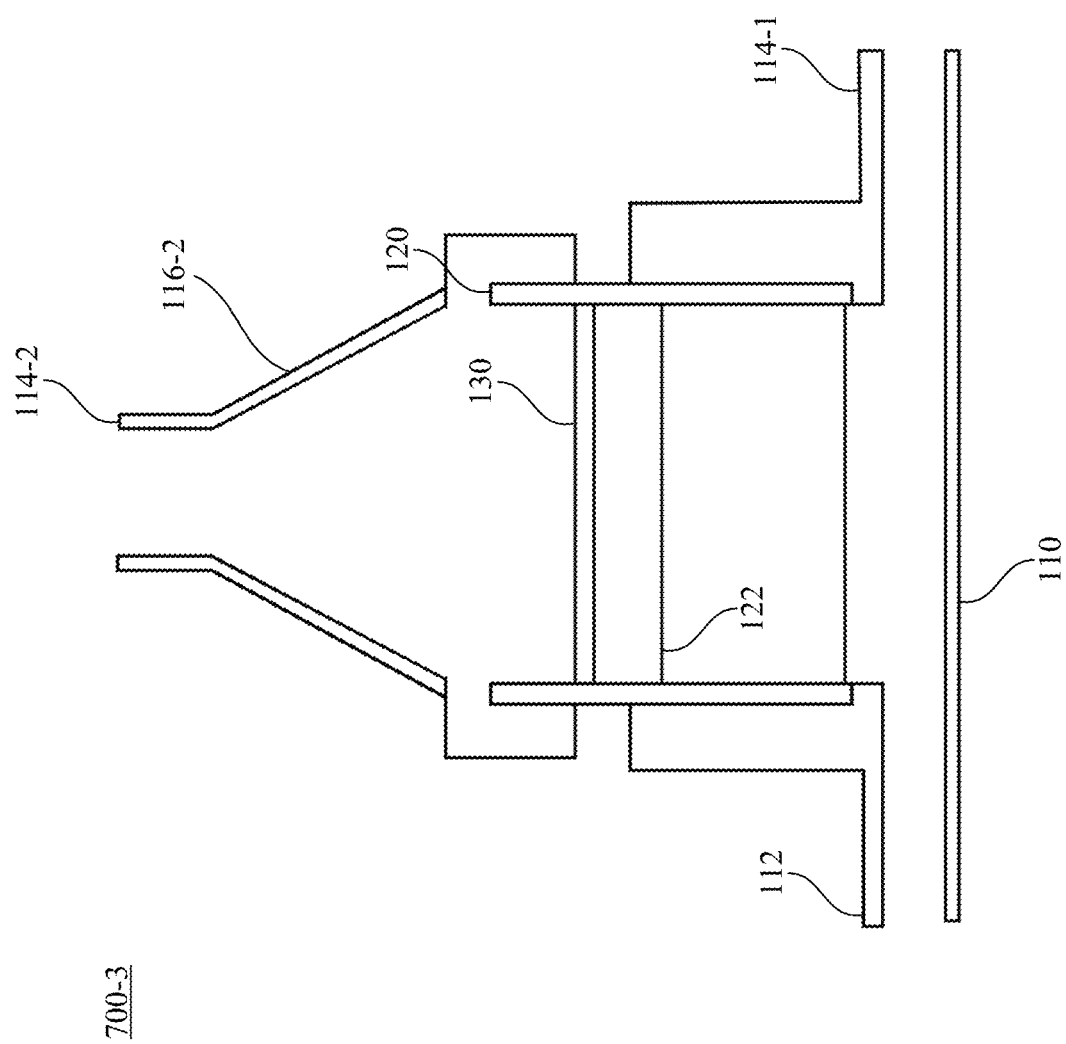
FIG. 15 illustrates another exemplary microchannel vascular network device, in accordance with an embodiment of the present disclosure.

Referring to FIG. 14, an exemplary microchannel vascular network device 700-2 of the present disclosure is illustrated. Device 700-1 includes channel 110 that accommodates a flow of medium 130 through the device. Channel 100 includes inlet 112 at a first end portion of the channel and at least outlet 114 at a second end portion of the channel. In some embodiments, one or more of the inlet and the outlet of the device is configured to couple with a silicon tubing through which the flow of the medium traverses. For instance, in some embodiments an end portion of either the inlet or the outlet is received by the silicon tubing (e.g., the end portion of either the inlet or the outlet is a male portion that is received by the silicon tubing), which forms a seal between the tubing and the inlet or outlet of the channel. In some embodiments, the silicon tubing is received by an end portion of either the inlet or the outlet (e.g., the end portion of either the inlet or the outlet is a female portion). In some embodiments, the channels of respective devices couple to each other through a plurality of connection pins (e.g., corresponding female and male connection pins).

In some embodiments, the device includes a well configured to accommodate an insert for culturing cells. The well interposes between the inlet and the outlet of the channel, such that the medium of the system flows from the inlet, through at least a portion of the well, and towards the outlet of the device. In some embodiments, the channel of the device is coupled to the well using a plurality of metal connection pins which minimizes a risk of accidental decoupling between the components of the device. In some embodiments, the channel of the device is coupled to the well via a reversible fastening or joint, such as a leur lock. In some embodiments, the channel of the device is coupled to the well via a standardized fitting. For instance, in some embodiments the standardized fitting is as specified by the International Organization for Standardization (ISO) 80369, (2017), "Small bore connectors for liquids and gases in healthcare applications," ISO/TC 210 Quality management and corresponding general aspects for medical devices, ICS 11.040.25, Print.

Figure 41:
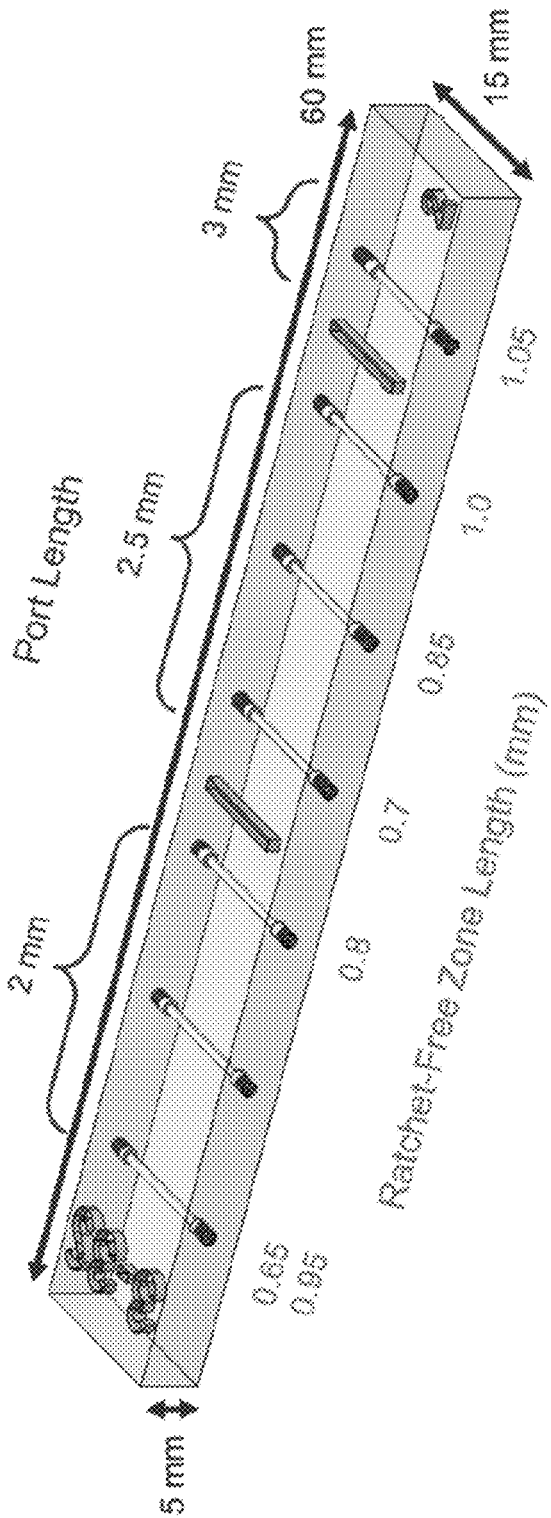
FIGS. 41 and 42 illustrate a connector for coupling a microchannel vascular network device with a bioreactor system, in accordance with embodiments of the present disclosure.
Figure 42:
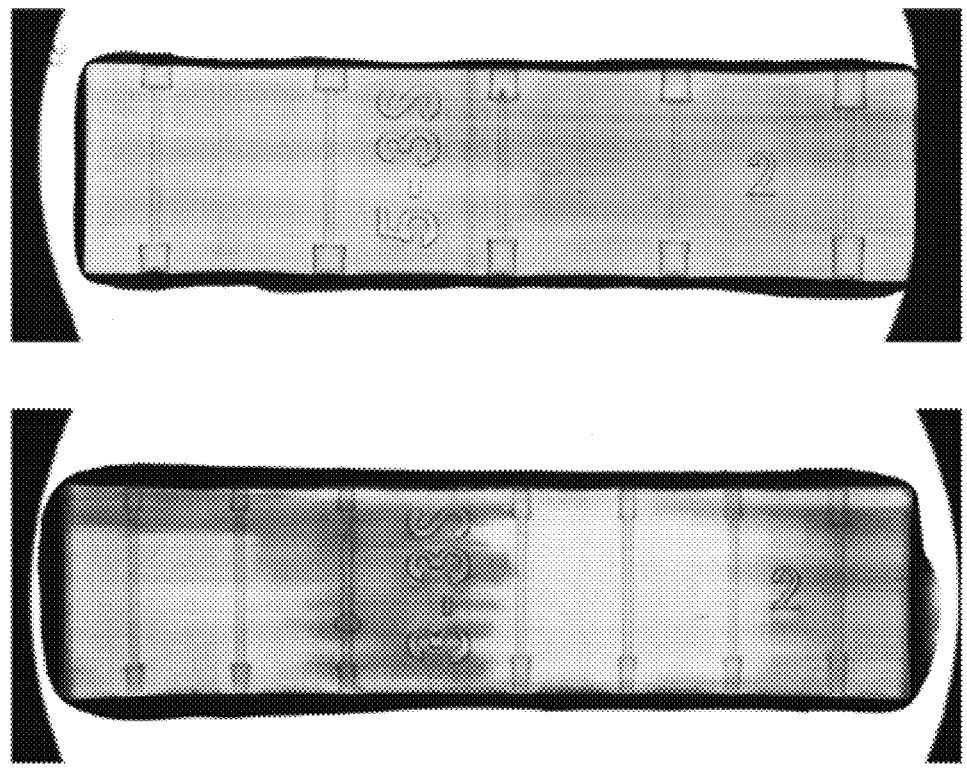

Referring to FIGS. 41 and 42, in some embodiments, the bioreactor system includes a plurality of connectors, which facilitate coupling a respective microchannel vascular network device with the bioreactor system. As illustrated, a plurality of ratchet free zones allow for an integer number of ratchets in utilizing the coupler. In some embodiments, a port length (e.g., larger diameter portion) of the coupler is about 0.3 mm to about 1.8 mm. In some embodiments, the port length is 0.5 mm, 0.8 mm, or 1.8 mm (e.g., corresponding to a predetermined size of tubing, such as size #3 or #5 tubing).

Furthermore, in some embodiments, the bioreactor system includes an enclosure, or is contained within an enclosure. In this way, the bioreactor system is sealed from an environment, which protects internal features of the bioreactor system from contamination. For instance, in some embodiments, a PMMA enclosure encompasses the bioreactor system, such that the pumps have appropriate openings for coupling to one or more components, such as a microchannel device and/or to dispose filters for a gas exchange (e.g., HEPA filters), as well as one or more ports (e.g., coupler) to allow for a flow of culture media to and/or from inlet and outlets channels of a microchannel device.

In some embodiments, the well is configured to accommodate a cell culture insert within a cavity of the well. The insert includes a structure for seeding a plurality of cells and other biological materials. In some embodiments, the insert includes a plurality of feet that protrude outwardly from a lower end portion of the insert. The plurality of feet of the insert rest against an edge portion of the well, which in turn provides a spacing between the well and the insert. The spacing accordingly allows for a flow of the medium between the channel, the well, and the insert of the device. Alternatively, the cell culture insert can be a hanging insert (e.g., the insert rests against an upper end portion of the well), or other type of insert that does not require feet in order to provide adequate spacing for fluid flow and drainage. Moreover, the edge portion of the well can include a plurality of spacers that the insert sits upon to provide adequate spacing for the flow and drainage of the medium within the device. Nevertheless, in some embodiments a portion of the insert includes a membrane, such as a semi-permeable membrane. When the insert includes living cells, a nutrient gradient will exists between the cells and the medium, thus the membrane provides a diffusion of medium through the membrane driven by the nutrient gradient. In some embodiments, a lower end portion of the insert includes a membrane. In some embodiments, one or more sidewalls of the insert includes a membrane. The well is in communication with the channel, and a caplet is disposed above the cell culture insert of the well to control the flow path of the medium therein.

In some embodiments, the insert is a polystyrene insert. In some embodiments, the insert of the well includes a height of about 10.5 millimeters (mm). In some embodiments, the insert of the well includes a height in a range of from 9 mm to 11 mm. In some embodiments, the insert is of a diameter of about 12 mm. In some embodiments, the insert is of a diameter in a range of from 10 mm to 14 mm, 11 mm to 13 mm, or 11.5 mm to 12.5 mm. Furthermore, in some embodiments, the insert of the well includes a plurality of pores. The pores of the insert are configured to allow for an exchange of materials between the cells retained in the insert and the medium of the system (e.g., provide nutrients and/or remove waste). In some embodiments, the insert is configured to accommodate an object (e.g., a plurality of cells, a sponge, hydrogel, etc.) that has a volume of approximately 1,000 cubic millimeters ($mm^3$). In some embodiments, the insert is configured to accommodate an object that has a volume in a range of $1*10-12$ $mm^3$ to 1,500 $mm^3$, $1*10-5$ $mm^3$ to 1,500 $mm^3$, or 1 $mm^3$ to 1,500 $mm^3$. In some embodiments, the insert is configured to an object that has a cross-sectional area in a range of 1 $mm^{-3}$ to 200 $mm^2$, 1 $mm^2$ to 150 $mm^2$, or 1 $mm^{-2}$ to 100 $mm^2$.

The systems and methods of the present disclosure are configured to culture cells that, in some embodiments, occupy a large spatial region (e.g., a cross sectional area of at least 100 $mm^2$). In some embodiments, the insert of the well is an insert and/or a membrane as provided by MilliporeSigma of 400 Summit Drive, Burlington, MA 01803. In some embodiments, the insert includes a membrane. For instance, in some embodiments the insert is configured to accommodate a membrane that further includes the plurality of cells. Likewise, in some embodiments the insert itself includes a membrane portion that allows for an exchange of material between the medium and the plurality of cells. Nevertheless, in some embodiments, the insert includes a mesh portion to allow a flow of the medium through the insert while preventing cells from escaping. In some embodiments, an upper portion of insert (e.g., a portion of the insert proximate to the caplet of the device), a lower portion of the insert (e.g., a portion of the insert proximate to the channel of the device), or both the upper portion and the lower portion of the insert includes a mesh. For instance, in some embodiments the insert includes a mesh with a mesh opening of approximately 30 nanometers (nm), approximately 40 nm, approximately 50 nm, approximately 60 nm, approximately 70 nm, approximately 80 nm, or approximately 90 nm. In some embodiments, the insert includes a mesh with a mesh opening in a range of approximately 50 nm to 1,000 nm, approximately 50 nm to 200 nm, or approximately 60 nm to 150 nm. Nevertheless, the systems and methods of the present disclosure are capable of culturing cells within a respective device that have a relatively large mass (e.g., a mass with a volume of from approximately 500 $mm^3$ to 1,000 $mm^3$). This relatively large mass allows for the system to culture cells with a physiologically relevant mass as well as culturing multiple cell types within one system, whereas previous systems were only capable of culturing spheroid masses or models.

As illustrated in FIG. 1A, device 100-1 includes well 120 that is configured to accommodate insert 122. Medium 130 is received through inlet 112 of the device, flows through well 120, at least partially through insert 122, and exits via outlet 114. As evident in FIG. 1A, device 100-1 is symmetric about a vertical axis, such that flow conditions within the device are uniform about a planar axis. This planar flow of the medium allows for the cells of the insert to receive a uniform and consistent concentration of nutrition.

In some embodiments, a device of the present disclosure includes a caplet that is disposed above the well of the device. The caplet is configured to seal at least a portion of the device (e.g., the well of the device) from an external environment (e.g., prevents contamination of the medium and/or cells) and, since, in some embodiments, the caplet is removably coupled to the device, facilitates manipulation and observation of the insert within the device (e.g., installation of the insert, inspection of cells cultured in the insert, removal of the insert, etc.). In some embodiments, the caplet is accommodated by the well (e.g., a portion of the caplet couples to an inner edge portion of the well). For instance, in some embodiments the caplet includes a female portion configured to receive a corresponding male portion of the well. In some embodiments, the caplet and the well of a device include corresponding threaded portions, such that the caplet and the well are coupled via a rotating motion of the corresponding threaded portions. Nevertheless, the coupling of the caplet and the well is preferably conducted using a mechanism (e.g., press fit, threading, etc.) that prevents contamination of the medium and the cells, while also preventing the medium from leaking externally from the device, or prevents fluids from entering the device.

In some embodiments, the caplet is configured to provide an additional flow path of the medium through the device. For instance, in some embodiments the caplet includes a second outlet configured to provide an additional flow path for the medium within the device to traverse. For instance, in some embodiments the flow of medium through a first outlet (e.g., the outlet of the channel), is blocked or retarded, such that the medium through the device flows from the inlet, through the well, and towards the second outlet of the caplet. In some embodiments, the medium flows from the inlet, through the well, and towards both the first outlet of the channel and the second outlet of the well. In some embodiments, the medium flows from the inlet, through the well, and selectively towards either or both of the first outlet of the channel and the second outlet of the well. This selective flow is dependent upon on a pressure gradient provided by one or more pumps of the system (e.g., a suction pressure of a pump coupled to the respective outlet). In some embodiments, the first inflow opening and the second outflow opening each comprise a fastening mechanism configured to removably couple the microchannel vascular network device with the pump.

In some embodiments, the second outlet of the caplet includes a decrease in internal diameter from a first diameter to a second diameter. Accordingly, the second outlet of the caplet decreases from a first diameter, which, in some embodiments, is approximately equal to a diameter of the well, to a second diameter, which is approximately equal to an internal diameter of the inlet of the device. In some embodiments, the decrease in internal diameter of the caplet from the first diameter to the second diameter is a linear decrease (e.g., the decrease occurs over a linear slope). In some embodiments, the decrease is a discrete (e.g., abrupt or stepped) decrease in diameter. Nevertheless, the decrease in internal diameter of the outlet of the caplet focuses (e.g., converges) the flow path of the medium through the device while maintaining the planar flow characteristics therein (e.g., maintaining a laminar planar flow path). In some embodiments, the second outlet of the caplet includes the same coupling mechanism as described above with respect to the inlet and the outlet of the channel (e.g., a female to corresponding male coupling mechanism).

In some embodiments, the system includes one or more pumps configured to create a pressure differential within the system and provide a flow of the medium through the system. For instance, in some embodiments a pump is disposed upstream in the system in order to push (e.g., discharge), or drive, the medium through the system (e.g., a system as illustrated in FIG. 4A). In some embodiments, a pump is disposed downstream in the system in order to pull (e.g., suction), or draw, medium through the system (e.g., a system as illustrated in FIG. 4B). For instance, in some embodiments a pump is disposed downstream from an outlet of a channel of a respective device, which allows the medium to be drawn through the outlet (e.g., as illustrated by flow path 132-1 of FIG. 2). In some embodiments, a pump is disposed downstream from a second outlet of a caplet of a respective device, which allows for the medium to be drawn through the second outlet of the caplet (e.g., as illustrated by flow path 132-2 of FIG. 2). In some embodiments, a first pump is disposed downstream from an outlet of a channel of a device and a second pump is disposed downstream from a second outlet of a caplet of the device. This first and second pump configuration allows for the medium to be drawn through both the outlet of the channel and the second outlet of the caplet (e.g., the medium flows from the inlet of the device and exits from both the outlet of the channel and the outlet of the caplet as illustrated by flow paths 132-1 and 132-2 of FIG. 2). Depending on a configuration of each pump, the flow of medium drawn through each outlet of the device can be uniform (e.g., the same flowrate through both outlets) or non-uniform (e.g., a first flowrate of medium through the first outlet of the device and a second flowrate of medium, different than the first flowrate of medium, through the second outlet of the device). In some embodiments, the pump includes a maximum discharge pressure of approximately 200 kilo Pascal (kPa) or less, approximately 100 kPa or less, approximately 90 kPa or less, approximately 80 kPa or less, approximately 70 kPa or less or approximately 50 kPa or less. In some embodiments, the pump includes a maximum suction pressure of approximately 200 kilo Pascal (kPa) or less, approximately 100 kPa or less, approximately 90 kPa or less, approximately 80 kPa or less, approximately 70 kPa or less or approximately 50 kPa or less. In some embodiments, the pump is a Welco WPM2 pump (e.g., Welco WPM2-PIEA-CP pump as provided by Welco of 3-3-1 Sumiyoshi-cho, Fuchu-shi, Tokyo 183-0034, Japan.

In some embodiments, the system includes a controller configured to at least operate the one or more pumps of the system. Operation of the pumps includes controlling a power state of each respective pump (e.g., an ON state and an OFF state) as well as a flow rate provided by each respective pump (e.g., controlling a rotational velocity of a motor of each respective pump). This operation of the pumps can be conducted through various physical mechanisms, such as dials that configure the flow rate of each respective pump, as well as through instructions provided to the controller.

As previously described, in some embodiments of the present disclosure the system includes more than one device to allow for more than one cell cultures within the system. For instance, in some embodiments the system of the present disclosure includes a plurality of devices that can be disposed in a variety of configurations. In some embodiments, one or more devices in the plurality of devices is coupled with, and in communication with, one or more adjacent devices in the plurality of devices (e.g., the devices are coupled and in fluidic communication such that the medium of the system flows from a first device to a second device). In some embodiments, the plurality of devices of the system is coupled in parallel, such that an outlet of a respective channel of a first device is in communication with an inlet of a respective channel of a second device. Similarly, in some embodiments the plurality of devices of the system is coupled in series, such that the respective cells cultured in each device are isolated from the cells of another device in the plurality of devices (e.g., the medium flowing through a first device is isolated from the medium flowing through a second device). Likewise, in some embodiments the plurality of devices of the system includes at least a first subset of devices that is coupled in parallel and a second subset of devices that is coupled in series. Embodiments that utilize more than one device within a respective system allows for more than one type of cell to be cultured within the system and/or for determining an efficacy of a material on the cultured cells. For instance, a network of supply and outlet lines (e.g., silicon tubing) can be configured to connect a number of wells in series, enabling the system to model in vivo tissue conditions where nutrient and waste material concentrations vary in diminishing or increasing gradient fashion as would be the case across a spatial dimension of an organ.

Furthermore, in some embodiments, the system includes one or more reservoirs of medium. Each reservoir in the one or more reservoirs of the system is configured to accommodate a supple of the medium and/or various byproducts of the system (e.g., waste material, e.g., bile effluent, produced by the various cells maintained within the wells of the devices). For instance, in some embodiments the one or more reservoirs of the system includes a first reservoir that accommodates an initial supply of the medium (e.g., reservoir 200-1 of FIG. 4). In some embodiments, the one or more reservoirs of the system includes a second reservoir that accommodates collection of the medium or the waste products that have since flowed through the system or a respective device of the system (e.g., reservoir 200-2 of FIG. 4). In some embodiments, the system forms a closed loop such that the reservoir is configured to accommodate an excess of medium flowing through the system (e.g., reservoir 200 of FIG. 4D).

Figure 16:
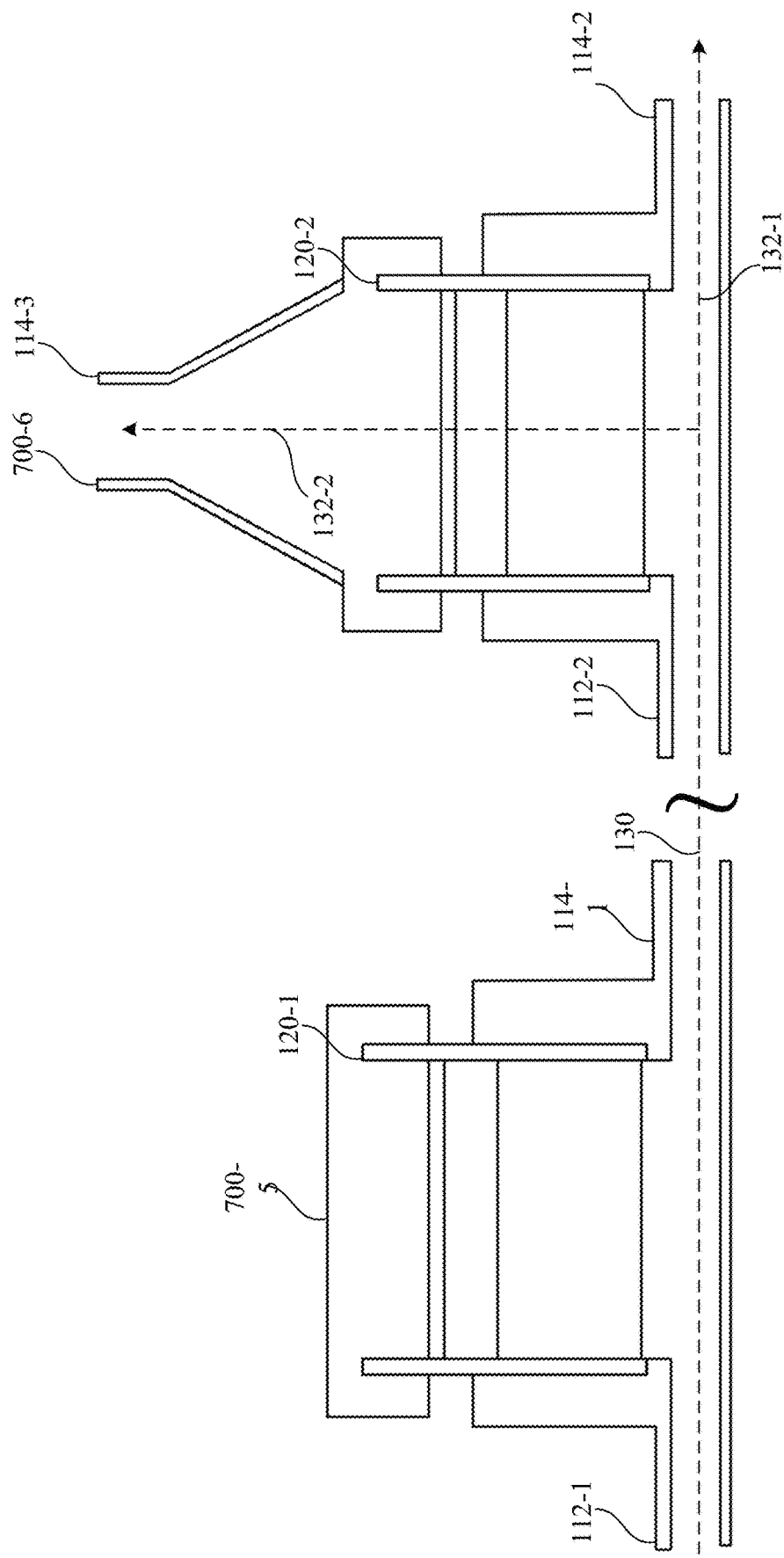
FIG. 16 illustrates a portion of a bioreactor system, in accordance with an embodiment of the present disclosure, in which dashed lines represent a general flow path of a culture medium.

Referring to FIG. 16, an embodiment of the system is illustrated in which first device 700-1 and second device 700-2 are coupled in parallel. In FIG. 16, the dashed line and arrows represents a flow path of medium 130 through the devices. As illustrated in FIG. 17, medium 130 is received via inlet 112-1 of first device 700-1, and flows through well 120-1 of the first device. Medium 130 is received by outlet 114-1 of first device 700-1, which is in turn received via inlet 112-2 of second device 700-2. Once medium 130 is received by well 120-2 of second device 700-2, the flow of the medium may continue either towards outlet 114-2 of the second device or towards outlet 114-3 of the caplet of the second device, depending on a pressure gradient within the second device. For instance, in some embodiments medium 130 continues through outlet 114-2 of second device 700-2, while waste produced by cells accommodated within well 120-2 is removed from the system via a flow through outlet 114-3 of the caplet of the second device.

Referring to FIG. 16, in some embodiments, the caplet of a device is coupled to the well via an O-ring. In some embodiments the caplet, the well, or both the caplet and the well include a groove that is configured to accommodate the O-ring. This O-ring is configured to create a seal between the caplet and the well of the respective device, ensuring that air, or a similar contaminant, does not enter the system and/or that the medium does not leak out of the system, thus isolating the system from an external environment (e.g., atmospheric conditions), and preserving the integrity of the environment internal to the device. To further ensure that the system is isolated from an external environment, in some embodiments each surface of the removable caplet that is in contact with at least a wall of the well includes a hydrophobic material. In some embodiments, this inclusion of the hydrophobic material includes coating each surface of the caplet that is in contact with at least a surface (e.g., a wall) of the well with the hydrophobic material (e.g., applying two coats of the hydrophobic material). For instance, in some embodiments the hydrophobic material is NeverWet®, provided by Rust-Oleum® of Vernon Hills, Illinois. In some embodiments, the O-ring includes a hydrophobic material (e.g., the hydrophobic material is coated on the O-ring). In some embodiments, the O-ring includes an inner diameter in a range of from 0.3 inches (in) to 0.7 in, of from 0.4 in to 0.6 in, or of from 0.4 in to 0.5 in. In some embodiments, the O-ring includes an inner diameter of 0.489 in. In some embodiments, the O-ring includes an outer diameter in a range of from 0.4 in to 0.8 in, of from 0.5 in to 0.7 in, or of from 0.6 in to 0.7 in. In some embodiments, the O-ring includes an outer diameter of 0.629 in.

As previously described, in some embodiments the system of the present disclosure is utilized for culturing cells and/or performing biological experiments on cells cultured within the system. Accordingly, in some embodiments the cell culture insert includes a sponge or a mesh that facilitates the culturing of cells. For instance, in some embodiments the sponge of the insert is a Type 1 collagen sponge, such as that prepared from a dermis of a pig. In some embodiments, the cell culture insert is a gelfoam, such as a cylindrical gel foam. In some embodiments, the cell culture insert is a gelfoam as provide by Pfizer of New York City, New York. Nevertheless, in some embodiments, the cell culture insert is coated in gelatin. For instance, in some embodiments the cell culture insert is coated with about 2% gelatin, about 1.5% gelatin, about 1% gelatin, about 0.5% gelatin, about 0.2% gelatin, about 0.1% gelatin, or about 0.05% gelatin.

Another aspect of the present disclosure is directed to providing a method of culturing cells. In some embodiments, the method utilizes an embodiment of a system as described above. Nevertheless, the method includes seeding a plurality of cells to be cultured within one or more devices of the system. In some embodiments, the seeding includes disposing an insert within a well of a respective device, in which the insert accommodates the cells. In some embodiments, the seeding includes suspending the cells within the medium of the system and subsequently flowing the medium through the system.

Accordingly, the method further includes flowing a culture medium through the system. In some embodiments, a plurality of cells is cultured in two dimensions within a respective device (e.g., cultured on a membrane of an insert). In some embodiments, a plurality of cells is cultured in three dimensions within a respective device (e.g., the plurality of cells is embedded within a cell scaffold device and/or included, e.g., suspended, in a hydrogel).

In some embodiments, prior to the seeding of the cells into the well of the device, the plurality of cells is generally preferred for culturing hepatocyte cells, as calcium aids in a compartmentalization of bile, and other similar products, to the canaliculi formed by the hepatocyte cells. In some embodiments, the plurality of cells is exposed to the solution for a predetermined time of about 20 minutes. Use of any beneficial exposure time is encompassed by the instant disclosure. For instance, in some embodiments the predetermined time is about 10 minutes. In some embodiments, the predetermined time is about 15 minutes. In some embodiments, the predetermined time is about 25 minutes. In some embodiments, the predetermined time is about 30 minutes.

In some embodiments, the plurality of cells is seeded in the well at a density of about $1*10^2$ cells per square centimeter, about $5*10^2$ cells per square centimeter, about $1*10^3$ cells per square centimeter, about $5*10^3$ cells per square centimeter, about $1*10^4$ cells per square centimeter, about $5*10^4$ cells per square centimeter, about $1*10^5$ cells per square centimeter, about $5*10^5$ cells per square centimeter, about $1*10^6$ cells per square centimeter, or about $5*10^6$ cells per square centimeter.

In some embodiments, the flowing of medium within the system is conducted at a flowrate of about 150 microliters per minute (μL/min), about 200 μL/min, about 250 μL/min, about 300 μL/min, about 350 μL/min, about 400 μL/min, about 450 μL/min, about 500 μL/min, about 550 μL/min, about 600 μL/min, about 650 μL/min, or about 700 μL/min. Generally, the flowing of medium within the system is conducted at a flowrate that mimics the flow of fluid within an organ, such that adequate nutrients and waste removal is provided to the cells of the system without damaging the cells.

Now that a general structure of various embodiments of the systems, devices, and methods of the present disclosure have been described, various examples of the present disclosure will now be described in detail.

Example I—Culturing of Hepatocyte Cells

A device of the system includes a plurality of hepatocyte cells accommodated in the respective insert. Upon introduction of a medium, the hepatocyte cells will produce a blood effluent and a bile effluent. Accordingly, pumps are coupled to the system such that an outlet of a channel of the device is configured to receive the blood effluent while the outlet of the channel is configured to receive the bile effluent. This configuration allows for various experiments and determinations to be conducted on each respective effluent (e.g., determine if the respective effluent will kill or not kill a subsequent cell).

Example II—Seeding Cells and Internal Coating of the Device

Figure 19:
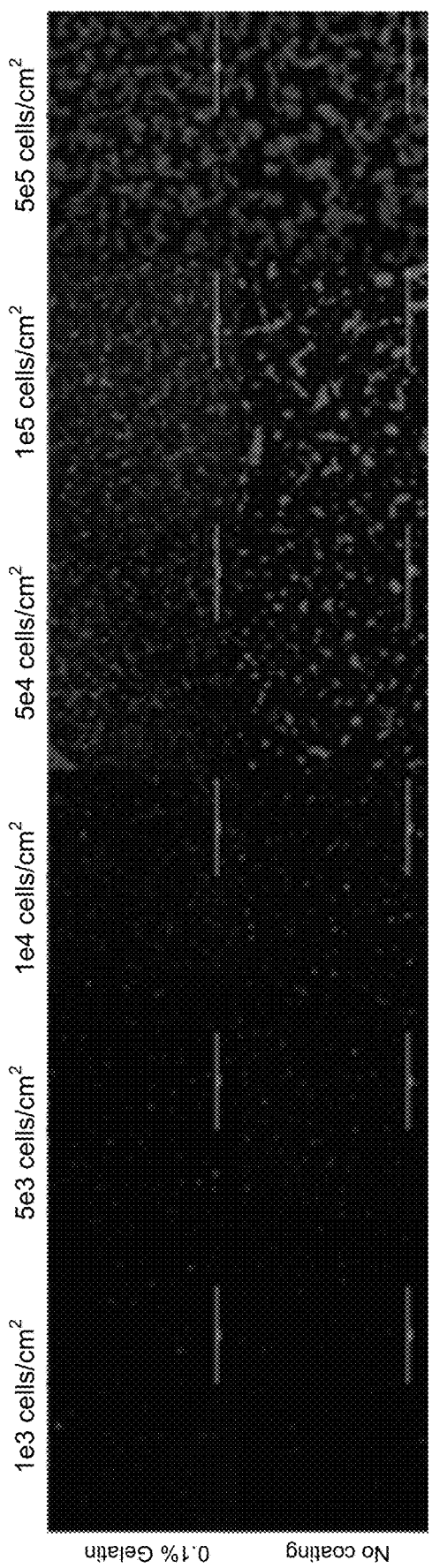
FIG. 19 illustrates fluorescence cleavage induced by controlling various bioreactor system and fabrication system conditions, in accordance with embodiments of the present disclosure.

Referring briefly to FIG. 19, results of various experiments in coating the sidewalls of the well are illustrated. In the experiments of FIG. 19, Hep G2 cell lines were seeded at a density of about $3*10^5$ cells per cubic centimeter and cultured in either static or dynamic conditions (e.g., subjected to a flow of medium). The cells were exposed to fluorescein diacetate (FDA) for one hour in order to detect polarization within the cells. Samples of the medium were captured from the wells of the device, which includes the seeded cells, as well as captured from a portion of the device below the well (e.g., the channel of the device). The results indicated that trends are favorable to increased fluorescence in an upper portion of the device (e.g., an upper portion of the well) as compared to the bottom portion of the device, which lacked the Hep G2 cells. In order to increase cell seeding in the bottom portion of the device, 0.1% gelatin was coated to the respective surfaces of the device prior to the seeding of the cells. Accordingly, as illustrated by the measured cleavage in FIG. 19, optimal density of the seeded cells is achieved by including the 0.1% gelatin coating and seeding the cells at a density of from about $1*10^4$ cells per cubic centimeter to about $1*10^5$ cells per cubic centimeter.

Example III—Seeding Parameters

Figure 20:
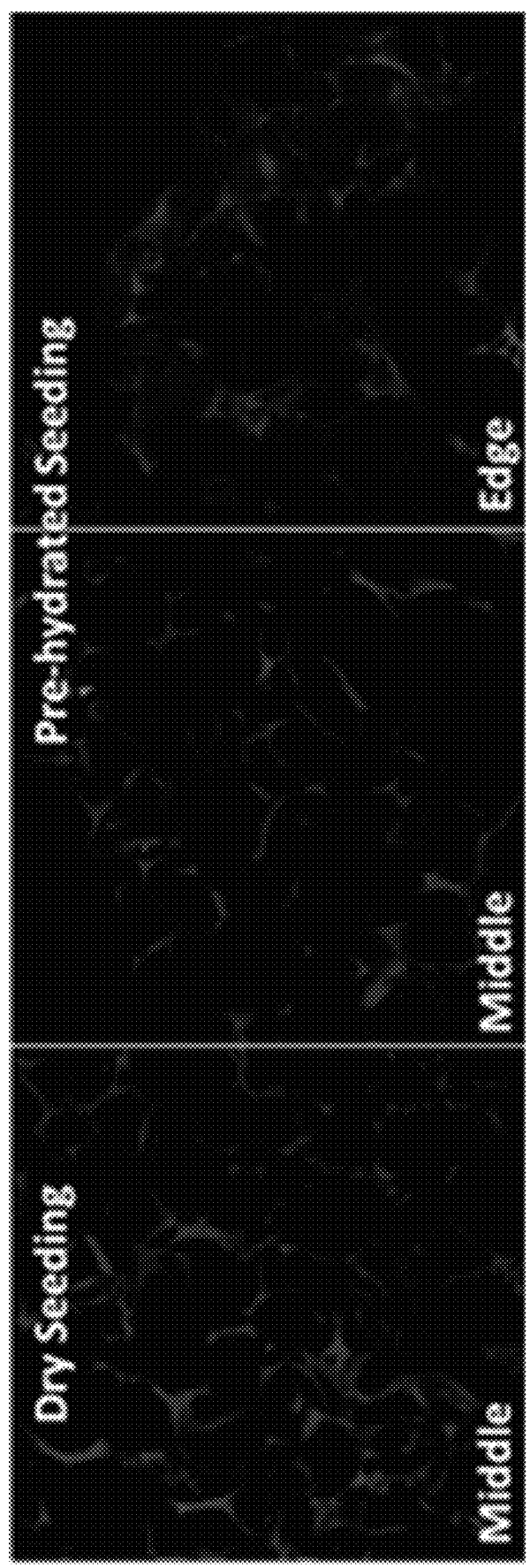
FIG. 20 illustrates additional fluorescence cleavage induced by controlling various bioreactor system and fabrication system conditions, in accordance with embodiments of the present disclosure.
Figure 21:
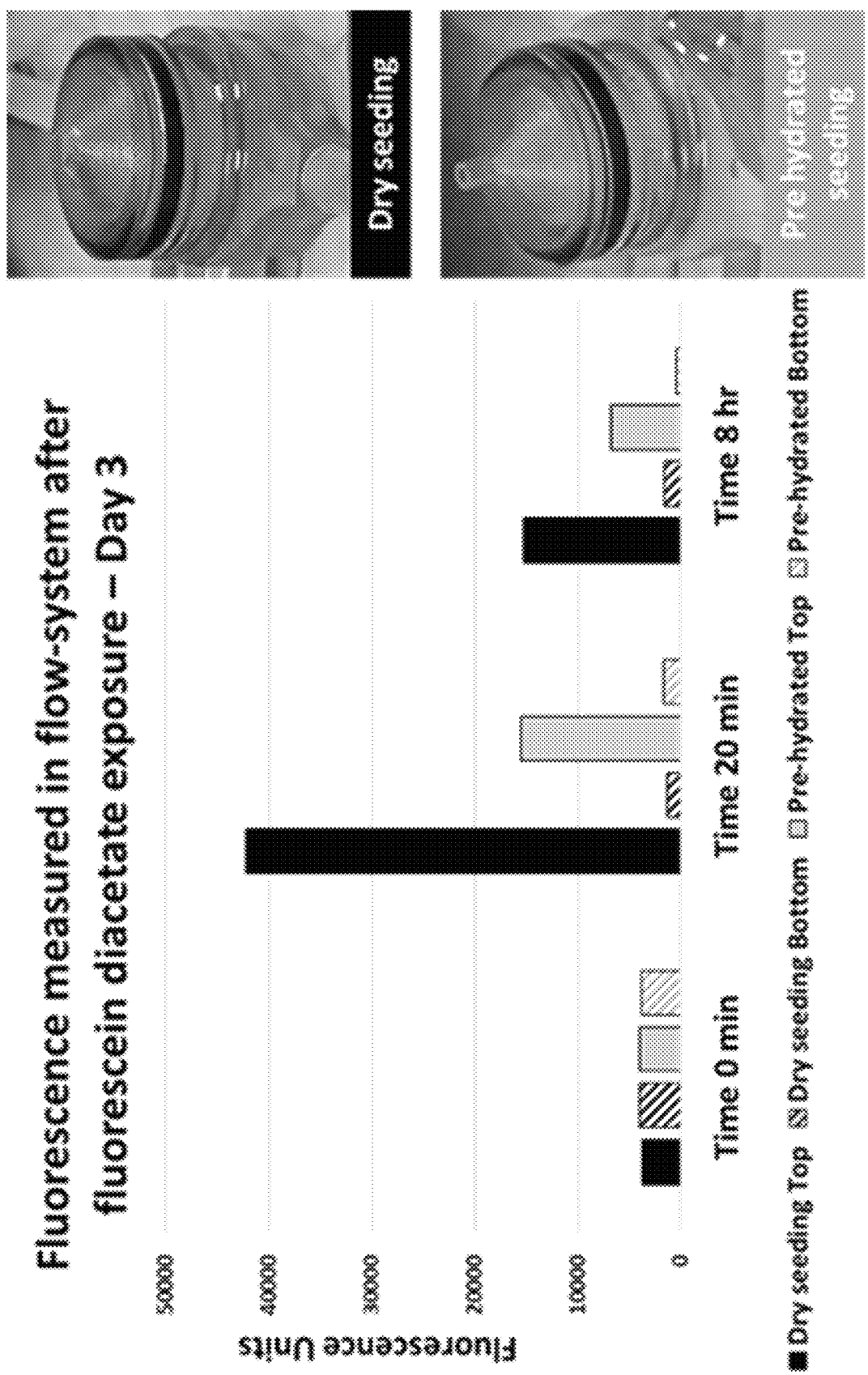
FIG. 21 illustrates a graph of fluorescence cleavage induced by controlling bioreactor system and fabrication system conditions after Hep G2 cell exposure to fluorescein diacetate, in accordance with embodiments of the present disclosure.
Figure 22:
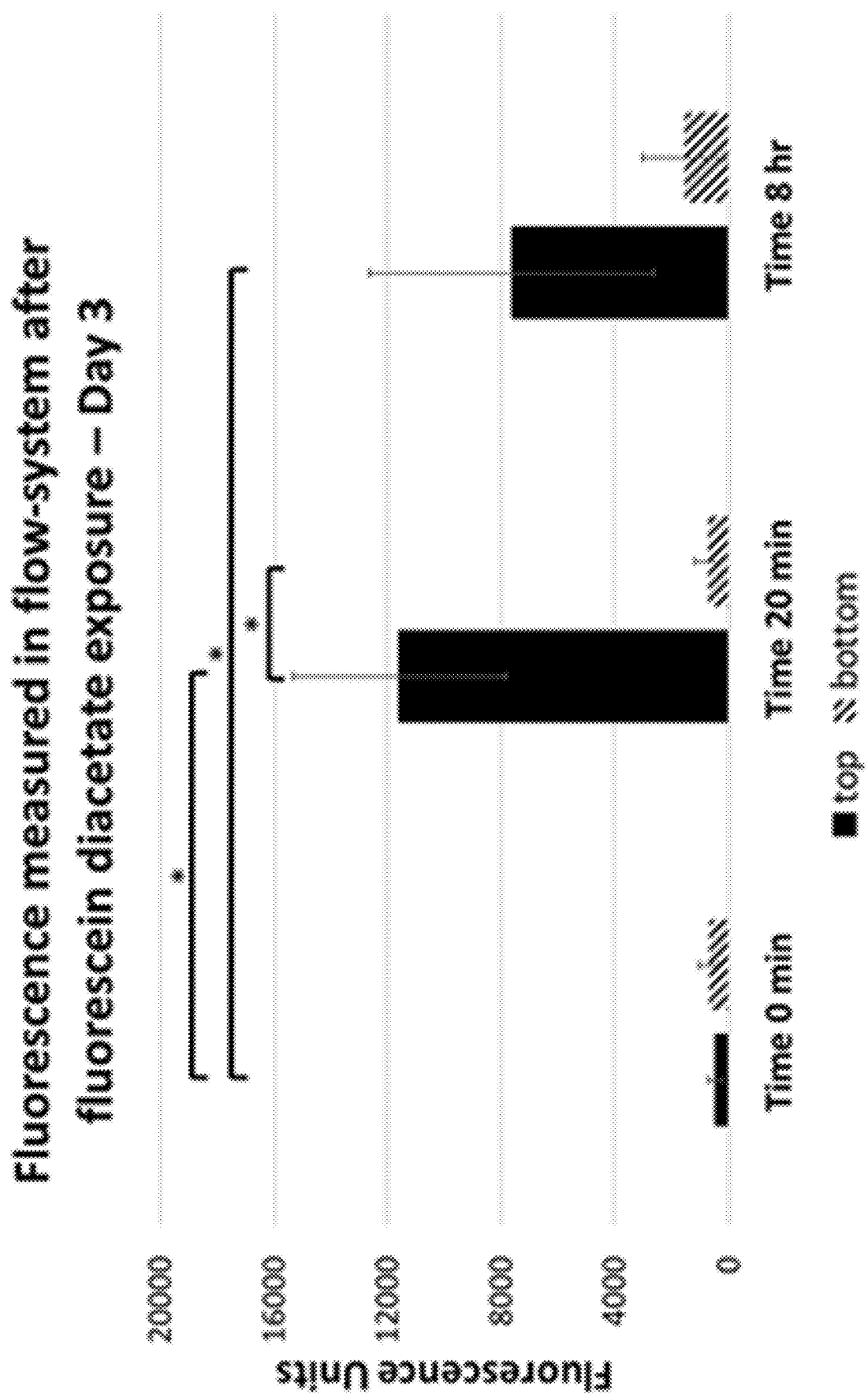
FIG. 22 illustrates another graph of fluorescence cleavage induced by controlling bioreactor system and fabrication system conditions after fluorescein diacetate exposure, in accordance with embodiments of the present disclosure.

In some embodiments, prior to the seeding of cells, the caplet of the device (e.g., a top end portion of the device) is either dry or pre-hydrated, in which the caplet is subjected to the medium and/or gelatin prior to the seeding. Similarly, in some embodiments, prior to the seeding, a bottom end portion of the well of the device is either dry or pre-hydrated. Referring briefly to FIG. 20, FIG. 21, and FIG. 22, results from various experiments related to a protocol of seeding sells are depicted. There figures depict results from experiments in which a cylindrical gelfoam sponge is loaded with about $1*10^6$ Hep G2 cells. These cells proceeded to be cultured under a flow of medium with a flowrate of about 400 µL/min for either three or six days. Additionally, the cells were exposed to about 3 micrograms per milliliter (µg/mL) of fluorescein diacetate while subjected to the above-described flow. Over an eight-hour period of time, media aliquots were captured and measured from below the cell insert (e.g., below the sponge at the bottom end portion of the well) and after passing through the cell insert (e.g., after passing through the sponge at a top end portion of the device), the results of which are depicted in FIG. 20 and FIG. 21. As illustrated in FIG. 20, FIG. 21, and FIG. 22, fluorescence measured below the insert and inside with the cells were approximately equal at the start of the assay. After approximately 20 minutes, the cells began to convert the FDA to fluorescein. Accordingly, a statistical difference was measured between the top portion of the device and the bottom portion of the well after the FDA was added, as illustrated in FIG. 22.

Figure 23:
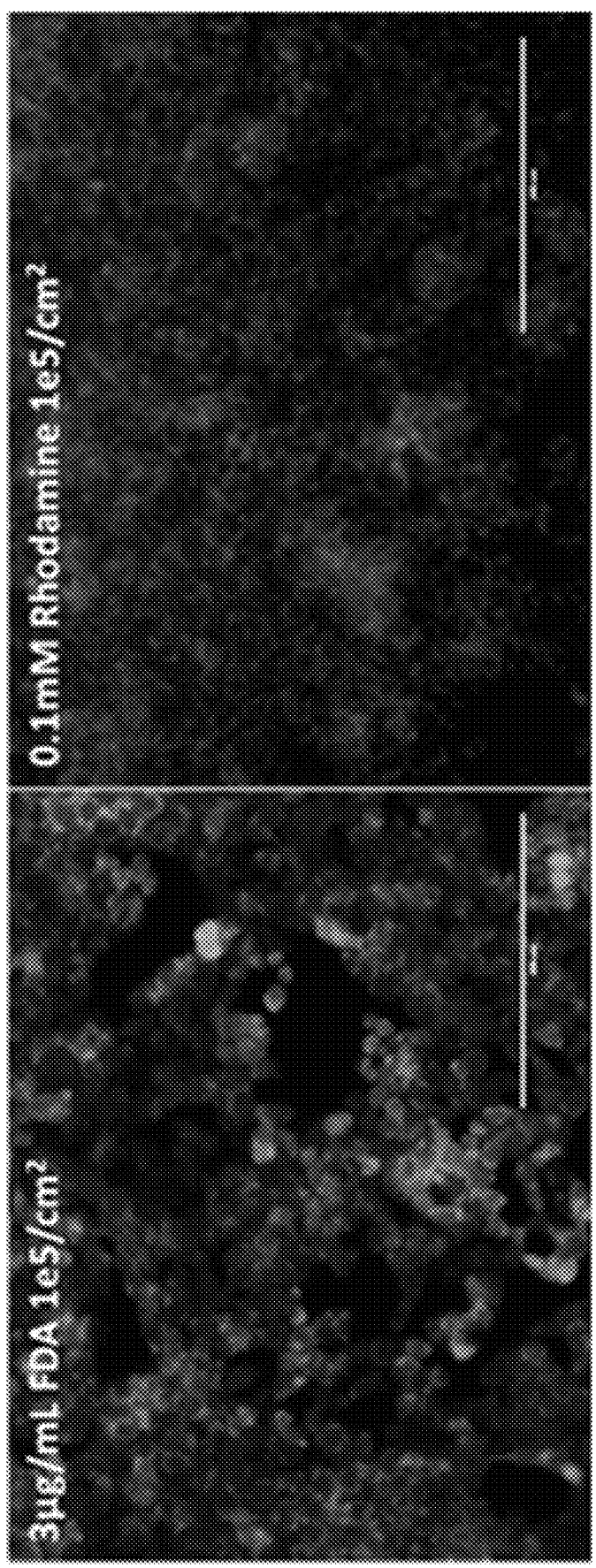
FIG. 23 illustrates further fluorescence cleavage induced by controlling bioreactor system and fabrication system conditions, in accordance with embodiments of the present disclosure.

Referring briefly to FIG. 23, a lower Hep G2 seeding density of about $5*10^4$ cells per cubic centimeter was tested on gelatin coated polyethylene terephthalate (PET) wells. After about 3 days, the lower seeding density was about 80% confluent compared to the 90% confluence of various wells that were seeded with a cell density of about $1*10^5$ cells per cubic centimeter. Each well that was seeded with the lower cell density detached during various washing steps after exposure to either FDA or Rhodamine, whereas wells that were seeded with the higher cell density remained attached. In this experiment, the cells were placed into Hank's balanced salt solution (HBSS) that included calcium and magnesium for about 20 minutes before exposure to either fluorescein diacetate 3 µg/mL or Rhodamine 0.1 mM in HBSS for 20 min. After about 20 minutes, the wells were washed and imaged over about an hour in HBSS. In both instances, bright rings were observable around the edge of most cells, indicating cleavage. This change in exposed resulted in fluorescein cleaved inside of the cell being localized to the outer borders of the cell. Further, this change allowed for better visualization of the cells in culture similar.

Substance Diffusing in a Microchannel Device. Two molecules with different molecules weight were used as substance: FITC-BSA (66500 Da) and Rhodamine B (479 g/mol). Accordingly, 40 µL of 1.0 wt % FTIC-BSA/Rho B solution was applied on an upper surface of hydrogel microchannel device, and washed three times with PBS to remove a fluorescent solution on the surface after about zero to thirty minutes. The fluorescence microscope was used to observe the cross-section of the hydrogel. A diffusion intensity, which simulates a nutrient substance transmission in a hydrogel microchannel device, is important factor for tissue engineering material. Comparing to Rho B, FITC-BSA showed faster diffusion within the hydrogel device, which shows larger molecule as 66.5 kDa could easily transport into and diffuse through the hydrogel device.

Accordingly, the systems and methods of the present disclosure provide a means for directing flow within one or more cell culture devices. These devices are utilized to simulate cell culture in vivo, and are capable of culturing cells with a volume of approximately 1,000 mm³.

For convenience in explanation and accurate definition in the appended claims, the terms "upper", "lower", "up", "down", "upwards", "downwards", "inner", "outer", "inside", "outside", "inwardly", "outwardly", "interior", "exterior", "front", "rear", "back", "forwards", and "backwards" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A method of using an additive manufacture computer system for fabricating a microchannel network device, the method comprising:

(A) receiving, in electronic form, a three-dimensional model of a microchannel network device comprising an identification of: (i) the additive manufacture computer system for fabricating the microchannel network device, (ii) a media accommodated by the microchannel network device, and (iii) a pre-polymer solution utilized at the additive manufacture computer system;

(B) retrieving, from a design module, a plurality of design criteria, wherein each design criteria in the plurality of design criteria is associated with a structural limit of fabricating the microchannel network device;

(C) generating, in electronic form, based on the plurality of design criteria and the three-dimensional model of the microchannel network device, an instance of the microchannel network device, wherein the instance of the microchannel network device comprises:

a dimensionality of a first channel network, a dimensionality of a second channel network based on the first channel network, a structure interposing and providing fluidic communication between the first channel network and the second channel network, and a flow rate of the media through the first channel network or the second channel network;

(D) further generating, based on the identification of the additive manufacture computer system for fabricating the microchannel network device and the pre-polymer solution, one or more instructions for forming the instance of the microchannel network device of a polymer material at the additive manufacture computer system using the pre-polymer solution; and (E) communicating, to the additive manufacture computer system, the one or more instructions for forming the instance of the microchannel network device, thereby utilizing the additive manufacture computer system for fabricating the microchannel network device.

2. The method of claim 1, wherein the polymer material comprises poly-dimethyl-siloxane (PDMS), poly-glycerol-sebacate (PGS), polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyesterspolyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, polytetrafluoroethylene (PTFE), nylon silicon, poly(styrene-block-butadiene), polynorbornene, hydrogels, metallic alloys, oligo (ε-caprolactone)diol, or a combination thereof.

3. The method of claim 1, wherein the polymer material is a biodegradable material.

4. The method of claim 1, wherein:

the pre-polymer solution comprises a photoinitiator, and wherein the one or more instructions comprise an instruction for exposing the pre-polymer solution to ultraviolet light for a predetermined period of time.

5. The method of claim 1, wherein the structure comprises:

a first end portion in communication with the first channel network, wherein the first end portion comprising a first diameter, a second end portion in communication with the second channel network, the second end portion comprising a second diameter, and wherein the first diameter and the second diameter of the structure define an interior transition region of the structure.

6. The method of claim 5, wherein:

the first diameter is from about 992 microns (μm) to about 623 μm, and the second diameter is from about 832 μm to about 553 μm.

7. The method of claim 5, wherein the interior transition region of the structure comprises an interior surface defined by revolving a continuous, smooth curve about an axis of the structure.

8. The method of claim 7, wherein the continuous, smooth curve comprises a conical shape, an ellipsoidal shape, or a cylindrical shape.

9. The method of claim 5, wherein the interior transition region of the structure comprises an interior surface defined by a monotonic function.

10. The method of claim 5, wherein the interior transition region of the structure comprises a corresponding length from about 399 μm to about 701 μm.

11. The method of claim 5, wherein the first diameter is different from the second diameter.

12. The method of claim 1, wherein the plurality of design criteria comprise one or more length design criteria, one or more mass design criteria, one or more temporal design criteria, one or more polymer design criteria, one or more illuminance design criteria, or a combination thereof.

13. The method of claim 12, wherein the one or more polymer design criteria in the plurality of design criteria comprises selecting the polymer based on a degree of swelling of the polymer.

14. The method of claim 12, wherein the one or more polymer design criteria in the plurality of design criteria comprises a porosity of the microchannel network device.

15. The method of claim 14, wherein a median size of a pore of the microchannel network device is from about 19 μm to about 231 μm.

16. The method of claim 1, wherein a length defined from a first end portion to a second end portion of the microchannel network device is from about 15 cm to about 7.5 cm.

17. The method of claim 1, wherein the one or more instructions comprise an instruction for seeding the media through the first channel network and/or the second channel network.

18. The method of claim 1, wherein the one or more instructions comprise an instruction for performing a chemical surface modification for forming the instance of the microchannel network device.

19. The method of claim 1, wherein the one or more instructions comprise an instruction for performing a mechanical surface modification for forming the instance of the microchannel network device.

20. The method of claim 1, the method further comprising, prior to the communicating (E), retaining, at the design module, a record comprising the instance of the microchannel network device and the three-dimensional model of the microchannel network device.

* * * * *